(12) United States Patent
Scheel et al.

(10) Patent No.: US 9,308,238 B2
(45) Date of Patent: Apr. 12, 2016

(54) COMPOSITIONS AND METHODS FOR MODULATING EMT AND USES THEREOF

(75) Inventors: Christina Scheel, Munich (DE); Robert A. Weinberg, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 135 days.

(21) Appl. No.: 13/820,396

(22) PCT Filed: Aug. 30, 2011

(86) PCT No.: PCT/US2011/049781
§ 371 (c)(1),
(2), (4) Date: Sep. 19, 2013

(87) PCT Pub. No.: WO2012/030854
PCT Pub. Date: Mar. 8, 2012

(65) Prior Publication Data
US 2014/0010789 A1    Jan. 9, 2014

Related U.S. Application Data

(60) Provisional application No. 61/379,327, filed on Sep. 1, 2010.

(51) Int. Cl.
| C12N 5/00 | (2006.01) |
| A61K 35/36 | (2015.01) |
| A61K 38/18 | (2006.01) |
| A61K 45/06 | (2006.01) |

(52) U.S. Cl.
CPC .............. *A61K 38/1841* (2013.01); *A61K 35/36* (2013.01); *A61K 45/06* (2013.01)

(58) Field of Classification Search
CPC .... A61K 38/1841; A61K 45/06; A61K 35/36
See application file for complete search history.

(56) References Cited

U.S. PATENT DOCUMENTS

| 2008/0070303 A1* | 3/2008 | West et al. ............... 435/377 |
| 2009/0143394 A1 | 6/2009 | Wyss-coray et al. |
| 2009/0214483 A1 | 8/2009 | Weinberg et al. |
| 2010/0233804 A1 | 9/2010 | Zhou et al. |
| 2012/0028355 A1 | 2/2012 | Sato et al. |
| 2012/0095000 A1 | 4/2012 | Wyss-coray et al. |
| 2012/0258084 A1 | 10/2012 | Weinberg et al. |

FOREIGN PATENT DOCUMENTS

| EP | 2274617 | 1/2011 |
| WO | WO 2007/005611 | 1/2007 |
| WO | WO 2009/051660 | 4/2009 |
| WO | WO 2011/047300 | 4/2011 |
| WO | WO 2012/030854 | 3/2012 |
| WO | WO 2013/131000 | 9/2013 |

OTHER PUBLICATIONS

Xu et al., TGF-β-induced epithelial to mesenchymal transition. Cell Research, vol. 19 (2009) pp. 156-172.*
International Search Report for International Application PCT/US2013/028665, dated Jun. 20, 2013.
Dissanayake, et al., "The Wnt5A/protein of kinase C pathway mediates motility in melanoma cells via the inhibition of metastasis suppressors and initiation of an epithelial to mesenchymal transition," *J. Biol. Chem.*, 282(23): 17259-17271 (2007).
Kalluri, et al., "The basics of epithelial-mesenchymal transition", *J. Clin. Invest.*, 119(6): 1420-1428 (2009).
Koenigshoff, et al., "WNT signaling in lung disease: a failure or a regeneration signal", *Am. J. Respir. Cell Mol. Biol.*, 42(1): 21-31 (2010).
Pongracz, et al., Wnt signaling in lung development and diseases:, *Respir. Res.*, 7(15): 1-3, 5-7 (2006).
International Search Report for International Application PCT/US2011/049781, dated Apr. 27, 2012.
Brown, et al., "Induction by transforming growth factor-[beta]1 of epithelial to mesenchymal transition is a rate event in vitro", *Breast Cancer Research, Current Science*, 6(3):R215-R231(2004).
Huberger, et al., "Interplay of Cadherin-Mediated Cell Adhesion and Canonical Wnt Signaling", *Cold Spring Harbor Perspectives in Biology*, 2(2):a002915-a002915(2009).
Nishioka, et al., "Snail induces epithelial-to-mesenchymal transition in a human pancreatic cancer cell line (BxPC3) and promotes distance metastasis and invasiveness in vivo", *Experimental and Molecular Pathology Academic Press*, 89(2):149-157(2010).
Kalluri, et al., "The basics of epithelial-mesenchymal transition", *Journal of Clinical Investigation*, 119(6):1420-1428(2009).
Sabbah, et al., "Molecular signature and therapeutic perspective of the epithelial-to-mesenchymal transitions in epithelial cancers", *Drug Resistance Updates*, 11(4-5):123-151(2008).
Thiery, et al., Epithelial-Mesenchymal Transitions in Development and Disease, *Cell*, 139(5):871-890(2009).
Supplementary European Search Report for European Application EP11822507, dated Feb. 10, 2014.
Avsian-Kretchmer, et al., "Comparative Genomic Analysis of the Eight-Membered Ring Cystine Knot-Containing Bone Morphogenetic Protein Antagonists", *Molecular Endocrinology*, 18: 1-12(2004).

(Continued)

*Primary Examiner* — Laura Schuberg
*Assistant Examiner* — Kara Johnson
(74) *Attorney, Agent, or Firm* — Lisa M. Warren, Esq.; Morse, Barnes-Brown & Pendleton, P.C.

(57) ABSTRACT

The invention provides compositions and methods useful for modulating epithelial-mesenchymal transition (EMT). Certain of the compositions and methods are useful for inducing epithelial cells to undergo an EMT. The invention further provides cells generated using the inventive methods and methods of use thereof. Certain of the compositions and methods are useful for inhibiting epithelial cells from undergoing an EMT. Certain of the compositions and methods are useful for inhibiting EMT in a subject in need thereof.

16 Claims, 50 Drawing Sheets

(56) References Cited

OTHER PUBLICATIONS http://www.stanford,edu/~rnusse/wntwindow.html, accessed online May 31, 2013, Dec. 18, 2009.

Mani, et al., "The epithelial-mesenchymal transition generates cells with properties of stem cells", *Cell*, 133:704-715(2008).

Zavadil, et al., "Genetic programs of epithelial cell plasticity directed by transforming growth factor-β", *Proceedings of the National Academy of Sciences of the United States of America*, 98:6686-6691(2001).

International Preliminary Report on Patentability for International Application PCT/US2011/049781, dated Mar. 14, 2013.

* cited by examiner

| Cells injected | Tumor incidence/ Number of injections | | |
|---|---|---|---|
| | $1 \times 10^5$ | $1 \times 10^4$ | $1 \times 10^3$ |
| HMLE[24+]+RAS | 5/5 | 0/5 | 0/5 |
| HTwist+RAS | 5/5 | 5/5 | 5/5 |
| MSP+RAS | 5/5 | 5/5 | 4/5 |

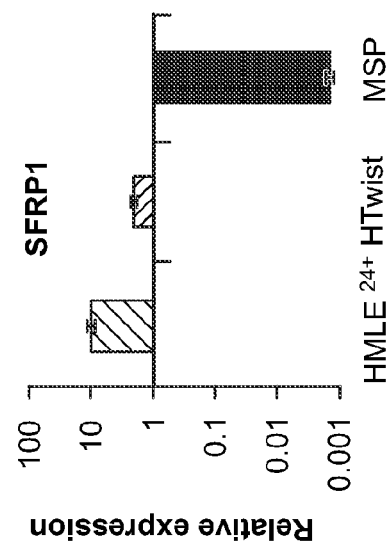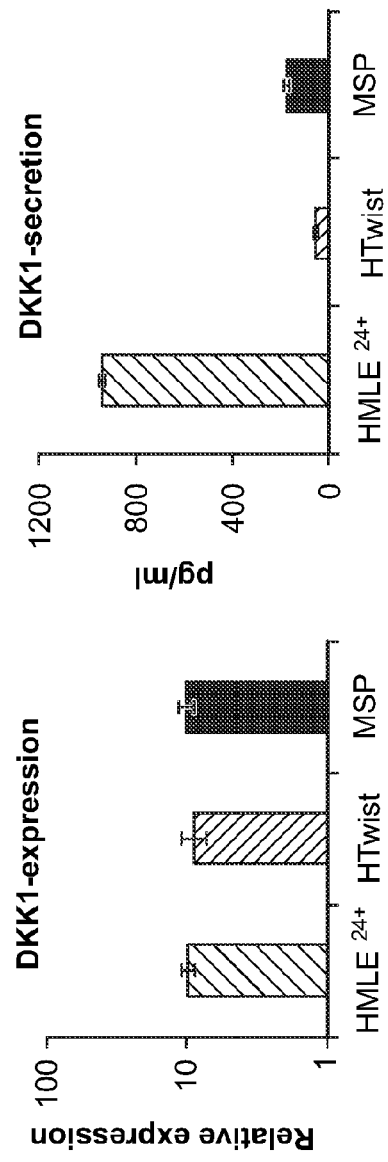
FIG. 2F
FIG. 2G

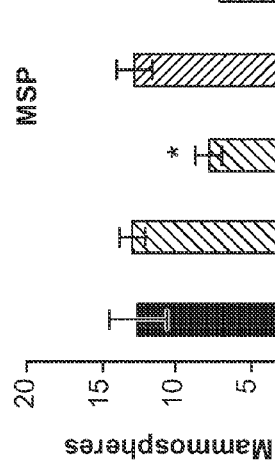
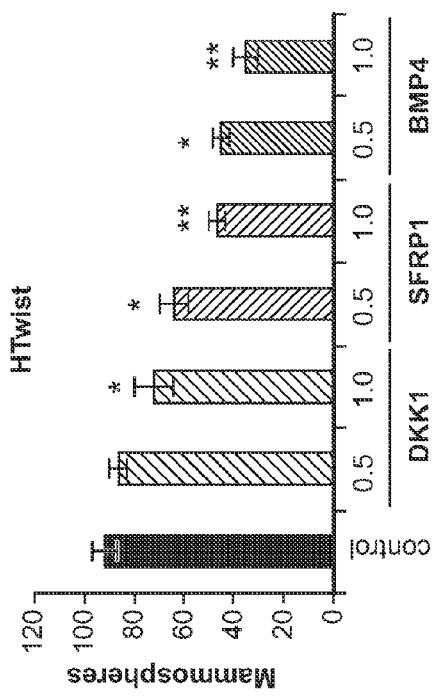
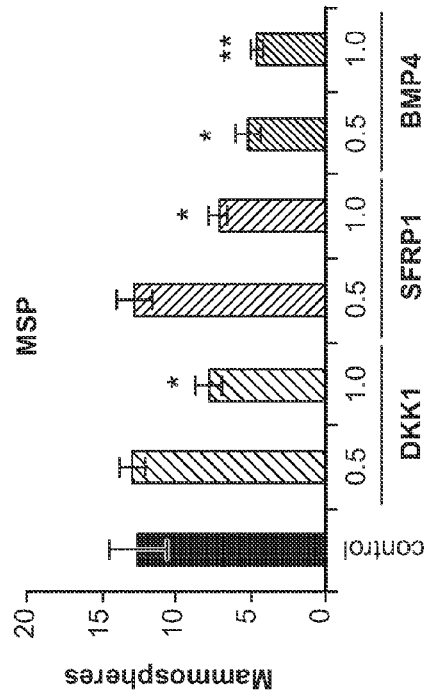
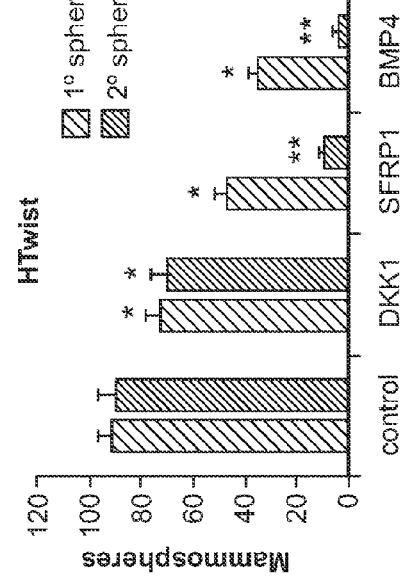
FIG. 3D
FIG. 3E

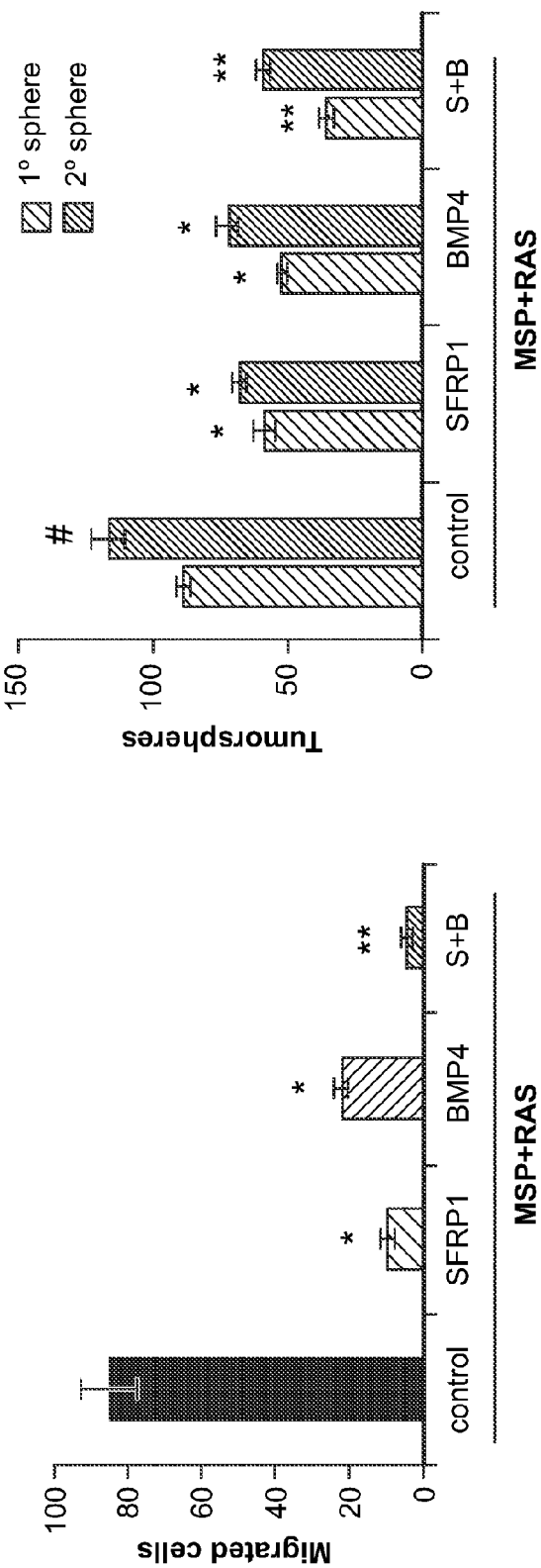
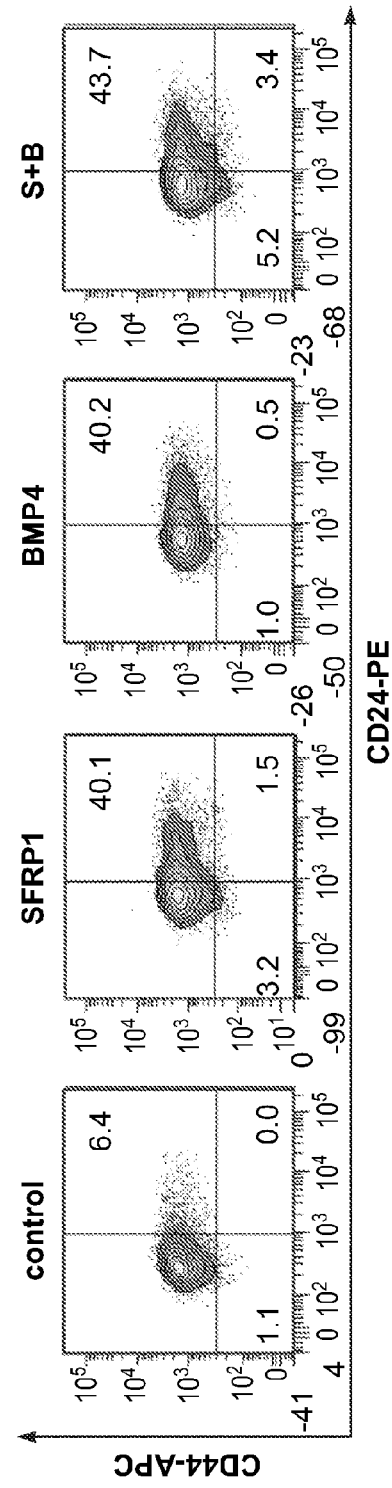
FIG. 4A
FIG. 4B
FIG. 4C

| Number of cells injected: | Tumor incidence/ Number of injections | | | |
|---|---|---|---|---|
| | Control | SFRP1 | BMP4 | S+B |
| 5x10⁵ | 5/5 | 5/5 | 3/5 | 3/5 |
| 5x10⁴ | 10/10 | 4/10 | 4/10 | 4/10 |
| 5x10³ | 4/5 | 1/5 | 1/5 | 0/5 |

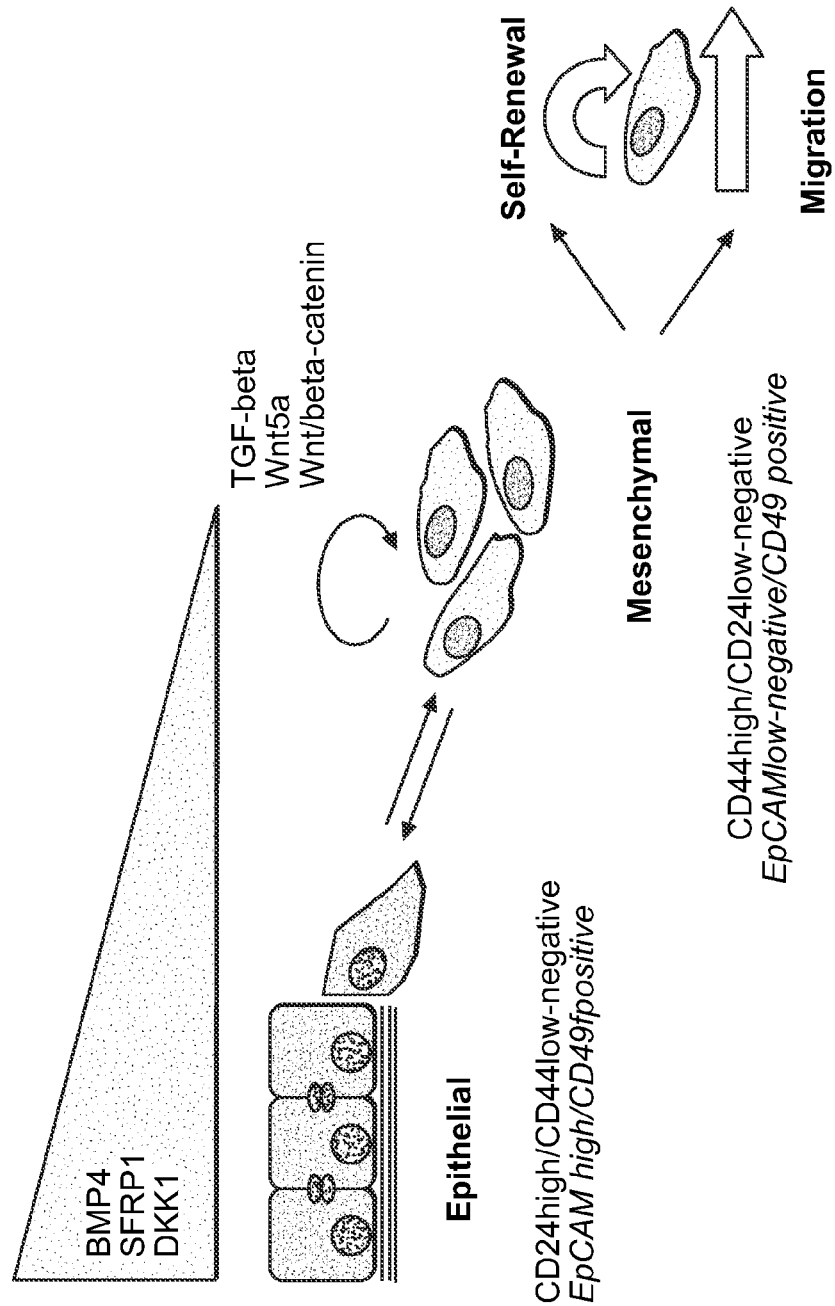

| | Array | Elisa |
|---|---|---|
| VEGF-c | 1.2 | 1.2 |
| PTX3 | 2.8 | 25.6 |
| uPA | 2.5 | 4.5 |
| DKK1 | 1.4 | 3.5 |

FIG. 9D

| Protein | Function | Down in MSP | Down in HTwist | Up in HTwist | Up in MSP | Method of Detection |
|---|---|---|---|---|---|---|
| DKK1* | Wnt antagonist | X | XX | | | ELISA |
| SFRP1** | Wnt antagonist | XX | X | | | RT-PCR |
| Chordin-like2* | BMP antagonist | | | X | X | RT-PCR |
| Gremlin1** | BMP antagonist | | | X | XX | RT-PCR |
| Wnt5a** | Wnt ligand, non-canonical | | | XX | X | Western Blot |
| Wnt16 | Wnt ligand, non-canonical | | | X | X | RT-PCR |
| Wnt1 | Wnt ligand, canonical | XX | X | | | RT-PCR |
| Wnt4 | Wnt ligand, canonical | XX | X | | | RT-PCR |
| Wnt5b | Wnt ligand, non-canonical | X | X | | | RT-PCR |
| Wnt7a | Wnt ligand, canonical | X | XX | | | RT-PCR |
| Wnt8a | Wnt ligand, canonical | XX | X | | | RT-PCR |
| Wnt8b | Wnt ligand, canonical | X | X | | | RT-PCR |
| Wnt10 | Wnt ligand, non-canonical | X | X | | | RT-PCR |
| BMP2 | Bmp ligand | X | X | | | RT-PCR |
| BMP4 | Bmp ligand | XX | X | | | RT-PCR |
| BMP5 | Bmp ligand | X | XX | | | RT-PCR |
| BMP6 | Bmp ligand | X | X | | | RT-PCR |
| BMP7 | Bmp ligand | XX | X | | | RT-PCR |
| BMP9 | Bmp ligand | XX | X | | | RT-PCR |
| BMP10 | Bmp ligand | X | XX | | | RT-PCR |
| TGF-beta1 | TGF-beta ligand | | | X | XX | ELISA |

* first revealed by protein array, ** first revealed by gene expression profiling

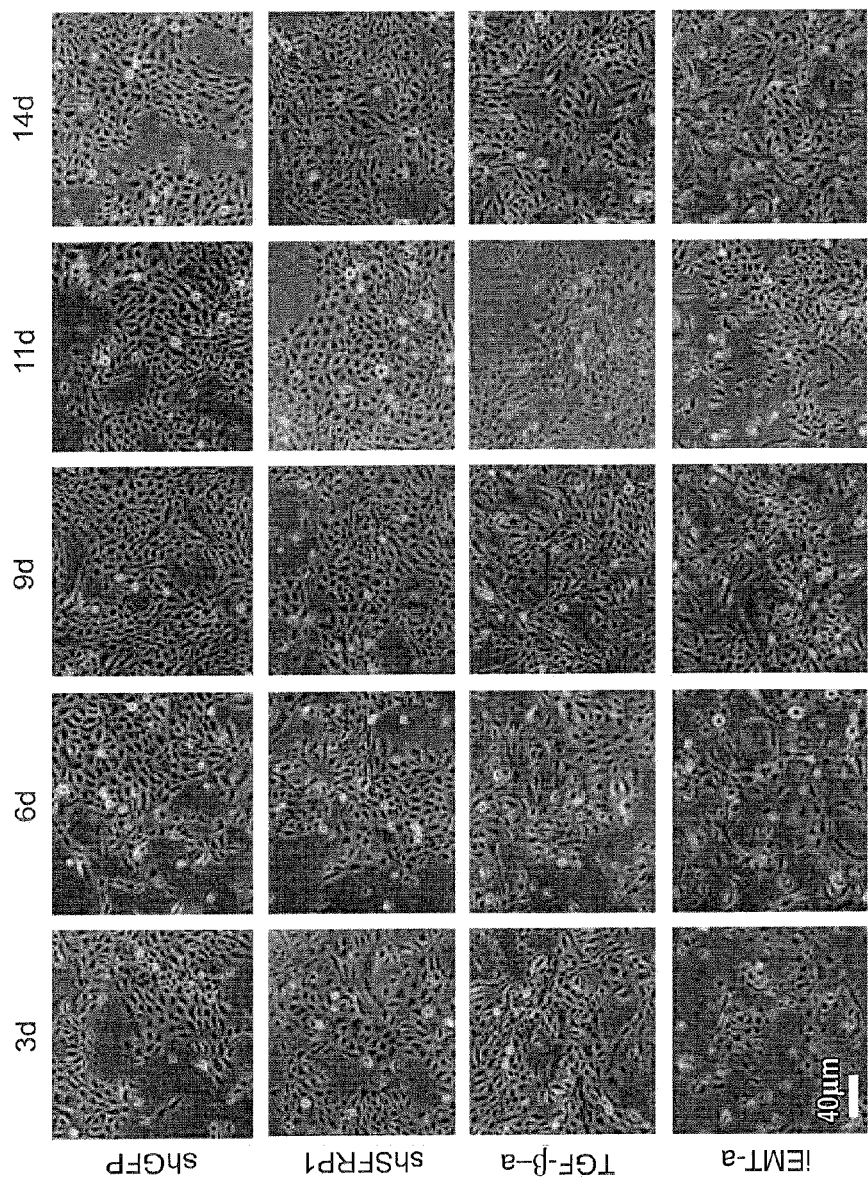

Basal MECS control

A83-01

SB43

SFRP1

20μm

COMPOSITIONS AND METHODS FOR MODULATING EMT AND USES THEREOF

RELATED APPLICATIONS

This application is a national stage filing under 35 U.S.C. 371 of International Application No. PCT/US2011/049781, filed Aug. 30, 2011, which claims priority to and the benefit of U.S. Application No. 61/379,327, filed Sep. 1, 2010, the teachings of which are incorporated herein by reference. International Application PCT/US2011/049781 was published under PCT Article 21(2) in English.

GOVERNMENT FUNDING

This invention was made with government support under W81XWH-08-01-0464, awarded by the Department of Defense (Army); DE020817, awarded by the National Institutes of Health; and CA012515, awarded by the National Institutes of Health. The government has certain rights in the invention.

BACKGROUND OF THE INVENTION

The epithelial-mesenchymal transition (EMT) is a transdifferentiation program that effects critical steps of embryogenesis by interconverting epithelial cell types into cells with mesenchymal attributes. EMT programs are also activated in carcinoma cells, enabling them to acquire cellular traits associated with high-grade malignancy, including the ability to complete various steps of the metastatic cascade. In addition to mesenchymal traits, recent findings suggest that adult epithelial cells that pass through an EMT also acquire properties associated with normal tissue stem cells (SCs) and tumor-initiating cells. There is significant interest in the art in inducing or inhibiting EMT programs.

SUMMARY OF THE INVENTION

The present invention provides compositions and methods useful for modulating the epithelial-mesenchymal transition. In one aspect, the invention provides a composition comprising one or more compounds selected from each of at least three of the following groups: (a) compounds that stimulate TGF-beta pathway signaling; (b) compounds that stimulate canonical Wnt pathway signaling; (c) compounds that stimulate non-canonical Wnt pathway signaling; and (d) compounds that perturb cell adhesion. In some embodiments, the composition comprises at least one compound from each of these four groups.

In another aspect, the invention provides a composition comprising one or more compounds selected from each of at least three of the following groups: (a) compounds that inhibit TGF-beta pathway signaling; (b) compounds that inhibit canonical Wnt pathway signaling; (c) compounds that inhibit non-canonical Wnt pathway signaling; and (d) compounds that stimulate BMP signaling. In some embodiments, the composition comprises at least one compound from each of these four groups.

In other aspects, the invention provides methods of inducing or inhibiting EMT, using, e.g., an inventive composition.

Certain conventional techniques of cell biology, cell culture, molecular biology, microbiology, recombinant nucleic acid (e.g., DNA) technology, immunology, etc., which are within the skill of the art, may be of use in aspects of the invention. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., editions as of 2008; Sambrook, Russell, and Sambrook, *Molecular Cloning: A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Burns, R., *Immunochemical Protocols* (Methods in Molecular Biology) Humana Press; 3rd ed., 2005, Monoclonal antibodies: a practical approach (P. Shepherd and C Dean, eds., Oxford University Press, 2000); Freshney, R. I., "Culture of Animal Cells, A Manual of Basic Technique", 5th ed., John Wiley & Sons, Hoboken, N.J., 2005; Cancer: Principles and Practice of Oncology (V. T. De Vita et al., eds., J. B. Lippincott Company, $8^{th}$ ed., 2008). Further information on cancer may be found in The Biology of Cancer, Weinberg, R A, et al, Garland Science, 2006. All patents, patent applications, websites, databases, scientific articles, and other publications mentioned herein are incorporated herein by reference in their entirety.

BRIEF DESCRIPTION OF THE DRAWING

(FIG. 1A) Bright phase microscopy: images of epithelial HMLE[24+], HMLE overexpressing Twist (HTwist) and MSP cells. (FIG. 1B) Immunoblot: E- and N-Cadherin, EMT transcription factors (TFs) Zeb1, Snail and Slug. (FIG. 1C) Immunofluorescence: expression and nuclear localization of EMT-TF Twist in HMLE[24+], HTwist and MSP cells, levels of mesenchymal intermediary filament vimentin and epithelial cytokeratins (panCK=pan-cytokeratin antibody). (FIG. 1D) RT-PCR: expression of EMT-TFs, E- and N-Cadherin in HTwist and MSP relative to HMLE[24+] cells, L32 was loading control, n=3. (FIG. 1E) Mammosphere Assay: bright phase microscopy images of mammospheres and quantification, mammospheres/1500 cells, n=24/cell line. (FIG. 1F) Flow cytometry of CD44 and CD24 cell surface markers. (FIG. 1G) Tumorigenicity assay: RAS-transformed HMLE[24+], HTwist and MSP cells were implanted subcutaneously at indicated numbers in mice. (FIG. 1H) Boyden Chamber Invasion assay: Bright phase microscopy images of invaded, HMLE[24+]-RAS, MSP-RAS, MSP-II-RAS cells and quantification, n=3. (FIG. 1I) Lung metastasis: HMLE[24+]-RAS, MSP-RAS and MSP-II-RAS cells were implanted in the fat pads of mice: microscope images of the major left lung lobe showing GFP-expressing metastatic nodules, magnified inset and quantification of lung surface metastases, n=5 mice/group.

FIGS. 2A-2J. Autocrine TGF-beta and Wnt signaling in HTwist and MSP cells. (FIG. 2A) ELISA: TGF-beta 1 secretion in HMLE[24+], HTwist and MSP cells, n=3. (FIG. 2B) Luciferase reporter assay: Smad transcriptional activity: cells were transfected with SBE4-luc reporter plasmid, firefly luciferase levels were normalized to pGL-SV40 *renilla* transfection control, n=3. (FIG. 2C) Immunoblot: smad2 phosphorylation in HMLE[24+], HTwist and MSP cells. (FIG. 2D) Immunoblot: before lysis, cells were cultivated for 24 hr in either regular medium (++), growth factors reduced to 10% of regular concentration (+), or in growth factor-free medium (−). (FIG. 2E) RT-PCR: BMP antagonists Gremlin, Chordin-like 2, L32 was loading control, n=3. (FIG. 2F) RT-PCR: SFRP1, L32 was loading control, n=3. (FIG. 2G) RT-PCR: DKK1, L32 was loading control, n=3, ELISA: DKK1 secretion (n=3). (FIG. 2H) Immunoblot: activation status of pathways associated with non-canonical Wnt signaling. (FIG. 2I) Luciferase reporter assay (TOPFlash): cells were transfected with Super(8x)TOP (TCF-LEF reporter) or FOP construct (control, binding sites mutated). Shown is TOP over FOP firefly luciferase activity, normalized to pGL-SV40 renilla transfection control, n=3. (FIG. 2J) Inhibition of TOPFlash activity: DKK1 or SFRP1 recombinant protein (1.0 µg/ml) were added to the growth medium of HTwist and MSP cells 12 h before lysis, n=3.

FIGS. 3A-3E. Autocrine Signaling controls migration and mammosphere formation. (FIG. 3A) Migration assay: cells were seeded into Boyden chambers and recombinant DKK1 or SFRP1 protein (0.5 µg/ml) was added to growth medium; #HMLE control vs. HTwist and MSP control, $p<1\times10^{-6}$, *HTwist or MSP control vs. treatment with DKK1 or SFRP1, $p<1\times10^{-6}$, n=3. (FIG. 3B) Migration assay: dose-dependent inhibition of migration by DKK1 or SFRP1 protein at indicated concentrations (µg/ml), n=3; *H-Twist or MSP control vs. treatment with DKK1 or SFRP1, p $p<1\times10^{-6}$, ** H-Twist or MSP, high vs. low concentrations, $p<1\times10^{-7}$, n=3. (FIG. 3C) Migration assay: dose-dependent inhibition of migration by recombinant BMP4 protein at indicated concentrations (µg/ml); *HTwist or MSP control, $p<0.05$, **0.6 µg/ml vs. 1.2 ug/ml, $p<1\times10^{-4}$, n=3. (FIG. 3D) Mammosphere formation: recombinant DKK1, SFRP1 or BMP4 protein were added daily during sphere formation (5 days) at indicated concentrations (µg/ml); *HTwist or MSP control vs. treatment, $p<0.01$, **low vs. high concentration or recombinant protein, $p<0.05$, n(mammospheres)/1000 cells, n=8. (FIG. 3E) Secondary mammosphere formation: DKK1 (1 µg/ml), SFRP1 (1 µg/ml) and BMP4 (0.5 µg/ml) were added daily during primary sphere formation (5 days), spheres were dispersed and seeded for secondary sphere formation in absence of further treatment; *H-Twist or MSP control vs treatment, $p<0.01$, **primary vs. secondary sphere number, $p<0.01$, n(mammospheres)/1000 cells, n=16.

FIGS. 4A-4G. Autocrine Signaling controls tumorigenicity and metastasis of MSP-RAS cells. (FIG. 4A) Migration assay: RAS-transformed MSP (MSP-RAS) were seeded in Boyden Chamber migration assays and recombinant SFRP1 (1 µg/ml) and BMP4 protein (0.5 µg/ml) were added; *control vs. single treatment, $p<1\times10^{-8}$, **single vs. double treatment with SFRP1 and BMP4 (S+B), $p<1\times10^{-4}$, n=3. (FIG. 4B) Tumorsphere assay: SFRP1 (1 µg/ml) and BMP4 protein (0.5 µg/ml) were added daily during primary sphere formation (5 days), spheres were dispersed and seeded for secondary sphere formation in the absence of further treatment; #control primary vs. secondary sphere formation, p=0.001; *control vs. single treatment, $p<1\times10^{-4}$, **single vs. double treatment with SFRP1 and BMP4 (S+B), $p<0.01$, n(tumorspheres)/1000 cells, n=6. (FIG. 4C) Flow cytometry: CD44 and CD24 cell-surface markers of dissociated primary tumorspheres as described in (B). (FIG. 4D) Orthotopic tumor formation after ex vivo treatment during tumorsphere formation: primary tumorspheres as generated in (B) were pooled, dissociated and $1.0\times10^5$ cells were implanted in the fat pads of mice; shown are tumor weight and incidence, *indicates absence of tumor, n=5 mice/group. (FIG. 4E) Lung metastasis: fluorescence microscopy images of the major left lung lobe showing GFP-expressing metastatic nodules and quantification of the number of lung surface metastases; *control vs. SFRP1 treatment, $p<0.05$, **SFRP1 vs. BMP4 or double treatment (S+B), $p<0.05$, n=5 mice/group. (FIG. 4F) Liver metastasis: fluorescence microscopy images of the liver surface showing GFP-expressing micro-metastatic nodules after implantation of cells as described in (D) and quantification: 5 fields of liver surface were counted per mouse, *control vs. single treatment, $p<0.05$, **single vs. double treatment (S+B), $p<0.05$, n=5 mice/group. (FIG. 4G) Tumorigenicity assay: MSP-RAS cells suspended in PBS containing SFRP1 (1 µg/ml), BMP4 (0.5 µg/ml), and a combination of both (S+B) were implanted subcutaneously in mice at indicated cell numbers. In addition, 20 µl of PBS or PBS with proteins at indicated doses was injected peri-tumorally at 1, 2, 3 and 7 days after implanting the MSP-RAS cells.

(FIG. 5A) RT-PCR: N-Cadherin, Zeb1 and Zeb2, L32 was loading control, n=3. Prior RNA isolation, HMLE$^{24+}$-shGFP or -shSFRP1 (stable knockdown of SFRP1, FIG. 12A) cells were treated for 3 days with daily doses of indicated factors: anti-DKK1 antibody (10 µg/ml), anti-E-Cadherin antibody (1 µg/ml), TGF-beta 1 (5 ng/ml), Wnt5a (250 ng/ml), (FIG. 5B) Brightfield microscopy: images of control, TGF-beta- and iEMT-cocktail treated HMLE$^{24+}$ cells after 14 days of treatment as indicated (see also FIG. 12D). (FIG. 5C) RT-PCR: Zeb1, Zeb2, E-Cadherin and N-Cadherin, L32 was loading control, n=3. After 14 day treatment, cells were expanded in absence of further stimulation for 4 passages. Shown are PBS-treated control HMLE$^{24+}$-shGFP and HMLE$^{24+}$-shSFRP1 cells, two HMLE$^{24+}$-shGFP cultures treated with TGF-beta 1 (TGF-β-a and -b), two HMLE$^{24+}$-shSFRP1 cultures treated with the iEMT-cocktail (iEMT-a and -b). (FIG. 5D) Immunoblot: EMT markers and associated autocrine pathways, cells generated as described in (C). (FIG. 5E) Migration (Boyden Chamber Assay) and Mammosphere Assay: cells generated as indicated in (C), *control vs. TGF-beta treatment, $p<1\times10^{-4}$, **control vs. iEMT-treatment, $p<1\times10^{-9}$, n(migration)=3, n(mammospheres)/1000 cells, n=7. (FIG. 5F) Flow cytometry: CD44 and CD24 cell-surface marker expression in control, TGF-beta-a and iEMT-a cells generated as described in (C). (FIG. 5G) Lung metastasis: cells expanded for 8 passages after cessation of treatment as described in (C) were transformed with RAS; $1.0\times10^5$ cells were injected into the mammary fat pads of mice; GFP-labeled metastases on the surface of the lungs were quantified; *control vs. all other groups, $p<0.05$, n=5 mice/group. (FIG. 5H) Migration (Boyden Chamber Assay) and Mammosphere Assay: HMLE-iEMT-a were expanded for 12 passages after cessation of treatment as described in (C), then seeded into assays in presence of recombinant SFRP1 (1 µg/ml/d), BMP4 (0.5 µg/ml/d) or both (S+B) protein; *control vs. single treatment, $p<0.01$, **single vs. double treatment (S+B), $p<0.05$, n(migration)=3, n(mammospheres)/1000 cells, n=6.

(FIG. 6A) FACS: single-cell preparations from human reduction mammoplasties; (1.) dead cells were excluded by 7AAD staining, followed by (2.) exclusion of cells positive for CD45 (white blood cells) and CD31 (endothelial cells). (3.) Using the resultant Lin- cells, basal (CD49fpositive/EpCAM low-negative) and luminal (CD49fpositive/EpCAM-positive) cell populations were collected. (FIG. 6B) Bright phase microscopy: purified basal, luminal and unsorted bulk MECs were cultured for 5 days after FACS. (FIG. 6C) Immunofluorescence: basal and luminal MEC populations were cultured for 5 days after FACS; luminal lineage markers; cytokeratins (CK) 8, 18, and MUC1; nuclear staining with DAPI. (FIG. 6D) Immunofluorescence: basal lineage markers CK 14, p63; myoepithelial lineage marker alpha-smooth muscle actin (alpha-SMA); nuclear staining with DAPI (FIG. 6E) Immunofluorescence: mesenchymal and epithelial markers; vimentin, tight-junction protein ZO-1 and beta catenin, nuclear staining with DAPI (FIG. 6F) Immunofluorescence: EMT-associated signaling: Smad2, TFs Twist and Zeb1, nuclear staining with DAPI.

FIGS. 7A-7G. Migratory and self-renewal properties in primary MECs: inhibition and induction. (FIG. 7A) Mammosphere Assay: microscopy images of mammospheres and quantification of mammosphere formation by purified basal, luminal and unsorted MEC populations. Primary spheres were allowed to form over a period of 7 days, dissociated and seeded for secondary sphere formation, n(mammosphere)/1000 cells, n=48, (FIG. 7B) Migration Assay: microscopy images of migrated cells in Boyden Chambers and quantification, n=6. (FIG. 7C) Mammosphere Assay: basal cells were seeded into assay after a 5 day pre-treatment with TGF-beta inhibitors A83-01 and SB435142 (SB43, both inhibitors at 10 µM) as well as recombinant SFRP1 (1 µg/ml), n(mammospheres)/1000 cells, n=6. (FIG. 7D) Migration Assay: basal cells were seeded into migration assays treated after 5 day pre-treatment as described in (C), n=24. (FIG. 7E) Mammosphere Assay: luminal cells were seeded into the assay following a 5 day pre-treatment with TGF-beta 1 (5 ng/ml), Wnt5a (250 ng/ml), anti-E-Cadherin antibody (1 µg/ml) plus anti-DKK1 antibody (10 µg/ml), and a cocktail of all factors added together (iEMT-II), n(mammospheres)/1000 cells, n=24. (FIG. 7F) Migration Assay: luminal cells were seeded into Boyden Chambers following a 5 day pre-treatment as described in (E), n=6. (FIG. 7G) Model of autocrine and paracrine factors regulating mesenchymal and epithelial traits in HMLE cell lines (with associated cells surface markers CD44 and CD24) and, as indicated by our data, in a similar manner in primary MECs (with associated markers EpCAM and CD49f).

(FIG. 8A) Experimental design: secreted protein screening using cell culture supernatant of HMLE$^{24+}$ and HTwist cells. (FIG. 8B) Heat-map of 10% top differentially secreted proteins in HTwist compared to HMLE$^{24+}$ cells, based on consistent performance of each listed antibody for the three dilutions of cell culture supernatant (2×-10×-20× diluted). (FIG. 8C) ELISA: randomly selected proteins, comparison of relative difference in signal intensity on array and fold-difference in absolute protein levels by ELISA. (FIG. 8D) Experimental design: gene expression profiling, HMLE vs. HTwist and HSnail cells, as well as HMLE$^{24+}$ vs. MSP cells. Shown are heatmaps derived from gene set enrichment analysis (GSEA) of HMLE, HTwist and HSnail cell lines.

FIGS. 9A-9D. RT-PCR analysis. (FIG. 9A) BMP ligands in HMLE$^{24+}$, HTwist and MSP cells, L32 was loading control, n=3. (FIG. 9B) SFRP isoforms in HMLE$^{24+}$ and MSP cell lines, L32 was loading control, n=3. (FIG. 9C) Wnt ligands in HMLE$^{24+}$, HTwist and MSP cell lines, L32 was loading control, n=3. (FIG. 9D) Summary of differential expression of secreted proteins acting in Wnt, TGF-beta and BMP signaling in HMLE$^{24+}$, HTwist and MSP cell lines.

FIGS. 10A-10E. Inhibition of autocrine signaling in MSP and HTwist cell lines (FIG. 10A) Growth curves: proliferation assay (MTS) of MSP and HTwist cell lines treated daily with recombinant DKK1 (1 µg/ml), SFRP1 (1 µg/ml) or BMP4 protein (0.5 µg/ml), n=4. (FIG. 10B) Migration Assay: HTwist cells were seeded into Boyden Chambers in the presence of DKK1 (1 µg/ml), SFRP1 (14 ml), BMP4 protein (0.5 µg/ml) or in combination as indicated; *control vs. single treatment, $p<1\times10^{-5}$, **single vs. double-treatment, p<0.01, n=3. (FIG. 10C) Mammosphere assay: HTwist cells were treated daily during mammosphere formation (5 days) with proteins as described in (B); *control vs. single treatment, $p<1\times10^{-5}$, **single vs. double-treatment, p<0.01, n(mammospheres)/1000 cells, n=6, (FIG. 10D) Migration Assay: HTwist and MSP cells were seeded into Boyden Chambers in the presence of TGF-beta Receptor I inhibitors A83-01 and SB431542 (SB43, both at 10 µM). (FIG. 10E) Mammosphere Assay: HTwist and MSP were treated daily during mammosphere formation (5 days) with BMP4 (0.5 µg/ml), SB431542 (10 µM) or a combination of both, n(mammospheres)/1000 cells, n=6.

FIGS. 12A-12F. Concomitant stimulation of Wnt and TGF-beta pathways allows HMLE$^{24+}$ cells to enter into a mesenchymal and SC-like state. (FIG. 12A) RT-PCR: SFRP1, L32 was loading control, n=3; SFRP1 mRNA levels in HMLE$^{24+}$ stably expressing two hairpin-encoding vectors (shSFRP1a and -b) compared cells expressing a control hairpin targeting GFP (shGFP), HMLE$^{24+}$-shSFRP1b were used for iEMT experiments. (FIG. 12B) Flow cytometry: Expression of CD44 and CD24 cell-surface markers in HMLE, HMLE$^{24+}$-shGFP and -shSFRP1 cells. (FIG. 12C) Luciferase reporter assay: Smad transcriptional activity: cells were transfected with SBE4-luc reporter plasmid, firefly luciferase levels were normalized to pGL-SV40 renilla transfection control; cells were treated with recombinant TGF-beta 1 (5 ng/ml) for 30 min, n=3, (FIG. 12D) Bright field microscopy: images of untreated control cells (HMLE$^{24+}$-shGFP and -shSFRP1), one of two cultures of HMLE$^{24+}$-shGFP cells treated with TGF-beta 1 (5 ng/ml), and one of two cultures of HMLE$^{24+}$-shSFRP1 cells treated with the iEMT-cocktail: TGF-beta 1 (5 ng/ml), Wnt5a (250 ng/ml), anti-DKK1-(10 µg/ml) and anti-E-Cadherin-antibodies (1 µg/ml), (FIG. 12E) Luciferase reporter assay: indicated cells were transfected with smad (SBE4) and beta-catenin/TCF-LEF (TOPFLASH) reporter plasmids 8 passages after cessation of 14 day treatment as described in (D), n=3. (FIG. 12F) Growth curves: proliferation of indicated cell lines was monitored by the MTS assay for 3 days, 8 passages after cessation of 14 day treatment as described in (D), n=12.

(FIG. 13A) Expression of E-Cadherin in basal and luminal cells cultured on glass slides for 7 days after FACS. Arrows point to singly migrating cells outside epithelial islands that have lost E-Cadherin expression. DAPI was used to stain nuclei. (FIG. 13B) Expression of Zeb1 in luminal cells cultured on glass slides for 7 days after FACS. Arrows point to singly migrating cells outside epithelial islands that have acquired high nuclear expression of Zeb1.

(FIG. 14A) Growth curve: basal cells treated every 48 hrs with indicated factors, TGF-beta-type 1 receptor inhibitors A83-01 and SB431542 (10 µM), SFRP1 (1 µg/ml); cells were counted at indicated time points, n=2. (FIG. 14B) Growth curve: luminal cells treated every 48 hrs with indicated factors, TGF-beta 1 (5 ng/ml), Wnt5a (250 ng/ml), anti-DKK1-(10 µg/ml) and anti-E-Cadherin antibodies (1 µg/ml) or a combination of all factors (iEMT-II); cells were counted at indicated time points, n=2, (FIG. 14C) Microscopy images of basal cells treated as described in (A), at 4 days/before first passage. (FIG. 14D) Microscopy images of luminal cells treated as described in (B), at 4 days/before first passage.

DETAILED DESCRIPTION OF THE INVENTION

I. General

Figure 1A:
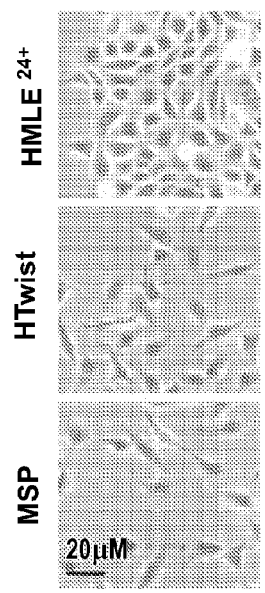
FIGS. 1A-1I. Characterization of a mesenchymal sub-population isolated from immortalized human mammary epithelial cells.

The present invention relates to the discovery that autocrine and paracrine signaling pathways play important roles in the induction of EMT and in the maintenance of a mesenchymal state and stem cell (SC)-like state associated with passage through an EMT. Modulation of these signaling pathways in accordance with certain embodiments of the invention provides means of inducing epithelial cells to undergo an EMT and/or of maintaining the mesenchymal and SC-like state of cells that have undergone an EMT. Modulation of these signaling pathways in accordance with certain other embodiments of the invention affords means of inhibiting epithelial cells from undergoing EMT and/or of inhibiting cells in a mesenchymal and SC-like state from maintaining that state.

As known in the art, epithelial cells have are closely attached by intercellular adhesion complexes (e.g., tight junctions, adherens junctions, desmosomes, gap junctions) in their lateral membranes, typically tend to grow in clusters or sheets, express characteristic markers such as E-cadherin, and have low or absent expression of mesenchymal markers such as N-cadherin, fibronectin, and vimentin. In some embodiments, of interest epithelial cells are $CD44^{low}$ and/or $CD24^{high}$. In contrast to epithelial cells, mesenchymal cells (e.g., cells that have undergone an EMT) lack intercellular junctions and frequently exhibit an elongated shape and a greater tendency to be present as single cells rather than in clusters. They express characteristic markers such as vimentin, fibronectin, N-cadherin, and α-smooth muscle actin, typically have low or absent expression of epithelial markers such as E-cadherin, α-catenin, β-catenin, and γ-catenin, and frequently have an increased ability to migrate as compared with epithelial cells. For example, mesenchymal cells may have at least a 5-fold greater ability to migrate, e.g., in vitro, as assessed a migration assay, than epithelial cells. In some embodiments, migration is increased by at least 10, 20, 50, 100-fold or more. Cells that exhibit the characteristic properties of mesenchymal cells may be referred herein to as being in a mesenchymal state or as exhibiting a mesenchymal phenotype.

Stem cells are undifferentiated cells that, among other characteristics, can give rise to various cell types. For the purposes of the present invention, a normal stem cell is defined as a normal (non-neoplastic) cell that is (a) relatively undifferentiated; (b) capable of generating daughter cells ("daughters") that are similarly undifferentiated; (c) capable of generating a lineage of such daughters that are able to reproduce themselves through a large number of successive growth-and-division cycles; and (d) capable of generating daughters that are able, under appropriate conditions, to enter into a program of differentiation that enables such cells to acquire the specialized traits of one or another functional tissue in the mammalian body. Cancer stem cells (CSCs) are defined functionally as those cells within a tumor that have the capacity to seed and generate secondary tumors, e.g., with high efficiency. Cancer stem cells thus possess characteristics associated with normal stem cells, such as self-renewal ability and the ability to give rise to multiple cell types found in a particular cancer. A cell that has properties of a normal stem cell or cancer stem cell may be referred to herein as a stem cell (SC)-like cell or as being in a stem cell (SC)-like state or as a "progenitor cell". In some embodiments an SC-like cell exhibits high levels of expression or localization of one or more characteristic markers or lacks expression of certain markers characteristic of differentiated cell types.

A variety of extracellular signals, including Wnt and TGF-beta ligands, Notch, Sonic Hedgehog and EGF, can induce EMTs in various cell types. In response to these contextual signals, the expression of certain pleiotropic transcription factors (TFs), such as Twist, Snail, Slug, Zeb1 and Zeb2, is induced. These TFs then act to orchestrate EMT programs. EMT can also result from causing epithelial cells to express TFs such as Twist, Snail, Slug, Zeb1, Zeb2, Goosecoid, FoxC2, and E47, e.g., through genetic engineering approaches. For purposes of the present invention, TFs that can induce EMT in at least some epithelial cell types are referred to as EMT TFs.

To characterize autocrine and paracrine mechanisms that induce EMT programs and subsequently maintain EMT-associated properties in normal and neoplastic cells, the inventors focused on molecules produced by such cells, such as growth factors and other signaling molecules operating extracellularly. Using an approach that included comparing secreted protein expression profiles and gene expression profiles between mammary epithelial cells (MECs) that had undergone an EMT and control cells that had not, autocrine and paracrine signaling pathways and molecules involved in induction of EMT and maintenance of the resulting mesenchymal and SC-like state were identified.

The term "autocrine signaling" is often used to refer to signaling in which a cell secretes a substance (an autocrine agent) that acts on that cell, leading to changes in the cell. Paracrine signaling typically refers to signaling in which a cell secretes a substance that acts on other cells in the environment of the cell, leading to changes in those cells. For example, a substance secreted by a cell in culture may act on other cells in the same culture vessel, and a substance secreted by a cell in vivo may act on other cells to which it can diffuse, typically in the same tissue or organ. Autocrine and paracrine agents may be proteins, small molecules, lipids, etc., and include a variety of different growth factors and hormones. Often they are secreted, although cell surface-bound molecules are also encompassed. Typically, an autocrine or paracrine agent exerts its effects by binding to receptors expressed by the cells on which the agent acts, leading to downstream signaling events whose details vary depending upon the particular agent, receptor, and/or signaling pathway involved. For purposes of the present invention, a paracrine signaling pathway is generally assumed to be "homotypic", i.e., involving signaling between cells of the same type, unless otherwise indicated. The terms "autocrine" and "paracrine" are used interchangeably herein, and autocrine and paracrine signaling pathways will often be collectively referred to herein as "autocrine signaling pathways".

Autocrine signaling pathways of interest herein include the TGF-β signaling pathway, the BMP signaling pathway, and Wnt signaling pathways. For purposes of facilitating understanding of the invention, these pathways and certain of their molecular components will be briefly described. One of skill in the art will be aware of additional details regarding these pathways. One of skill in the art will also readily be able to obtain sequences of the proteins involved in these pathways, and the genomic and mRNA sequences encoding them, from publicly available databases, such as those available at the National Center for Biotechnology Information (NCBI; ncbi.nlm.nih.gov), e.g., Gene, GenBank, Proteins, etc. For example, the Gene database provides sequence and functional information, which can be obtained, e.g., by searching on a name or Gene ID for a gene or protein of interest. Tables 1 and 2 provide gene names and Gene IDs for certain human genes of interest herein. One of skill in the art will readily be able to obtain the Gene IDs of corresponding genes in other organisms of interest. The TGF-β superamily of proteins plays important roles in a wide variety of processes. The TGF-β superfamily includes the TGFβs (TGFβ1, TGFβ2 and TGFβ3) and the BMPs (which include BMP2, BMP3a, BMP3b (GDF-10), BMP4, BMP5, BMP6, BMP7, BMP8a, BMP8b, BMP9(GDF-2), and BMP10, BMP11(GDF-11), BMP12(GDF-7), BMP13(GDF-6), BMP14(GDF-5), and BMP15, GDF-1, GDF-3, GDF-15, inhibin A, inhibin B, inhibin C and inhibin E. TGFβ superfamily ligands dimerize and initiate signaling by binding to and bringing together type I and type II receptor serine/threonine kinases on the cell surface. The receptor serine/threonine kinase family in humans includes 7 type I and 5 type II receptors that participate in TGF-β signaling. Type I receptors, also known as activin receptor-like kinases (ALKs), include ALK1, ALK2 (also known as ActR-I), ALK3(also known as BMPR-IA), ALK4(also known as ActR-IB), ALK5(also known as TGFβR-I), ALK6(also known as BMPR-IB), and ALK7. Type II receptors include TGFβR-II, BMPR-II, ACTR-IIA, ACTR-IIB, and AMHR-II. Different TGFβ superfamily members form complexes that contain different subsets of these receptors. For example, TGFβs form complexes with Type I receptors ALK1and/or ALK5and Type II receptor TGFβR-II, while BMPs form complexes with Type I receptors ALK2, ALK3and/or ALK6and Type II receptors BMPII-R, ACTR-IIA, and/or ACTR-IIB.

In both the TGFβand BMP signaling pathways, the type II receptors phosphorylate a type I receptor, which then phosphorylates and activates receptor-regulated SMADs (R-Smads), including Smad2 and Smad3 for TGFb signaling and Smads 1, 5, and 8 for BMP signaling. Activated R-Smads interact with the common partner Smad, Smad4. R-SMAD/Smad4 complexes translocate to the nucleus, where they act as transcription factors and participate in the regulation of target gene expression, a process that involves interaction with a variety of transcriptional cofactors that help confer target gene specificity.

BMPs are subject to regulation by a variety of endogenous secreted proteins that function as antagonists of BMP signaling by binding to BMPs in the extracellular space, thereby preventing the BMPs from binding to their receptors. "Endogenous" in this context refers to a molecule that is native to cells or organisms that contain and/or produce it and was not introduced directly or indirectly by the hand of man. For example a nucleic acid or protein that is naturally encoded by the genome of a cell or organism that produces it or in which it is found (i.e., not as a result of genetic engineering or other manipulation affecting the genome) is considered endogenous to the cell or organism. For purposes of the present invention, the term "endogenous" is often used to refer to molecules, e.g., RNA or proteins, that are encoded in the genome of cells or organisms of interest herein (e.g., cells or organisms in which it is desired to induce or inhibit an EMT) without requiring introduction into such cells or organisms (or their ancestors) of heterologous nucleic acids encoding such molecules. As will be evident herein, the term "endogenous" is typically employed for purposes of referring to certain molecules that are naturally produced by animals and play a role in regulating the TGFb, BMP, and/or Wnt pathways in the organisms that produce them. It will be appreciated that an "endogenous" molecule can be used in any of a wide variety of contexts in vitro and/or in vivo and can be produced or obtained using any suitable method (e.g., using recombinant DNA technology in any suitable cell type). The term "endogenous" is not intended to be limiting in these regards. Endogenous BMP inhibitor proteins include Gremlin, PRDC (protein related to Dan and Cerberus, also sometimes referred to as gremlin-2), Chordin, Chordin-like 1, Chordin-like 2, Crossveinless 2, Noggin, Dan, Cerberus, Coco, Twisted Gastrulation and Sclerostin, USAG-1, Tsukushi, Brorin, and Brorin-like among others. BMP antagonists contain a cysteine knot motif and can be divided into several subfamilies based on differences in this region. These include the CAN (Cerberus and Dan) family (8-membered ring), Twisted Gastrulation (9-membered ring), and Chordin and Noggin (10-membered ring) (Avsian-Kretchmer O. and Hsueh A. J., Mol. Endocrinol. 18, 1-12, 2004). BMP3 and BMP15 can function as antagonists of other BMPs in certain contexts.

TABLE 1

TGFs, BMPs, and Endogenous BMP Inhibitors

| Gene name (human genes) | Official Symbol | Gene ID (human genes_ |
|---|---|---|
| TGFβ1 | TGFB1 | 7040 |
| TGFβ2 | TGFB2 | 7042 |
| TGFβ3 | TGFB3 | 7043 |
| BMP2 | BMP2 | 650 |
| BMP4 | BMP4 | 652 |
| BMP3a | BMP3 | 651 |
| BMP3b (GDF-10), | GDF10 | 2662 |
| BMP5 | BMP5 | 653 |
| BMP6 | BMP6 | 654 |
| BMP7 | BMP7 | 655 |
| BMP8a | BMP8A | 353500 |
| BMP8b | BMP8B | 656 |
| BMP9 (GDF-2) | GDF2 | 2658 |
| BMP10 | BMP10 | 27302 |
| BMP11 (GDF-11) | BMP11 | 10220 |
| BMP12 (GDF-7) | GDF7 | 151449 |
| BMP13 (GDF-6) | GDF6 | 392255 |
| BMP14 (GDF-5) | GDF5 | 8200 |
| BMP15 | BMP15 | 9210 |
| Myostatin (GDF-8) | MSTN | 2660 |
| GDF-1 | GDF1 | 2657 |
| GDF-3 | GDF3 | 9573 |
| GDF-15 | GDF15 | 9518 |
| Inhibin A | INHBA | 3624 |
| Inhibin B | INHBB | 3625 |
| Inhibin C | INHBC | 3626 |
| Inhibin E | INHBE | 83729 |
| Gremlin | GREM1 | 26585 |
| PRDC (Gremlin-2) | GREM2 | 64388 |
| Chordin | CHRD | 8648 |
| Chordin-like 1 | CHRDL1 | 91851 |
| Chordin-like 2 | CHRDL2 | 25884 |
| Crossveinless 2 | BMPER | 608699 |
| Noggin | NOG | 9241 |
| Dan | NBL1 | 4681 |
| Cerberus | CER | 9350 |
| Coco | DAND5 | 199699 |
| Twisted Gastrulation | TWSG1 | 57045 |
| Sclerostin | SOST | 50964 |
| USAG-1 | SOSTDC1 | 25928 |
| Tsukushi | TSKU | 25987 |
| Brorin | VWC2 | 375567 |
| Brorin-like | VWC2L | 402117 |

Wnt signaling regulates a wide variety of cellular processes including cell fate determination, cell migration, and organogenesis. Wnts are secreted glycoproteins that bind to the extracellular domain of members of the Frizzled (Fz) receptor family. There are 19 human Wnt genes. Multiple transcript variants exist for some Wnts that, in some cases, encode different protein isoforms (e.g., Wnt16v1 and Wnt16v2). Co-receptors are involved in mediating Wnt signaling in many instances. For example, the low-density lipoprotein-related receptor protein 5/6 (LRP5/6) can act as a co-receptor for Fz. After binding of Wnt to the receptor complex, the Wnt-mediated signal is transduced to the cytoplasmic protein Dishevelled (Dsh). The Wnt signaling pathway divides into a number of distinct pathways at the level of Dsh. The canonical pathway involves accumulation of the adherens junction protein β-catenin and its translocation into the nucleus. In the absence of Wnt signaling, cytoplasmic β-catenin is degraded by a β-catenin destruction complex that includes glycogen synthase kinase 3 (GSK3) among other proteins. Phosphorylation of β-catenin by GSK3 targets it for ubiquitination and subsequent destruction. Binding of Wnt to its receptor complex leads to disruption of the β-catenin destruction complex, allowing β-catenin to accumulate. β-catenin translocates to the nucleus, where it regulates gene transcription by binding to a number of different partners and functioning as a transcriptional co-activator.

Non-canonical Wnt signaling pathways (also referred to as non β-catenin-dependent pathways) do not affect gene transcription through β-catenin but instead exert their effects through various other molecules, including monomeric Rho family GTPases (planar cell polarity pathway), Jun N-terminal kinase (INK), and through changes in intracellular calcium levels (Wnt/$Ca^{2+}$ pathway). In the Wnt/$Ca^{2+}$ pathway, Wnt/Fz signaling leads to release of intracellular $Ca^{2+}$ from the endoplasmic reticulum (ER) which activates a number of $Ca^{2+}$-sensitive proteins including protein kinase C (PKC) and calcium/calmodulin-dependent kinase II in a G-protein dependent manner.

Most Wnt proteins are believed to signal mainly via the canonical pathway, but a number of different Wnts, including Wnt4, Wnt5a, Wnt11, and Wnt16 signal primarily through non-canonical Wnt pathways. Wnt5a, for example, can activate the non-canonical pathway and stimulate intracellular $Ca^{2+}$ release but does not activate β-catenin stabilization. In contrast, Wnt11 can also act via the canonical pathway in certain contexts.

Wnt signaling is regulated by a variety of endogenous secreted proteins that bind to Wnts in the extracellular environment and inhibit their interaction with Fz and/or co-receptor(s) and/or that bind to the receptor/co-receptor, thereby acting as antagonists of Wnt signaling. These inhibitors include Dikkopf (DKK) family proteins (of which there are 4 in humans), soluble Frizzled-related proteins (SRFPs, of which there are 4 in humans: SFRP1, SFRP2, SFRP3 (the official name of which is frizzled-related protein (Frzb)), SFRP4, and SFRP5), and Wnt-inhibitor protein 1 (WIF1).

Considerable information regarding Wnts and Wnt signaling pathways is available at the following website: stanford.edu/~rnusse/wntwindow.html.

TABLE 2

Wnts and Endogenous Wnt Inhibitors

| Gene name (human genes) | Gene Symbol | Gene ID |
| --- | --- | --- |
| Wnt1 | WNT1 | 7471 |
| Wnt2 | WNT2 | 7472 |
| Wnt2B/13 | WNT2B | 7482 |
| Wnt3 | WNT3 | 7473 |
| Wnt3A | WNT3A | 89780 |
| Wnt4 | WNT4 | 54361 |
| Wnt5A | WNT5A | 7474 |
| Wnt5B | WNT5B | 81029 |
| Wnt6 | WNT6 | 7475 |
| Wnt7A | WNT7A | 7476 |
| Wnt7B | WNT7B | 7477 |
| Wnt8A | WNT8A | 7478 |
| Wnt8B | WNT8B | 7479 |
| Wnt9A (previously Wnt14) | WNT9A | 7483 |
| Wnt9B (previously Wnt15) | WNT9B | 7484 |
| Wnt10A | WNT10A | 80326 |
| Wnt10B | WNT10B | 7480 |
| Wnt11 | WNT11 | 7481 |
| Wnt16 | WNT16 | 51384 |
| SRFP1 | SFRP1 | 6422 |
| SRFP2 | SFRP2 | 6423 |
| FRZB | FRZB | 2487 |
| SFRP4 | SFRP4 | 6424 |
| SFRP5 | SFRP5 | 6425 |
| DKK1 | DKK1 | 22943 |
| DKK2 | DKK2 | 27123 |
| DKK3 | DKK3 | 27122 |
| DKK4 | DKK4 | 27121 |
| WIF1 | WIF1 | 11197 |

The invention encompasses the recognition that autocrine stimulation of the TGFβ pathway and of canonical and non-canonical Wnt pathways and restriction of BMP pathway signaling can collaborate in induction of EMT and in maintenance of the resulting mesenchymal and SC-like state. In accordance with certain embodiments of the invention, these pathways can be modulated using a variety of different approaches in order to enhance or inhibit EMT. For example, in some embodiments of the invention, the propensity of epithelial cells to undergo EMT is enhanced by mimicking the ways in which TGFβ and Wnt signaling pathways are stimulated and/or the ways in which BMP signaling is inhibited by endogenous substances to induce and/or maintain an EMT. In some embodiments, maintenance of a mesenchymal and/or SC-like state is facilitated by mimicking or reinforcing one or more autocrine signaling pathways that tend to maintain such cells in a mesenchymal and SC-like state and/or by providing an extracellular environment that is permissive for such signaling pathways to be operative. In some embodiments, epithelial cells are inhibited from undergoing EMT by interfering with one or more autocrine signaling pathways that may otherwise induce such cells to undergo EMT. In some embodiments, maintenance of a mesenchymal and/or SC-like state is inhibited by interrupting one or more autocrine signaling pathways that would otherwise maintain the SC-like state. Such approaches may be of use in methods of inducing the formation or differentiation of stem cells, e.g., for use in cell therapy. In some embodiments, induction or maintenance of EMT is facilitated by perturbing cell adhesion, e.g., by perturbing adherens junction formation or maintenance, in combination with stimulating TGF and Wnt pathways.

As described in further detail in the Examples, mammary cells in a mesenchymal and SC-like state were found to exhibit a variety of differences in the secretion of certain TGFβ, BMP, and Writ pathway ligands and endogenous antagonists as compared with mammary epithelial cells. These differences result in activation of TGF signaling, restriction of BMP signaling, disinhibition of canonical Wnt signaling, and activation of non-canonical Wnt signaling. These autocrine pathways collaborate in the induction of EMT and the maintenance of a mesenchymal state, both in normal and transformed cells. For example, it was discovered that cells that had undergone an EMT exhibited increased secretion of TGFβ1 as well as increased activity of a Smad-reporter plasmid and increased Smad2 phosphorylation (indicators of active TGF signaling), as compared with control cells that had not undergone an EMT. Thus, autocrine TGF-beta signaling was active in cells that had undergone an EMT as compared with control cells that had not. Furthermore, cells that had undergone an EMT were found to exhibit an extracellular signaling environment that restricted BMP signaling via (1) loss of BMP ligand production and (2) upregulation of secreted BMP antagonists. Without wishing to be bound by any theory, it is likely that restriction of BMP signaling creates an extracellular environment that is permissive for autocrine TGFβ signaling, thereby promoting induction of EMT and contributing to its maintenance.

It was also discovered that secretion of endogenous Wnt antagonists was downregulated in cells that had undergone an EMT as compared with control cells that had not undergone EMT. This downregulation was accompanied by increased canonical Wnt signaling (as evidenced, for example, by increased activity of a β-catenin/TCF-LEF reporter) that was dependent on the downregulation of the endogenous inhibitors. In addition, MECs that had undergone an EMT exhibited upregulation of most non-canonical Wnt ligands, accompanied by increased activity of associated downstream noncanonical signaling pathways (as evidenced, for example by activated protein kinase C (PKC) proteins and elevated phosphorylation of INK and its downstream target, c-Jun). In particular, secretion of endogenous Wnt inhibitors SFRP1 and DKK1 was decreased, while secretion of non-canonical Wnt proteins Wnt5a, Wnt16v1, and Wnt16v2 was increased in cells that had undergone EMT as compared with control cells.

The invention provides a variety of compositions and methods based at least in part on these discoveries. In some embodiments, an inventive method is performed in vitro (i.e., outside the body of an organism, e.g., in a cell culture vessel). In other embodiments, an inventive method is performed in vivo, e.g., by administering one or more compounds or compositions to a subject. In some embodiments, an inventive method is performed at least in part in vitro, e.g., cells are contacted with a composition in vitro, and cells are subsequently introduced into a subject, e.g., for experimental or therapeutic purposes. Thus it should be understood that unless otherwise indicated or otherwise evident from the context, any method of the invention comprises in vitro and in vivo embodiments, and any composition of the invention can be employed in vitro or in vivo. In some embodiments of the invention, an inventive method is applied to and/or uses mammary cells. Cells derived from mammary tissue are exemplified herein, but it will be understood that the invention, in various embodiments, encompasses cells derived from other tissues. It will be appreciated that certain details regarding the particular endogenous TGF, Wnt, and/or BMP ligands and/or antagonists operative in the autocrine TGF, Wnt, and/or BMP signaling pathways may differ in some other cell types. One of skill in the art could apply the profiling approaches described in the Examples to identify particular TGF, Wnt, and/or BMP ligands and/or antagonists that act to induce or inhibit EMT and/or that act to maintain or oppose maintenance of cells in a mesenchymal and SC-like state, or one could examine the proteins involved in these pathways in a cell type of interest to identify those that are differentially secreted and/or expressed. It will be understood that the term "ligand" refers to a chemical entity (e.g., a molecule or complex) that binds to another chemical entity (e.g., a molecule or complex), such as a cellular receptor. For example, a BMP ligand binds to a BMP receptor. The term "agonist" refers to a chemical entity (e.g., a molecule or a complex) that binds to a cellular receptor or receptor complex and triggers a response by the cell, e.g., stimulates a signaling pathway. An "antagonist" is a compound that blocks or otherwise antagonizes the activity of an agonist. For example, the antagonist may bind to the same receptor as an agonist (or to a co-receptor) but fail to elicit the response typically caused by the agonist (and such binding interferes with binding of the agonist), or the antagonist may bind to an agonist and prevent the agonist from binding to the receptor. Typically a ligand as referred to herein is an agonist unless otherwise specified or evident from the context.

It is also anticipated that inventive compositions and methods may be employed together with manipulations of other signaling pathways such as the Notch pathway, Hedgehog pathway, signaling via tyrosine kinase receptors such as Met, FGF, IGF, EGF, HGF, VEGF, and/or PDGF receptor family members, the NFkB pathway, hypoxia inducible factor (HIF) pathway, and/or microRNA regulatory pathways.

Epithelial cells (or other cells) for use in compositions and methods of the invention and/or to which methods of the invention may be applied, can be obtained from any of a wide variety of sources or, in the case of certain in vivo applications, may be present in a variety of tissues or organs. The cells may be primary cells, cells of a cell line, untransformed cells, transformed cells, genetically modified cells, or non-genetically modified cells, in various embodiments. For example, cells can be obtained from a human or other mammalian subject who may be the intended recipient of cell-based therapy, or a relative thereof, or an unrelated donor, may be obtained from discarded surgical or cellular samples from a subject, or from a propagated cell line. Mammary tissue is a useful source of cells. For example, primary human mammary epithelial cells (MECS) can be derived from fresh breast reduction tissue (reduction mammoplasty) by mechanical dissociation and, if desired, can be further purified by methods such as fluorescence activated cell sorting (FACS). Cultures of such primary MECS (or other epithelial cell types) can be genetically modified through introduction of various genetic elements, such as vectors (e.g., retroviral vectors) encoding the catalytic subunit of the human telomerase holoenzyme (hTERT) to generate immortalized cell lines. Such cell lines can be further genetically modified and transformed, e.g., through infection with vectors (e.g., retroviral vectors) encoding the Simian Virus 40 (SV40), Large T antigen, and the haRAS oncogene. In some embodiments, gene expression is reduced by genetically modifying cells to express a short hairpin RNA (shRNA), microRNA (miRNA) or miRNA precursor, miRNA sponge, etc., It will be appreciated that a variety of different oncogenes and/or tumor suppressor genes can be used to genetically modify cells. One of skill in the art would be aware of suitable vectors (e.g., viruses, plasmids) and genetic elements (e.g., regulatory elements such as promoters, enhancers, etc.) for transient or stable transfection of mammalian cells. In some embodiments, a regulatable (e.g., inducible and/or repressible) expression control element (e.g., promoter) is used to achieve regulatable expression of an RNA or protein of interest in cells. In another embodiment, activity is regulated by using a fusion protein comprising a protein of interest and a ligand-binding domain of a hormone receptor, e.g., a steroid hormone receptor such as the estrogen receptor, or a variant thereof that may selectively respond to a compound that is not normally present in the body of a subject such as a selective estrogen receptor modulator. Further, human and murine breast cancer-derived established cell lines, such as MCF7, MDA-MB-231 and 4T1 cells may be used. One of skill in the art would be aware of other cell lines (e.g., derived from other cancer types) that may be used in embodiments of the invention.

It will be appreciated that typically, inventive methods of inducing EMT generate cells that are in both a mesenchymal and SC-like state, and inventive methods of inhibiting EMT inhibit the generation of such cells. The term "and/or" in the phrase "mesenchymal and/or SC-like state" is used to indicate that the invention should not be considered so limiting. For example, phenotypes considered characteristic of mesenchymal cells or stem cells, such as those described above, may be of particular interest in certain embodiments of uses of the invention.

II. Inducing EMT or Maintaining a Mesenchymal and/or SC-like State

In some aspects, the invention provides compositions and methods useful for inducing epithelial cells to undergo an EMT or useful for maintaining cells in a mesenchymal and/or SC-like state. The invention provides a method of inducing EMT comprising subjecting epithelial cells to culture conditions in which at least three of the following processes occur: (a) stimulation of TGF-β pathway signaling; (b) stimulation of canonical Wnt pathway signaling; (c) stimulation of non-canonical Wnt pathway signaling; and (d) perturbation of cell adhesion. In some embodiments, epithelial cells are cultured under conditions in which all four of these processes occur. The invention further provides a method of maintaining cells in a mesenchymal and/or SC-like state, the method comprising subjecting cells in an SC-like state to culture conditions in which at least three of the following processes occur: (a) stimulation of TGF-β pathway signaling; (b) stimulation of canonical Wnt pathway signaling; (c) stimulation of non-canonical Wnt pathway signaling; and (d) perturbation of cell adhesion. In some embodiments, the cells are cultured under conditions in which all four of these processes occur. In some embodiments, the cells in a mesenchymal and/or SC-like state are derived from epithelial cells that have undergone an EMT. In some embodiments, the cells were induced to undergo an EMT according to a method of the present invention. In some embodiments of various aspects of the invention, stimulating a non-canonical Wnt pathway comprises stimulating the Wnt/$Ca^{2+}$ pathway or JNK/c-Jun pathway.

The invention encompasses the recognition that BMP signaling can operate to inhibit the ability of a TGFβ agonist to induce epithelial cells to undergo EMT and/or to maintain cells in a mesenchymal and SC-like state. In some embodiments of the invention, stimulating TGF-β pathway signaling comprises providing an extracellular environment that is permissive for TGF-β signaling. In some embodiments, an environment that is permissive for TGF-β signaling is one in which BMP pathway signaling is inhibited. Accordingly, the invention provides methods of enhancing the ability of a TGFβ agonist to induce an epithelial cell to undergo EMT, wherein the cell is in an environment in which it is exposed to a TGF agonist, the methods comprising modifying the environment of the cell so that BMP pathway signaling is inhibited. The invention further provides methods of enhancing the ability of a TGFβ agonist to maintain a cell in a mesenchymal and/or SC like state, the methods comprising exposing a cell to an environment that contains a TGFβ agonist and in which BMP pathway signaling is inhibited. In some embodiments, inhibiting BMP pathway signaling comprises downregulating synthesis of one or more endogenous BMP ligands that would otherwise stimulate BMP signaling or providing a BMP antagonist.

In some aspects, the invention relates to the recognition that secretion of endogenous Wnt antagonists by cells may inhibit epithelial cells from undergoing EMT. In some embodiments of the invention, stimulation of Wnt pathway signaling comprises disinhibiting Wnt pathway signaling by inhibiting one or more endogenous Wnt inhibitors. Inhibiting Wnt antagonists can disinhibit Wnt signaling, thereby promoting EMT and/or promoting maintenance of a mesenchymal and/or SC-like state. In one aspect, the invention provides a method of inducing a cell to undergo an EMT, wherein the cell is a member of a population of cells, and wherein at least some cells in the population secrete an endogenous Wnt antagonist, the method comprising inhibiting the Wnt antagonist secreted by cells in the population. In another aspect, the invention provides a method of inducing a cell to undergo an EMT, wherein the cell is a member of a population of cells, and wherein at least some cells in the population secrete a Wnt antagonist, the method comprising contacting the cells with an agent that inhibits the Wnt antagonist. In some embodiments of the invention, the method may comprise inhibiting an SFRP family member and a DKK family member.

In some embodiments, the methods comprise contacting epithelial cells with compounds that stimulate or inhibit one or more of the afore-mentioned pathways or processes. For example, the invention provides a method of inducing EMT comprising contacting epithelial cells with a composition comprising one or more compounds selected from each of at least three of the following groups: (a) compounds that stimulate TGF-beta pathway signaling; (b) compounds that stimulate canonical Wnt pathway signaling; (c) compounds that stimulate non-canonical Wnt pathway signaling; and (d) compounds that perturb cell adhesion. In some embodiments, the composition comprises one or more compounds from each of the afore-mentioned four groups. A composition useful for inducing EMT and/or for maintaining cells in a mesenchymal and/or SC-like state may be referred to herein as an "EMT induction composition" or "EMT induction cocktail". An EMT induction composition of the invention may further comprise a compound that inhibits BMP signaling. Exemplary compounds are discussed further below.

In some aspects, the invention provides methods for inducing a mesenchymal and/or SC-like state, the methods comprising contacting epithelial cells with an EMT induction composition of the invention. In some embodiments, cells are contacted for a sufficient time such that the cells undergo an EMT and subsequently maintain a mesenchymal and SC-like state for a prolonged period of time without requiring the addition of any of the components of the EMT-induction composition to the culture medium. In some embodiments, a prolonged period of time refers to at least 10 passages. For purposes of the present invention, a state that persists for at least 10 passages under a given set of conditions is considered "stable". In some embodiments, a prolonged period of time refers to at least 12 passages (about 36 population doublings), 15, 20, 25, or more passages. In some embodiments, epithelial cells are contacted with an EMT induction composition for at least about 14 days. Of course cells could be contacted with the EMT induction composition for longer time periods, e.g., about 20, 25, or 30 days, or longer. One skilled in the art would appreciate that the minimum time required for stable induction of EMT may depend, for example, on the particular components of the EMT induction cocktail, the concentrations at which they are used, and the epithelial cell type. Furthermore, one of skill in the art could, if desired, readily vary the particular components and concentrations to optimize the methods for a particular epithelial cell type.

In some aspects, the invention provides a method of promoting the ability of a TGFβ agonist to induce an epithelial cell to undergo EMT, the method comprising: (a) providing a composition comprising an epithelial cell and a TGFβ agonist; and (b) contacting the cell with a compound that inhibits BMP signaling. The invention further provides a method of promoting the ability of a TGFβ agonist to maintain a cell in a mesenchymal and/or SC-like state, the method comprising: (a) providing a composition comprising a mesenchymal cell and a TGFβ agonist; and (b) contacting the cell with a compound that inhibits BMP signaling.

In some embodiments, cells that have been contacted with an EMT induction cocktail of the invention have at least a 5-fold greater ability to migrate or invade, e.g., in vitro, as assessed a migration or invasion assay, than control cells that have not been contacted with the EMT induction cocktail. In some embodiments, migration and/or invasion is increased by at least 10, 20, 50, 100-fold or more. The effect of a compound or composition on migration or invasion can be assessed using any method known in the art. See, e.g., Valster A, et al., Methods, 37(2):208-15, 2005, and Examples. Many such assays involve a chamber (e.g., a Boyden chamber) consisting of two medium-filled compartments separated by a filter, which may be coated with various components, e.g., ECM components (e.g., Matrigel), in order to assess capacity to invade through such components. A cell suspension is placed in one of the compartments, and incubated. Cells migrate from that compartment through the filter pores to the other side of the filter and are then quantified. If desired, test substances can be included in the medium in either compartment, e.g., to assess the effect of such substances on migration/invasion and/or cells can be exposed to test substances prior to introducing the cells into the chamber.

In some embodiments, cells that have been contacted with an EMT induction cocktail of the invention have increased self-renewal ability as compared with control cells not contacted with the EMT induction cocktail. For example, cells contacted with an EMT induction cocktail may have at least a 2-fold or at least a 5-fold greater self-renewal ability than control cells that have not been contacted with the EMT induction cocktail. In some embodiments, self-renewal ability is increased by at least 10, 20, 50, 100-fold or more. The effect of a compound or composition on self-renewal ability can be assessed using any method known in the art. For example, inhibition of primary or secondary mammosphere formation or tumorsphere formation can be assessed.

In some embodiments, transformed cells that have been contacted with an EMT induction cocktail of the invention have at least a 2-fold or at least a 5-fold greater ability to initiate tumors than control cells that have not been contacted with the EMT induction cocktail. In some embodiments, tumor-initiating ability is increased by at least 10, 20, 50, 100-fold or more. Tumor-initiating ability may be assessed using methods known in the art, e.g., by introducing cells into a non-human animal host, e.g., an immunocompromised non-human host. Typically the host is a mammal, e.g., a rodent, e.g., a mouse or rat. Immunocompromised rodent strains are known in the art. For example, SCID, NOD-SCID, nude mouse or rat could be used. In another embodiment, an animal whose thymus gland has been surgically removed or rendered nonfunctional e.g., through a means such as radiation or chemical agents, or whose immune system has been suppressed by drugs or genetic manipulations (e.g., knockdown or knockout of one or more genes that encode molecules important in immune system development and/or function), is used. For example, a Rag1 and/or Rag2 knockout animal could be used.

Without wishing to be bound by any theory, methods of the present invention for inducing and/or maintaining EMT may offer a number of advantages. In some embodiments, inventive methods of inducing and/or maintaining an EMT resemble those that occur in normal and/or pathological states in vivo and provide a physiologically relevant context for the study of normal and/or pathological EMT or for the identification or characterization of additional agents that may alter (e.g., inhibit or promote) EMT. In some embodiments, inventive methods allow the induction and/or maintenance of an EMT without requiring genetic modification of epithelial cells. Avoiding genetic modification may be desirable, e.g., when EMT is used to generate progenitor cells that will subsequently be used for cell-based therapy, as described further below.

III. Inhibiting Induction of EMT and/or Maintenance of Mesenchymal and/or SC-like State In some aspects, the invention provides compositions and methods useful for inhibiting induction of EMT and/or inhibiting maintenance by cells of a mesenchymal and/or SC-like state. In some embodiments, the inventive methods involve disrupting (interfering with) one or more signaling pathways that would otherwise operate to induce epithelial cells to undergo EMT and/or to maintain cells in a mesenchymal and/or SC-like state.

In one aspect, the invention provides a method of inhibiting epithelial cells from undergoing an EMT, the method comprising inhibiting the cell's canonical and/or non-canonical Wnt pathway signaling pathways and/or stimulating the cell's BMP pathway signaling pathway. In some embodiments, the method comprises inhibiting one or more canonical and/or noncanonical Wnt signaling pathways and stimulating the BMP signaling pathway of the cell. In some embodiments inhibiting Wnt pathways and stimulating BMP signaling has additive or synergistic effects. The invention further provides a method of inhibiting EMT comprising contacting epithelial cells with one or more compounds that inhibit canonical and/or non-canonical Wnt pathway signaling and/or one or more compounds that stimulate BMP pathway signaling. In some embodiments of the various aspects of the invention, inhibiting a non-canonical Wnt pathway comprises inhibiting the Wnt/Ca$^{2+}$ pathway or the JNK/c-Jun pathway. In some embodiments, the inventive methods are useful in situations in which the TGFβ pathway is stimulated (e.g., in the presence of a TGFb agonist), wherein the stimulation of the TGFβ pathway would otherwise promote EMT. In some embodiments, the method further comprises inhibiting the TGFβ signaling pathway of the cell. Without wishing to be bound by theory, the discovery that restricting BMP signaling provides an environment that is permissive for TGF signaling suggests that stimulating BMP signaling would limit the ability of TGF ligands to induce an EMT and/or to maintain cells in a mesenchymal and/or SC-like state. In some embodiments, the method comprises contacting the epithelial cell with a Wnt inhibitor and a BMP agonist, whereby EMT is inhibited.

The invention further provides a method of inhibiting cells from maintaining a mesenchymal and/or SC-like state, the method comprising inhibiting the cells' canonical and/or non-canonical Wnt pathway signaling pathways and/or stimulating the cells' BMP pathway signaling pathway. The invention further provides a method of inhibiting cells from maintaining a mesenchymal and/or SC-like state, the method comprising contacting the cells with one or more compounds that inhibit canonical and/or non-canonical Wnt pathway signaling and/or one or more compounds that stimulate BMP pathway signaling. In some embodiments, the inventive methods are useful in situations in which the TGFβ pathway is stimulated, wherein the stimulation of the TGFβ pathway would otherwise contribute to maintaining cells in a mesenchymal and/or SC-like state. Thus, in some embodiments, the inventive methods are applied to cells in an environment in which TGFb signaling is stimulated (e.g., in the presence of a TGFb agonist), wherein stimulation of the TGFb signaling pathway would otherwise operate to maintain cells in a mesenchymal and/or SC-like state.

In another aspect, the invention provides a method of inhibiting epithelial cells from undergoing an EMT, the method comprising contacting epithelial cells with a composition comprising one or more compounds selected from each of at least two of the following groups: (a) compounds that inhibit TGF-beta pathway signaling; (b) compounds that inhibit canonical and/or non-canonical Wnt pathway signaling; (c) compounds that stimulate BMP pathway signaling. In some embodiments, the composition comprises one or more compounds from each of the afore-mentioned three groups. A composition useful for inhibiting EMT and/or for inhibiting maintenance of a mesenchymal and/or SC-like state may be referred to herein as an "EMT inhibition composition" or "EMT inhibition cocktail". In some embodiments, the composition comprises at least one compound that inhibits canonical and non-canonical Wnt pathway signaling. In some embodiments, the composition comprises at least one compound that inhibits canonical and non-canonical Wnt pathway signaling and at least one compound that stimulates BMP pathway signaling. In some embodiments, the compound that stimulates BMP signaling in any of the inventive compositions or methods comprises a BMP agonist. In some embodiments, a compound that stimulates BMP signaling in any of the inventive compositions or methods comprises a compound that disinhibits BMP signaling, e.g., by inhibiting an endogenous BMP antagonist. Exemplary compounds are discussed further below.

In some embodiments, epithelial cells are contacted with an EMT inhibition composition thereof for a time period ranging from about 12 hours to about 10 days. In some embodiments, epithelial cells are contacted with an EMT inhibition composition for at least about 10 days. Of course cells could be contacted with the composition for longer time periods, e.g., about 15, 20, 25, or 30 days, or longer, e.g., for as long as it is desired to inhibit EMT and/or inhibit maintenance of a mesenchymal and/or SC-like state, e.g., in cells that have undergone an EMT. One skilled in the art would appreciate that the particular components of the EMT inhibition composition, and concentrations at which they are used, can be varied. If desired, one of skill in the art could readily vary the particular components and concentrations to optimize the methods for a particular cell type.

In some aspects, the invention provides a method of reducing the ability of a TGFβ agonist to induce epithelial cells to undergo EMT, the method comprising: (a) providing a composition comprising epithelial cells and a TGFβ agonist; and (b) contacting the cell with a compound that stimulates BMP signaling and/or a compound that inhibits canonical or non-canonical Wnt signaling. In some aspects, the invention provides a method of reducing the ability of a TGFβ agonist to promote maintenance by cells of a mesenchymal and/or SC-like state, the method comprising: (a) providing a composition comprising cells in a mesenchymal and/or SC-like state and a TGFβ agonist; and (b) contacting the cells with a compound that stimulates BMP signaling and/or a compound that inhibits canonical or non-canonical Wnt signaling.

The invention further provides a method of enhancing the ability of a TGFβ inhibitor to inhibit epithelial cells from undergoing EMT, the method comprising: (a) providing a composition comprising epithelial cells and a TGFβ inhibitor; and (b) contacting the cell with a compound that stimulates BMP signaling and/or a compound that inhibits canonical or non-canonical Wnt signaling. The invention further provides a method of enhancing the ability of a TGF inhibitor to inhibit maintenance by cells of a mesenchymal and/or SC like state, the method comprising: (a) providing a composition comprising an epithelial cell and a TGF inhibitor; and (b) contacting the cell with a compound that stimulates BMP signaling and/or a compound that inhibits canonical or non-canonical Wnt signaling. In some embodiments, the cell is contacted with at least one compound that stimulates BMP signaling and at least one compound that inhibits canonical or non-canonical Wnt signaling. In some embodiments, the contacting the cell with a compound that stimulates BMP signaling and/or a compound that inhibits canonical or non-canonical Wnt signaling allows the use of a lower amount or concentration of a TGF inhibitor while still achieving the same degree of inhibition of EMT and/or inhibition of mesenchymal and/or SC-like properties.

In some embodiments, cells that have been contacted with one or more components of an EMT inhibition composition of the invention have a reduced ability to migrate or invade, e.g., in vitro, as assessed using a migration or invasion assay, than control cells that have not been contacted with the EMT inhibition cocktail. In some embodiments, migration and/or invasion is reduced by at least 10, 20, 50, 100-fold or more in cells that have been contacted with one or more components of an inventive EMT inhibition composition.

In some embodiments, cells that have been contacted with one or more components an EMT inhibition composition of the invention have reduced self-renewal capacity than control cells that have not been so contacted. In some embodiments, self-renewal is inhibited by at least 10%, 20%, 30%, 40%, 50%, 60%, 70%, 80%, 90%, or more in cells contacted with one or more components of an inventive EMT inhibition composition.

In some embodiments, transformed cells that have been contacted with an EMT inhibition cocktail of the invention have a reduce ability to initiate tumors than control cells that have not been contacted with the EMT inhibition cocktail. For example, tumor initiating ability of transformed cells contacted with an EMT inhibition composition may be reduced by at least 20%, 30%, 40%, 50%, or more, e.g., at least 2-fold, 5-fold, 10-fold or more, as compared with control cells that have not been contacted with the EMT inhibition cocktail.

In some embodiments, tumorigenic cells contacted with an EMT inhibition cocktail of the invention have a reduced ability to metastasize as compared with control cells that have not been contacted with an EMT inhibition composition. For example, the ability to metastasize may be reduced by at least 20%, 30%, 40%, 50%, or more, e.g., at least 2-fold, 5-fold, 10-fold, relative to control cells that have not been contacted with the EMT inhibition composition. Metastasis or tumor formation can be measured using in vivo metastasis assays as known in the art. For example, to measure metastasis, tumorigenic cells can be implanted into an animal host (e.g., in an orthotopic location or subcutaneously), and the number of metastatic foci at a second location (e.g., liver, lung) can be assessed after a suitable time period. The number of foci can be normalized based on primary tumor weight. To measure tumor forming ability, tumorigenic cells can be implanted into an animal host (e.g., in an orthotopic location or subcutaneously), and the number of tumors that form can be assessed after a suitable time period.

In some embodiments, methods of inhibiting EMT are of use to promote exit from a mesenchymal and/or SC-like state, e.g., in the directed differentiation of stem cells to cell types of interest for use in cell-based therapy.

IV. Compounds for Use in Modulating TGF Beta, BMP, or Wnt Signaling Pathways or Perturbing Cell Adhesion In general, any of a variety of suitable compounds (also referred to as "agents") may be used to modulate the TGFβ, Wnt, and/or BMP signaling pathway in accordance with the invention. Compounds can comprise, e.g., proteins (which term is used interchangeably with "polypeptide" herein), small molecules, nucleic acids, etc. A "small molecule" as used herein, is an organic molecule that is less than about 2 kilodaltons (KDa) in mass. In some embodiments, the small molecule is less than about 1.5 KDa, or less than about 1 KDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups. Polypeptides of interest herein often contain standard amino acids (the 20 L-amino acids that are most commonly found in nature in proteins). However, other amino acids and/or amino acid analogs known in the art (e.g., found in nature or not naturally occurring) can be used in certain embodiments of the invention. One or more of the amino acids in a polypeptide (e.g., at the N- or C-terminus or in a side chain) may be modified, for example, by addition, e.g., covalent linkage, of a moiety such as an alkyl group, carbohydrate group, a phosphate group, a lipid, a linker, etc. Polypeptides may be modified, e.g., by addition of a moiety such as polyethylene glycol (PEGylation), e.g., in order to increase stability, half-life, or desirably modify other properties of the polypeptide. In some embodiments a nucleic acid (which term is used interchangeably with "polynucleotide") comprises standard nucleotides (abbreviated A, G, C, T, U). In other embodiments a nucleic acid comprises one or more non-standard nucleotides. In some embodiments, one or more nucleotides are non-naturally occurring nucleotides or nucleotide analogs. A nucleic acid can comprise chemically or biologically modified bases (for example, methylated bases), modified sugars (2'-fluororibose, arabinose, or hexose), modified phosphate groups (for example, phosphorothioates or 5'-N-phosphoramidite linkages), locked nucleic acids, or morpholinos. In some embodiments, a nucleic acid comprises nucleosides that are linked by phosphodiester bonds. In some embodiments, at least some nucleosides are linked by a non-phosphodiester bond. A nucleic acid can be single-stranded, double-stranded, or partially double-stranded. An at least partially double-stranded nucleic acid can have one or more overhangs, e.g., 5' and/or 3' overhang(s). Nucleic acid modifications (e.g., nucleoside and/or backbone modifications), non-standard nucleotides, delivery vehicles and approaches, etc., known in the art as being useful in the context of RNA interference (RNAi), aptamer, or antisense-based molecules for research or therapeutic purposes are contemplated for use in various embodiments of the instant invention. See, e.g., Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008. "Antibody" encompasses immunoglobulins and derivatives thereof containing an immunoglobulin domain capable of binding to an antigen. An antibody can originate from a mammalian or avian species, e.g., human, rodent (e.g., mouse, rabbit), goat, chicken, etc., or can be generated ex vivo using a technique such as phage display. Antibodies are of use in certain embodiments of the invention, Antibodies include members of the various immunoglobulin classes, e.g., IgG, IgM, IgA, IgD, IgE, or subclasses thereof such as IgG1, IgG2, etc., and, in various embodiments, encompasses antibody fragments or molecules such as an Fab', F(ab')2, scFv (single-chain variable) that retains an antigen binding site and encompasses recombinant molecules comprising one or more variable domains (VH or VL). An antibody can be monovalent, bivalent or multivalent in various embodiments. The antibody may be a chimeric or "humanized" antibody. An antibody may be polyclonal or monoclonal, though monoclonal antibodies may be preferred. RNA interference (RNAi) may be employed to inhibit expression in eukaryotic cells, e.g., vertebrate cells, in a variety of ways as known in the art. As used herein, the term "RNAi agent" encompasses nucleic acids that can be used to achieve RNAi in eukaryotic cells. Exemplary RNAi agents are short interfering RNA (siRNA) and short hairpin RNA (shRNA). As known in the art, siRNAs typically comprise two separate nucleic acid strands that are hybridized to each other to form a duplex. They can be synthesized in vitro, e.g., using standard nucleic acid synthesis techniques or by cleavage of a longer dsRNA, e.g., by an RNase III or RNase III-like enzyme such as Dicer. In certain embodiments an siRNA or shRNA comprises a duplex portion about 15-29 nucleotides (nt) long, e.g., between 17-25 nt long, e.g., between 19-23 nt long, wherein either or both strands optionally has a 3' overhang of 1-5 nucleotides long (e.g., 2 nucleotides), which may be composed of deoxyribonucleotides. In some embodiments, the strands are perfectly complementary within the duplex portion, while in other embodiments, the duplex portion could contain one or more mismatched nucleotide pairs or bulges. In some embodiments, each strand of an siRNA is between 15-29 nucleotides in length, e.g., between 19-25 nt long, e.g., 21-23 nt long, shRNA comprise a single nucleic acid strand that contains two complementary portions separated by a predominantly non-self-complementary region. The complementary portions hybridize to form a duplex structure and the non-self-complementary region forms a loop connecting the 3' end of one strand of the duplex and the 5' end of the other strand, shRNAs can undergo intracellular processing to generate siRNAs. RNAi agents also include microRNA (miRNA) and miRNA precursors. As used herein, "miRNA" and "miRNA precursor" encompasses naturally occurring and artificially designed nucleic acids that function in an analogous manner to naturally occurring miRNAs. In certain embodiments an RNAi agent is a vector that comprises a template for transcription of an siRNA (e.g., as two separate strands that can hybridize to each other), shRNA, or microRNA precursor. Such vectors can be used to introduce the template into vertebrate cells, e.g., mammalian cells, and result in transient or stable expression of the siRNA, shRNA, or miRNA precursor.

In some embodiments of the invention, a compound comprises a naturally occurring polypeptide. For purposes of the present invention, a polypeptide is said to be "naturally occurring" if it has the amino acid sequence of a polypeptide found in nature. For example, a recombinantly produced polypeptide identical in sequence to a polypeptide found in nature is said to be a "naturally occurring" polypeptide. Naturally occurring agonists of TGFb, Wnt, and/or BMP receptors can be used to stimulate signaling via the TGFb, Wnt, and/or BMP pathways, respectively, in certain embodiments of the invention. Naturally occurring antagonists of Wnt and/or BMP proteins can be used to inhibit signaling via the Wnt, and/or BMP pathways, respectively, in certain embodiments of the invention.

In some embodiments, a compound that stimulates a signaling pathway comprises a protease that processes an inactive autocrine agent and thereby converts it into an active form or releases an autocrine agent that is bound to a cell surface or to the extracellular matrix or cleaves and inactivates an endogenous inhibitor of the pathway. For example, it will be appreciated that mature TGF-βs may be secreted by cells in a latent dimeric form, in which latency is caused by the amino-terminal prodomain LAP (latency-associated protein), and may be bound to latent TGF-β1 binding protein (LTBP), which binds to the extracellular matrix. In some embodiments, a protease that participates in removal of LAP and/or release of mature TGF-βs from the ECM stimulates TGFb signaling.

The term "inhibitor" encompasses compounds that inhibit expression and/or inhibit one or more activities of a molecule or complex of interest (the "target"). For example, a compound is an "inhibitor" of a target if one or more activities of the target is reduced in the presence of the compound, or as a consequence of its use, as compared with in the absence of the compound, and/or if the level or amount of the target is reduced in the presence of the compound, or as a consequence of its use, as compared with in the absence of the compound. In certain embodiments, inhibitors act directly on their target in that they physically interact with it. In other embodiments, inhibitors act indirectly, e.g., by inhibiting a second molecule that is needed for synthesis or activity of the target. In some embodiments, an inhibitor is an antagonist. Methods of inhibiting encompass methods that result in a decreased amount of a target and methods that interfere with one or more functions of a target. In some embodiments, a target is inhibited by inhibiting or interfering with its expression or post-translational processing, so that a decreased amount of functional target is produced. As used herein, "expression" encompasses the cellular processes involved in producing a polypeptide and include transcription, mRNA processing and transport (in the case of eukaryotic cells), and mRNA translation. A variety of methods useful for inhibiting or interfering with expression can be applied in embodiments of the present invention. In general, such methods result in decreased synthesis of a mRNA and/or polypeptide and as a result, a reduction in the total level of activity present. Other means of inhibition include interfering with proper localization, secretion, or co- or post-translational processing, or promoting increased degradation. Methods of inhibiting activity can include binding to a target or to a receptor or co-receptor for the target and thereby blocking the target from interacting with its receptor(s) or with other molecule(s) needed for activity of the target. Other means of inhibiting include binding to an active site or catalytic residue or substrate binding site of an enzyme, blocking dimerization or other protein-protein interactions, etc.

In some embodiments, an inhibitor of a signaling pathway comprises a protease that degrades an agonist of the pathway. In some embodiments, an inhibitor of a signaling pathway comprises an agent that acts via RNA interference (an "RNAi agent"), e.g., an siRNA or shRNA, to inhibit expression of an agonist of the pathway or inhibits production of a receptor that functions in the pathway). In some embodiments, an inhibitor of a signaling pathway comprises an agent that acts via an antisense mechanism to inhibit expression of an agonist of the pathway or inhibits production of a receptor that functions in the pathway). In some embodiments, an inhibitor of a signaling pathway comprises an antibody or aptamer that binds to and inhibits an agonist of the pathway or binds to and inhibits a receptor that functions in the pathway. Additional details regarding certain compounds of use in the invention are provided below. One of skill in the art will be aware of other compounds that can be used in the practice of the invention.

TGFb signaling may be stimulated using a naturally occurring TGFb polypeptide (TGFb1, TGFb2, or TGFb3). In other embodiments a small molecule or peptide is used to stimulate TGF signaling. For example, PCT/US2008/011648 (WO/2009/051660) discloses small molecules reported to activate TGF beta signaling.

TGFb signaling may be inhibited using any of a variety of compounds and approaches. In some embodiments, a TGF beta inhibitor comprises a polypeptide comprising a soluble portion of a type II TGF-beta receptor. In some embodiments, said polypeptide comprises a heterologous portion, e.g., an Fc domain, e.g., soluble type II TGF-beta receptor:Fc fusion protein. In another embodiment, a TGFbeta inhibitor comprises an antibody that binds to TGFbeta, e.g., TGFbeta, and prevents the TGF beta from interacting with its receptors. For example, CAT-192 and GC1008 are monoclonal antibodies that bind to active TGFbeta 1. In another embodiment, a TGFbeta inhibitor comprises an antibody that binds to a TGF-beta receptor and prevents TGF beta from binding thereto. In another embodiment, a nucleic acid such as an RNAi agent or antisense agent is used to inhibit TGFb signaling, e.g., to inhibit production of TGF or of a TGFbeta receptor by cells. For example, AP12009 is a TGF-b2 inhibitor which is an antisense agent. In other embodiments, a TGF beta inhibitor is a small molecule. For example, the small molecule may bind to and inhibit a TGF beta receptor, e.g., a Type I TGF beta receptor such as ALK1 or ALK5, and/or a Type II TGF beta receptor. For example, such compounds may interfere with ATP- or substrate-binding sites of the TGF beta type I receptor kinase. A number of such molecules are known in the art. Examples include, e.g., A83-01, SB431542, SM-16 and LY2109761 (a dual Type I and II receptor inhibitor), and structurally related compounds. One of skill in the art would be aware of other TGFb inhibitors.

BMP signaling may be inhibited using endogenous BMP antagonists or functional variants or fragments thereof. Other compounds that inhibit BMP signaling may be used in certain embodiments of the invention. For example, dorsomorphin and dorsomorphin derivatives such as LDN-193189 are small molecules that inhibit BMP signaling (see, e.g., Cuny, G D, et al., Bioorganic & Medicinal Chemistry Letters, 18: 4388-4392, 2008, and references therein, and PCT/US2009/001606 (WO 2009/114180)). In other embodiments, expression of one or more BMP ligands and/or Type I or Type II BMPreceptors is inhibited using an RNAi or antisense approach. For example, shRNAs or siRNAs may be used to inhibit ALK2, ALK3, ALK6, BMPII-R, ACTR-IIA, and/or ACTR-IIB.

BMP signaling may be stimulated using BMP proteins (e.g., BMP2, BMP4, or functional variants thereof. BMP signaling may also be activated using, e.g., small molecules such as the amiloride derivative phenamil, which reportedly stimulates BMP signaling potentially by a mechanism involving upregulation of Tribble3 (Park K W, Mol. Cell. Biol. 29: 3905-3914, 2009). It would be reasonable to expect that derivatives of phenamil having similar effects could be synthesized. In other embodiments, BMP signaling is stimulated using inhibitors of endogenous BMP antagonists. For example, antibodies to such BMP antagonists can be used. In one embodiment, an antibody to Chordin-like 2 or Gremlin is used. In other embodiments, synthesis of one or more naturally occurring BMP antagonists is inhibited using RNAi or an antisense molecule.

Wnt signaling may be inhibited using a variety of approaches. In accordance with certain embodiments of the invention it may be desirable to inhibit multiple Wnt family members. In some embodiments, a Wnt inhibition composition contains a compound capable of inhibiting multiple Wnt proteins, e.g., ranging between 2 Wnts, up to the total complement of Wnt proteins expressed by a cell or organism of interest. In some embodiments, Wnt signaling is inhibited using one or more endogenous Wnt antagonists such as an SFRP or DKK protein. For example, SFRP1 may be used. In some embodiments, at least one SFRP family member and at least one DKK family member are used, e.g., SFRP1 and DKK1.

Other approaches to inhibiting Wnt include inhibiting proteins involved in the co- or post-translational processing (e.g., glycosylation, lipidation), secretion, and/or destruction of multiple Wnts or that otherwise interact with multiple Wnts to promote their activity. For example, porcupine is an endoplasmic-reticulum-resident acyltransferase involved in lipid modification of Wnts, which promotes and/or is necessary for their activity. Inhibitors of porcupine would thus inhibit multiple Wnt proteins and pathways. See, e.g., Chen B, et al., Nat Chem Biol. 5(2):100-7, 2009, for description of certain small molecules that inhibit porcupine. Axin functions as a negative regulator of Wnts. Small molecules that stabilize the Axin complex or promote its activity may be used to inhibit the canonical Wnt pathway. See, e.g., Lu J, et al. Bioorg Med Chem Lett. 19(14):3825-7, 2009, and Chen, supra, for description of certain small molecules that inhibit Axin. Evenness interrupted (Evi; also known as Wntless (Wls) and Sprinter) is a membrane protein that is specifically required for secretion of multiple Wnts (Bänziger C, et al. Cell, 125 (3):509-22, 2006. Inhibitors of Wntless would thus inhibit multiple Wnt proteins and pathways. One of skill in the art would be aware of other proteins that could be inhibited or stimulated to inhibit multiple Wnts.

Wnt signaling may be stimulated by a variety of different methods. In some embodiments, Wnt signaling is activated by inhibiting one or more endogenous Wnt antagonists, such as those described above. Since these endogenous antagonists function to inhibit Wnt signaling, this approach is also referred to as "disinhibition". Endogenous Wnt inhibitors may be inhibited using agents such as antibodies, aptamers, or small molecules that bind to the inhibitor and prevent it from effectively interacting with Wnt receptors. In other embodiments, synthesis and/or secretion of endogenous Wnt antagonists is inhibited using RNAi agents or antisense approaches. In some embodiments, SFRP1 is inhibited using a diarylsulfone sulfonamide such as WAY-316606. See, e.g., Moore, W J et al., J Med Chem. 52(1):105-16, 2009. In other embodiments, SFRP1 is inhibited using an iminooxothiazolidine See, e.g., Shi M, et al. Bioorg Med Chem Lett. 19(22): 6337-9, 2009.

In other embodiments, Wnt signaling may be activated by contacting cells with one or more Wnt protein(s), optionally in combination with contacting the cells with an inhibitor of an endogenous Wnt antagonist. Soluble, biologically active Wnt proteins may be prepared in purified form using methods known in the art. See, e.g., U.S. Pat. Pub. No. 20040248803 and Willert, K., et al., Nature, 423: 448-52, 2003. In certain embodiments the soluble, biologically active Wnt protein is Wnt5a or Wnt16 (Wnt16v1 or Wnt16v2).

In other embodiments, small molecules that act on proteins involved in one or more steps of the Wnt signaling pathway may be used. For example, GSK3 inhibitors may be used to activate canonical Wnt signaling. Many potent and selective small molecule inhibitors of GSK3 have now been identified (Wagman A S, Johnson K W, Bussiere D E, Curr Pharm Des., 10(10): 1 105-37, 2004). Exemplary GSK3 inhibitors of use include the following: (1) BIO: ((2'Z,3'E)-6-Bromoindirubin-3'-oxime. 6-bromoindirubin-3'-oxime), a potent, reversible and ATP-competitive GSK-3 inhibitor (Polychronopoulos, P. et al. J. Med. Chem. 47, 935-946, 2004). (2) AR-AO 14418: N-(4-Methoxybenzyl)-N'-(5-nitro-1,3-thiazol-2-yl)urea. AR-A014418, inhibits GSK3 (IC50=104 nM), in an ATP-competitive manner (Ki=38 nM), AR-A014418 does not significantly inhibit cdk2 or cdk5 (IC50>100 µM) or 26 other kinases, demonstrating high specificity for GSK3 (Bhat, R., et al., J. Biol. Chem. 278, 45937-45945, 2003). (3) SB 216763: 3-(2,4-DichlorophenylV4-(1-methyl-1H-indol-3-ylV 1H-pyrrole-2,5-dione. See, e.g., Smith, D. G., et al, Bioorg, Med. Chem. Lett. 11, 635-639, (2001) and Cross, D. A., et al., J. Neurochem, 77, 94-102, (2001), (4) SB 415286: 3-[(3-Chloro-4-hydroxyphenyl)amino]-4-(2-nitrophenyl)-1H-pyrrol-2,5-dione. SB 415286 is described in Smith, D. G., et al, Bioorg. Med. Chem. Lett. 11,635-639, 2001 and Coughlan, M. P., et al, Chem. Biol. 10, 793-803, 2000, (5) TDZD-8: 4-Benzyl-2-methyl-1,2,4-thiadiazolidine-3,5-dione. This compound is a selective inhibitor of GSK-3, a thiadiazolidinone derivative, a non-ATP competitive inhibitor of GSK-3β (IC50=2 µM). It does not inhibit Cdk-1/cyclin B, CK-II, PKA or PKC at >100 µM. It has been proposed to bind to the kinase site of GSK-3β. (Martinez et al., J. Med. Chem. 45, 1292-1299, 2002); CHIR-91 1 and CHIR-837 (also referred to as CT-99021 and CT-98023 respectively). Chiron Corporation (Emeryville, Calif.) and related compounds are of use. Lithium chloride, sodium valproate, and GSK3 inhibitor II (Calbiochem) are other GSK3 inhibitors of use. Additional GSK3 inhibitors are described in U.S. Pat. Nos. 6,057,117 and 6,608,063; U.S. patent application publications 20040092535, 20040209878, 20050054663. Other GSK3 inhibitors of use are described in WO/2003/049739; WO/2002/085909; WO/2003/01 1287; WO/2005/039485, and/or WO/2006/091737. See also WO/2009/032194 for discussion of compounds and methods of use to stimulate Wnt signaling. One of skill in the art would also be aware of proteins involved in the co- or post-translational processing, secretion, or destruction of Wnts that could be inhibited or stimulated to stimulate multiple Wnts.

The concentration at which compounds are used in an inventive method, e.g., the concentration at which such compounds are present in cell culture medium following addition thereto, can vary. For example, suitable ranges may be between 0.1 ng/ml and 50,000 ng/ml, e.g., between 1 ng/ml and 10,000 ng/ml, e.g., between 10 ng/ml and 2,500 ng/ml, etc. The particular concentration will depend on the potency and identity of the agent, other agents used in combination therewith, and the desired result. Some non-limiting concentrations for certain compounds are provided in the Examples. Exemplary, non-limiting ranges may vary between 0.1-fold and 10-fold from such concentrations, e.g., between 0.2-fold and 5-fold, or between 0.5-fold and 2-fold, in various embodiments.

One of skill in the art will appreciate that the particular endogenous molecules that are involved in regulating, e.g. stimulating or inhibiting, the TGFβ, Wnt, and BMP pathways may differ in different cell types. For example, different epithelial cell types may naturally express different endogenous Wnt inhibitors. One of skill in the art could select appropriate inhibitors of those inhibitors in order to induce an EMT in such cells. For example, if a cell expresses primarily SFRP2 rather than SFRP1, an antibody to SFRP2 could be used to disinhibit Wnt signaling so as to promote induction of EMT and/or maintenance of a mesenchymal and SC-like state.

One could also or alternately inhibit one or more molecules that function downstream of Wnts in a non-canonical pathway, e.g., the Wnt $Ca^{2+}$ pathway or in certain embodiments of the invention. For example, the JNK/c-Jun pathway functions in the non-canonical Wnt pathway (e.g., downstream of Wnt5a) and downstream of TGFβ. PKC functions downstream in the non-canonical Wnt pathway (e.g., downstream of Wnt5a). Numerous small molecule inhibitors of these proteins are known in the art and could be used in an EMT inhibition composition. For example, SP60025 and BI-78D3 are small molecule JNK inhibitors. PKC412 and CGP41251 are small molecule PKC inhibitors.

Certain of the inventive methods comprise perturbing cell adhesion. As noted above, epithelial cells are attached to one another by intercellular adhesion complexes such as tight junctions and adherens junctions. In certain embodiments of the invention, perturbing formation and/or maintenance of such complexes promotes EMT and/or help maintain cells in a mesenchymal and/or SC-like state. Adhesion complex formation and/or maintenance can be perturbed by contacting cells with an antibody that binds to a protein that is a component of such adhesion complex, e.g., to an extracellular domain thereof. For example, antibodies that bind to E-Cadherin (an adherens junction protein), or to Occludin, Claudin 1, or Claudin 2 (tight junction proteins with extracellular domains) may be used in some embodiments. Other agents that bind to adhesion complex proteins, such as aptamers, could be used in certain embodiments. RNAi or antisense molecules could be used to inhibit production of one or more of these proteins. In other embodiments, a protease that cleaves an adhesion complex protein is used. For example, a matrix metalloprotease or calpain could be used in some embodiments.

As discussed above, in some embodiments of the invention, a naturally occurring polypeptide is used in a composition and/or method of the invention. In some embodiments of the invention, a variant of a naturally occurring polypeptide is used. Variants of a polypeptide include polypeptides that differ by one or more amino acid substitutions, additions, or deletions, relative to the polypeptide. For example, polypeptide variants of a naturally occurring polypeptide include polypeptides that differ by one or more amino acid substitutions, additions, or deletions, relative to a naturally occurring polypeptide. An addition can be an insertion within the polypeptide or an addition at the N- or C-terminus. In some embodiments, the number of amino acids substituted, deleted, or added can be for example, about 1 to 30, e.g., about 1 to 20, e.g., about 1 to 10, e.g., about 1 to 5, e.g., 1, 2, 3, 4, or 5. It will be appreciated that naturally-occurring allelic variants of the reference sequence for a particular protein may exist in the population, and such variants may be used in certain embodiments of the invention. It will also be appreciated that splice variants may exist, which are encompassed herein. In some embodiments, a polypeptide variant comprises a polypeptide whose sequence is homologous to the sequence of polypeptide, over at least 50 amino acids, at least 100 amino acids, at least 150 amino acids, or over the full length of the polypeptide (but is not identical in sequence to the polypeptide). In some embodiments, a polypeptide variant comprises a polypeptide at least 70%, 75%, 80%, 85%, 90%, 95%, 96%, 97%, 98%, 99%, or more identical to a polypeptide over at least 50%, 60%, 70%, 80%, 85%, 90%, 95%, 96%, 97%, 98%, 99%, or 100% of the polypeptide. For example, in some embodiments, a polypeptide variant comprises a polypeptide whose sequence is homologous to the sequence of a naturally occurring polypeptide, over at least 50 amino acids, at least 100 amino acids, at least 150 amino acids, or over the full length of the naturally occurring polypeptide (but is not identical in sequence to the naturally occurring polypeptide). In some embodiments, a polypeptide variant comprises a polypeptide at least 70%, 75%, 80%, 85%, 90%, 95%, 96%, 97%, 98%, 99%, or more identical to a naturally occurring polypeptide over at least 50%, 60%, 70%, 80%, 85%, 90%, 95%, 96%, 97%, 98%, 99%, or 100% of the naturally occurring polypeptide. In some embodiments, a polypeptide comprises or consists of a fragment of a naturally occurring polypeptide. A fragment is shorter than the naturally occurring polypeptide and is identical to it over the length of the fragment. In some embodiments, a fragment is at least 50%, 60%, 70%, 80%, 85%, 90%, 95%, 96%, 97%, 98%, or 99% as long as a naturally occurring polypeptide. In some embodiments, one or more amino acids at the C-terminus of a naturally occurring polypeptide are deleted. In some embodiments, one or more amino acids at the N-terminus are deleted. The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of TGA and TGB (here TGA and TGB are the sum of the number of residues and internal gap positions in sequences A and B in the alignment), and multiplying by 100. When computing the number of identical residues needed to achieve a particular percent identity, fractions are to be rounded to the nearest whole number. One of skill in the art will be aware of a variety of computer programs that may be used for sequence alignment and/or determining percent identity. For example, computer programs such as BLAST2, BLASTN, BLASTP, Gapped BLAST, etc., generate alignments. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877, 1993 is incorporated into the NBLAST and XBLAST programs of Altschul et al. (Altschul, et al., J. Mol. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See the Web site having URL ncbi.nlm.nih.gov. Other suitable programs include CLUSTALW (Thompson JD, Higgins DG, Gibson TJ, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.)

In some embodiments, a polypeptide variant is a functional variant, i.e., the variant at least in part retains at least one biological activity of a naturally occurring polypeptide or non-naturally occurring polypeptide of interest. In some embodiments, a functional variant retains at least 10%, 20%, 30%, 40%, 50%, 60%, 70%, 80%, 90%, 95%, 96%, 97%, 98%, 99%, or more of the activity of the polypeptide, e.g., naturally occurring polypeptide, e.g., about equal activity. In some embodiments, a functional variant may have greater activity than a naturally occurring polypeptide.

One of skill in the art can readily generate functional variants or fragments of polypeptides of interest herein. Information is available regarding, e.g., identification of various residues and domains important for activity and various residues that may be altered without significantly decreasing activity, as well as alignments with other polypeptides, and structural information in some instances. Similar analyses may readily be performed for other proteins in instances where such information is not already available. The information can be used to design functional variants and fragments. It will be appreciated that many proteins comprise multiple domains, wherein one or more of the domains may be responsible for a biological activity of interest. One of skill in the art can readily identify such domain(s), e.g., using deletion analysis or generating chimeric proteins (where the particular activity differs between two or more different proteins). Thus, a polypeptide comprising a functional domain can be used rather than, e.g., a full length polypeptide. For example, a domain responsible for binding to a particular target may be used for purposes of binding to that target in certain embodiments. In some embodiments, a variant comprises one or more conservative amino acid substitutions relative to a naturally occurring polypeptide. Conservative substitutions may be made on the basis of similarity in side chain size, polarity, charge, solubility, hydrophobicity, hydrophilicity and/or the amphipathic nature of the residues involved. As known in the art, such substitutions are, in general, more likely to result in a variant that retains activity as compared with non-conservative substitutions. In one embodiment, amino acids are classified as follows:
Special: C
Neutral and small: A, G, P, S, T
Polar and relatively small: N, D, Q, E
Polar and relatively large: R, H, K
Nonpolar and relatively small: I, L, M, V
Nonpolar and relatively large: F, W, Y
Special: C See, e.g., Zhang, J. J. Mol. Evol. 50:56-68, 2000. In some embodiments, proline (P) is considered to be in its own group as a second special amino acid. Within a particular group, certain substitutions may be of particular interest, e.g., replacements of leucine by isoleucine (or vice versa), serine by threonine (or vice versa), or alanine by glycine (or vice versa). Of course non-conservative substitutions are often compatible with retaining function as well. In some embodiments, a substitution or deletion does not alter or delete an amino acid that is known in the art to be important for activity. In some embodiments, an alteration is at an amino acid that is not highly conserved between different mammalian species. In some embodiments, a substitution alters an amino acid to that present at a corresponding position in a different species. In some embodiments, a functional variant comprises a polypeptide at least 95%, 96%, 97%, 98%, 99% or 100% identical to a naturally occurring polypeptide, e.g., over at least 70%, 75%, 80%, 85%, 90%, 95%, 96%, 97%, 98%, 99% or 100% of the full length of the naturally occurring polypeptide. If desired, polypeptide variants could be tested in cell-free and/or cell-based assays or in vivo to assess their activity using any suitable method. For example, numerous methods of assessing binding activity are known in the art. It should also be understood that where a particular naturally occurring protein is referred to in the compositions and/or methods of the invention described and/or claimed herein, such compositions and/or methods encompass embodiments in which such protein (e.g., as defined by Sequence ID NO or accession number is used) and embodiments in which a functional variant of such protein is used unless otherwise indicated (e.g., by reciting a specific sequence ID NO or accession number) or otherwise evident from the context. Applicants reserve the right to limit the claims to any scope of variants and/or to any specific sequences.

In some embodiments, a variant of a naturally occurring polypeptide comprises a heterologous polypeptide portion. The heterologous portion often has a sequence that is not present in or homologous to the naturally occurring polypeptide. A heterologous portion may be, e.g., between 5 and about 5,000 amino acids long, or longer. Often it is between 5 and about 1,000 amino acids long. In some embodiments, a heterologous portion comprises a sequence that is found in a different polypeptide, e.g., a functional domain. In some embodiments, a heterologous portion comprises a sequence useful for purifying, expressing, solubilizing, and/or detecting the polypeptide. In some embodiments, a heterologous portion comprises a polypeptide "tag", e.g., an affinity tag or epitope tag. For example, the tag can be an affinity tag (e.g., HA, TAP, Myc, 6×His, Flag, GST), fluorescent or luminescent protein (e.g., EGFP, ECFP, EYFP, Cerulean, DsRed, mCherry), solubility-enhancing tag (e.g., a SUMO tag, NUS A tag, SNUT tag, or a monomeric mutant of the Ocr protein of bacteriophage T7). See, e.g., Esposito D and Chatterjee D K. Curr Opin Biotechnol.; 17(4):353-8 (2006). In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a tag is located at the N- or C-terminus, e.g., as an N- or C-terminal fusion. The polypeptide could comprise multiple tags. In some embodiments, a 6×His tag and a NUS tag are present, e.g., at the N-terminus. In some embodiments, a tag is cleavable, so that it can be removed from the polypeptide, e.g., by a protease. In some embodiments, this is achieved by including a sequence encoding a protease cleavage site between the sequence encoding the tag and the sequence encoding the rest of the polypeptide. Exemplary proteases include, e.g., thrombin, TEV protease, Factor Xa, PreScission protease, etc. In some embodiments, a "self-cleaving" tag is used. See, e.g., PCT/US05/05763. Sequences encoding a tag can be located 5' or 3' with respect to a polynucleotide encoding the polypeptide (or both). In some embodiments a tag or other heterologous sequence is separated from the rest of the polypeptide by a polypeptide linker. For example, a linker can be a short polypeptide (e.g., 15-25 amino acids). Often a linker is composed of small amino acid residues such as serine, glycine, and/or alanine. A heterologous domain could comprise a transmembrane domain, a secretion signal domain, etc. In some embodiments, a heterologous domain increases the stability or in vivo half-life of a polypeptide. Exemplary homologous domains include, e.g., albumin, albumin binding peptides, Fc domains of immunoglobulins, etc.

In other embodiments, a variant may have reduced susceptibility to inhibition by an endogenous antagonist. For example, one could engineer Wnt or BMP variants that have alterations in amino acids that play a role in the binding of endogenous Wnt or BMP antagonists to the naturally occurring Wnts or BMPs.

In general, compounds useful to modulate TGFβ, BMP, and/or Wnt signaling pathways or to perturb cell adhesion can be produced or obtained using any suitable method.

In some embodiments, proteins of use in the instant invention are produced using recombinant DNA technology. A nucleic acid encoding a naturally occurring polypeptide can readily be obtained, e.g., from cells that express the polypeptide (e.g., by PCR or other amplification methods or by cloning) or by synthesis based on a known polypeptide sequence. Typically the nucleic acid is inserted into a suitable vector such as a plasmid or virus, which is then introduced into an appropriate host cell (which may be prokaryotic or eukaryotic in various embodiments). The host cell is maintained under conditions suitable for production of the polypeptide. In the case of proteins that undergo modifications such as glycosylation, the skilled artisan may select a host cell that performs the appropriate modification. For example, mammalian cells or other eukaryotic cells may be used. One of skill in the art would know that due to the degeneracy of the genetic code, numerous different nucleic acid sequences would encode the desired polypeptide. Optionally, a sequence is codon-optimized for expression in a host cell of choice. A nucleic that encodes a particular variant can readily be generated, e.g., by modifying a naturally occurring sequence using, e.g., site-directed mutagenesis, or by other standard methods.

In some embodiments, desired protein(s) are at least partially purified from sources such as conditioned cell culture medium that has been used to culture cells that secrete (either naturally or as a result of genetic modification) the desired protein(s). Other methods of producing proteins such as chemical synthesis, protein ligation, etc., may be used in certain embodiments. In general, the compounds or cells of interest herein may be purified. "Purified" refers to agents or entities (e.g., compounds) that have been separated from most of the components with which they are associated in nature or when originally generated. In general, such purification involves action of the hand of man. Purified agents or entities may be partially purified, substantially purified, or pure. Such agents or entities may be, for example, at least 50%, 60%, 70%, 75%, 80%, 85%, 90%, 95%, 96%, 97%, 98%, 99%, or more than 99% pure. In some embodiments, a nucleic acid or polypeptide is purified such that it constitutes at least 75%, 80%, 85%, 90%, 95%, 96%, 97%, 98%, 99%, or more, of the total nucleic acid or polypeptide material, respectively, present in a preparation. Purity can be based on, e.g., dry weight, size of peaks on a chromatography tracing, molecular abundance, intensity of bands on a gel, or intensity of any signal that correlates with molecular abundance, or any art-accepted quantification method. In some embodiments, water, buffers, ions, and/or small molecules (e.g., precursors such as nucleotides or amino acids), can optionally be present in a purified preparation. A purified molecule may be prepared by separating it from other substances (e.g., other cellular materials), or by producing it in such a manner to achieve a desired degree of purity. In some embodiments, a purified molecule or composition refers to a molecule or composition that is prepared using any art-accepted method of purification. In some embodiments "partially purified" means that a molecule produced by a cell is no longer present within the cell, e.g., the cell has been lysed and, optionally, at least some of the cellular material (e.g., cell wall, cell membrane(s), cell organelle(s)) has been removed. In the context of a composition containing cells, at least 50%, 60%, 70%, 75%, 80%, 85%, 90%, 95%, 96%, 97%, 98%, 99%, or more than 99% of the cells may be of a particular type and/or have a particular marker expression profile, phenotypic characteristic, etc., in various embodiments.

It will be understood that the compounds and compositions herein may be employed in an inventive method in an amount effective to achieve a desired biological and/or therapeutic effect.

V. Culture Media and Kits

The invention further provides compositions comprising an inventive EMT induction composition or an inventive EMT inhibition composition, wherein the composition further comprises cell culture medium or at least some cell culture medium components. Any of a variety of cell culture media could be used. Exemplary cell culture media include, e.g., MEGM, DMEM, Ham's F-12, and mixtures thereof. One of skill in the art will be aware of the components of such media and methods for preparation thereof, such as nutrients (e.g., sugars and amino acids), vitamins, trace elements, ions, lipids, hormones, growth factors, and other standard cell culture medium ingredients, etc. See, e.g., Freshney, supra. One of skill in the art would appreciate that the precise amounts of many of the various components of a cell culture medium could be varied without adversely affecting the ability of the medium to support cell growth. For example, a medium may contain between 0.1 and 100-fold the concentration of any one or more components, in various embodiments. In some embodiments, the culture medium is suitable for culturing an epithelial cell type of interest. Thus, the invention provides cell culture media suitable for culturing epithelial cells for induction of an EMT and/or suitable for culturing mesenchymal cells to maintain such cells in a mesenchymal state.

The invention provides a variety of kits. In some embodiments, a kit comprises a collection of agents useful for inducing and/or maintaining an EMT as described herein. In some embodiments, a kit comprises a collection of agents useful for inhibiting an EMT as described herein. Any combination of agents may be provided. For purposes of brevity, the various combinations will not be individually recited. The agents may be packaged in individual vessels, e.g., tubes. Compatible agents may be packaged together in the same vessel if desired. In some embodiments, cells are provided as part of or in conjunction with the kit. Other kit components can include, e.g., reagents (e.g., antibodies, reporter plasmids, probes, primers) useful for detecting expression of one or more markers characteristic of an epithelial cell or characteristic of a mesenchymal cell or SC-like cell. Any of the kits can comprise instructions for use.

VI. Applications

Compositions and/or methods described herein find use in a variety of different applications, which applications are aspects of the invention. Exemplary non-limiting applications are described in this section.

1. Screening Methods

Cells that have been induced to undergo an EMT according to the invention may be used in a variety of different methods for identifying and/or characterizing compounds. For example, cells can be contacted with some but not all of the components of an EMT induction or inhibition composition and a test compound. The ability of the test compound to provide the activity of those compound(s) that were omitted from the composition is assessed. In this manner, additional compounds of use to induce or inhibit EMT may be identified. In some aspects, the invention provides methods of identifying a compound that promotes EMT. In some embodiments, the method comprises (i) contacting isolated epithelial cells with a test compound and with one or more compounds selected from each of at least two, or in some embodiments at least three, or in some embodiments at least four, of the following groups: (a) compounds that stimulate TGF-beta pathway signaling; (b) compounds that inhibit BMP pathway signaling; (c) compounds that stimulate canonical Wnt pathway signaling; (d) compounds that stimulate non-canonical Wnt pathway signaling; and (e) compounds that perturb cell adhesion; and (ii) assessing the cells for evidence of EMT, wherein if the cells exhibit increased evidence of having undergone an EMT as compared with a suitable control, the compound is identified as a compound that promotes EMT. In this manner, one could, for example, identify compounds (e.g., small molecules), that contribute to inducing EMT. In some aspects, the inventive methods identify agents that stimulate TGFβ signaling, inhibit BMP signaling, stimulate (e.g., disinhibit) canonical Wnt signaling, activate non-canonical Wnt signaling, inhibit cell adhesion (e.g., block adherens junction formation) and/or act by other mechanisms. Once identified, such compounds can be used in other methods in which it is desired to stimulate TGFβ signaling, inhibit BMP signaling, stimulate (e.g., disinhibit) canonical Wnt signaling, activate non-canonical Wnt signaling, and/or block the formation of adherens junctions.

In other aspects, the invention provides methods of identifying a compound that inhibits EMT. In some embodiments, the method comprises (i) contacting isolated epithelial cells with a test compound and with one or more compounds selected from each of at least two, or in some embodiments at least three, or in some embodiments at least four, or in some embodiments each of the following groups: (a) compounds that stimulate TGF-beta pathway signaling; (b) compounds that inhibit BMP pathway signaling; (c) compounds that stimulate canonical Wnt pathway signaling; (d) compounds that stimulate non-canonical Wnt pathway signaling; and (e) compounds that perturb cell adhesion; and (ii) assessing the cells for evidence of EMT, wherein if the cells exhibit decreased evidence of having undergone an EMT as compared with a suitable control, the compound is identified as a compound that inhibits EMT. In some embodiments, the epithelial cells are pretreated with the test compound prior to contacting them with the other compounds of step (i). The test compound may or may not be present when the cells are contacted with the other compounds. In some embodiments, this method may identify compounds that inhibit TGF-beta pathway signaling, compounds that stimulate BMP pathway signaling, inhibit canonical and/or non-canonical Wnt pathway signaling, promote cell adhesion, and/or act by other mechanisms. Once identified, such compounds can be used in other methods in which the particular activity is desired.

To assess the cells for evidence of EMT in the above methods (or in other methods of the invention), one could examine, e.g., induction of EMT TFs such as Zeb1, Zeb2, Twist, etc., and/or mesenchymal markers such as N-Cadherin, vimentin, etc. For example, in some embodiments, upregulation of at least one EMT-associated TF, e.g., by at least 5-fold, 10-fold, 20-fold, 50-fold, or 100-fold in a population of cells contacted with a combination of compounds that includes the test compound, as compared with a suitable control, indicates that the compound promotes EMT. In some embodiments, downregulation of at least one EMT-associated TF, e.g., by at least 5-fold, 10-fold, 20-fold, 50-fold, or 100-fold in a population of cells contacted with a combination of compounds that includes the test compound, as compared with a suitable control, indicates that the compound inhibits EMT. One could alternately or additionally examine properties such as motility or capacity for self-renewal that are increased in cells that have undergone an EMT. One could alternately or additionally determine the extent to which cells exhibit alteration (reduction or increase) in epithelial characteristics. For example, cells that have undergone EMT exhibit reduced expression of markers such as E-cadherin, epithelial cytokeratins, etc. In some embodiments, expression of a marker is reduced by at least 5-fold, 10-fold, 20-fold, or more. In some embodiments of the invention, epithelial cells are $CD44^{low}$ and $CD24^{high}$ while cells that have undergone an EMT are $CD44^{high}$ and $CD24^{low}$. It will be appreciated that marker patterns of cells can be readily determined by techniques, such as cell fluorescence-activated cell sorting and immunohistochemistry, etc. As will be understood, with respect to cell markers and their expression levels, "neg" (−) refers to the absence or negligible or low level of expression of the marker, and "pos" (+) refers to robust expression. A transition of expression of a cellular marker from "neg" to "pos" represents a change from the lack of expression or low levels of expression to a high level or much higher level of expression. Thus "low" refers to a low level, "high" refers to an easily detectable and high level of expression, and the distinction between low and high expression and/or the transition from low to high expression levels, or from high to low expression levels, would be readily apparent to the practitioner.

A suitable control for the above methods would be, e.g., extent to which evidence of having undergone EMT is exhibited by cells of the same type that had been contacted with the same combination of compounds of step (i) in the absence of the test compound (or in the presence of significantly lower amounts of the test compound). It will be understood that once the level of EMT that would occur (in the absence of a test compound) is established, it would not be necessary to perform the method on control cells in parallel with screening test compounds. Compounds that inhibit EMT have a variety of uses, e.g., in the treatment of EMT-associated conditions, such as those discussed herein and/or known in the art. Without wishing to be bound by any theory, compounds that disrupt one or more autocrine signaling pathways that are involved in the induction and/or maintenance of EMT may be particularly effective for such purposes. Compounds that each disrupt at least one of these pathways may have synergistic effects in inhibiting EMT when used in combination.

In some embodiments, cells that have been induced to undergo an EMT using an inventive EMT induction method are used in a screen to identify compounds that target cancer stem cells (CSCs). See, e.g., PCT/US2009/002254 (WO/2009/126310). For example, the invention provides a method for testing the ability of a compound to inhibit the growth and/or survival of a cancer stem cell, the method comprising (a) contacting one or more test cells with the compound, wherein the one or more test cells has undergone an EMT induced according to the present invention, and (b) detecting the level of inhibition of the growth and/or survival of the one or more test cells by the compound. In some embodiments, the test cells are epithelial cells, e.g., transformed epithelial cells. In some embodiments, the methods further include contacting one or more control cells with the compound and detecting the level of inhibition of the growth and/or survival of the one or more control cells by the compound. In some embodiments, the one or more control cells comprise epithelial cell(s) that have not undergone an EMT, e.g., the cells have not been contacted with an EMT induction composition of the present invention or otherwise induced to undergo EMT. In some embodiments, the methods include (a) contacting one or more test cells and one or more control cells with a compound, wherein the one or more test cells has undergone an epithelial to mesenchymal transition induced according to the present invention, and the one or more control cells has not undergone an EMT, (b) detecting the level of inhibition of the growth and/or survival of the one or more test cells and control cells by the compound; and (c) identifying the compound as a candidate CSC-selective chemotherapeutic agent if the compound has a greater inhibitory effect on the growth and/or survival of the test cells than the control cells.

A wide variety of test compounds can be used in the inventive methods. For example, a test compound can be a small molecule, polypeptide, peptide, nucleic acid, oligonucleotide, lipid, carbohydrate, or hybrid molecule. Compounds can be obtained from natural sources or produced synthetically. Compounds can be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multiwell plates. They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments, a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, and oligonucleotide libraries. A library can be focused (e.g., composed primarily of compounds having the same core structure, derived from the same precursor, or having at least one biochemical activity in common).

Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays (see mli.nih.gov/mli/). The NIH Clinical Collection (NCC) is a plated array of approximately 450 small molecules that have a history of use in human clinical trials. These compounds are highly drug-like with known safety profiles. The NCC collection is arrayed in six 96-well plates. 50 µl of each compound is supplied, as an approximately 10 mM solution in 100% DMSO. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test compound may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or antihormonal drug, etc. In some embodiments, a compound is one that has undergone at least some preclinical or clinical development or has been determined or predicted to have "drug-like" properties. For example, the test compound may have completed a Phase I trial or at least a preclinical study in non-human animals and shown evidence of safety and tolerability. In some embodiments, a test compound is substantially non-toxic to cells of an organism to which the compound may be administered or cells in which the compound may be tested, at the concentration to be used or, in some embodiments, at concentrations up to 10-fold, 100-fold, or 1,000-fold higher than the concentration to be used. For example, there may be no statistically significant effect on cell viability and/or proliferation, or the reduction in viability or proliferation can be no more than 1%, 5%, or 10% in various embodiments. Cytotoxicity and/or effect on cell proliferation can be assessed using any of a variety of assays. For example, a cellular metabolism assay such as AlamarBlue, MTT, MTS, XTT, and CellTitre Glo assays, a cell membrane integrity assay, a cellular ATP-based viability assay, a mitochondrial reductase activity assay, a BrdU, EdU, or H3-Thymidine incorporation assay could be used. In other embodiments, at least some cytotoxicity would be acceptable or, in some embodiments, desirable. For example, a compound exhibiting differential cytotoxicity towards cancer stem cells as compared with noncancerous cells would be of significant interest. In some embodiments, a test compound is not a compound that is found in a cell culture medium known or used in the art, e.g., culture medium suitable for culturing vertebrate, e.g., mammalian cells or, if the test compound is a compound that is found in a cell culture medium known or used in the art, the test compound is used at a different, e.g., higher, concentration when used in a method of the present invention.

In some aspects of any of the inventive compound screening and/or characterization methods, test compounds are contacted with test cells (and optionally control cells) at a predetermined dose. In one embodiment the dose may be about up to 1 nM, in another embodiment the dose may be between about 1 nM and about 100 nM. In another embodiment the dose may be between about 100 nM and about 10 µM. In another embodiment the dose may be at or above 10 µM, e.g., between 10 µM and 100 µM. Following incubation for an appropriate time, optionally a predetermined time, the effect or compounds or composition on a parameter of interest in the test cells is determined by an appropriate method known to one of ordinary skill in the art, e.g., as described herein. Cells can be contacted with compounds for various periods of time. In certain embodiments cells are contacted for between 12 hours and 20 days, e.g., for between 1 and 10 days, for between 2 and 5 days, or any intervening range or particular value. Cells can be contacted transiently or continuously. If desired, the compound can be removed prior to assessing the effect on the cells.

2. Preparation and Use of Progenitor Cells

In some aspects, the invention provides methods of preparing progenitor cells, the method comprising inducing epithelial cells to undergo EMT as described above. In one aspect, progenitor cells are generated by contacting epithelial cells with an EMT induction composition of the invention for a sufficient time such that at least some of the cells undergo EMT, thereby generating progenitor cells. The method can further comprise separating cells that have undergone an EMT and exhibit progenitor cell properties from cells that have not undergone EMT, e.g., based on expression of markers.

Progenitor cells that are prepared as described herein are an aspect of the invention and have a variety of uses. Such uses include cell-based therapies in which progenitor cells derived from normal epithelial cells, or differentiated cells derived from such progenitor cells, are transplanted or implanted into a subject (e.g., as described further below), methods for evaluating or screening biological activity of a therapeutic or biologically-active molecule in progenitor cells, methods for identifying new and/or improved procedures and compounds for use in growing, maintaining and/or differentiating progenitor cells, and/or for production including manufacturing of progenitor cell-derived products such as endogenous proteins, recombinant proteins, peptides, fusion polypeptides, etc. Methods for evaluating or screening biological activities of therapeutic or biologically-active molecules such as screening to identify new lead compounds, as well as identifying agents and conditions that favor the differentiation of progenitor cells into particular cell lineages, are examples of other uses of progenitor cells. See, e.g., PCT/US2006/025589

(WO/2007/005611) for non-limiting discussion regarding progenitor cells and uses thereof.

In other embodiments, an EMT inhibition composition or EMT induction composition may be used with stem cells obtained using any method known in the art. For example, an EMT inhibition composition may be useful to promote differentiation of such cells to a desired cell type or lineage. In another non-limiting example, an EMT induction composition may be useful to maintain the stem cell state of such cells during expansion, 3. Methods of Treatment and Compositions Therefor The invention provides a variety of methods of treating a subject. The invention further provides compositions, e.g., pharmaceutical compositions, suitable for performing the methods. A subject is typically a human but other mammalian species may be treated using methods of the invention. For example, subjects may be non-human primates, rodents (e.g., mouse, rat, rabbit), ungulates (e.g., ovine, bovine, equine, caprine species), canines, and felines. In some embodiments, the animal is a dog, cat, cow, horse, pig, goat, or sheep. Certain of the methods involve inhibiting EMT in a subject in need thereof. Other inventive methods involve cell therapy using progenitor cells or cells differentiated therefrom, wherein the progenitor cells are generated by inducing an EMT as described herein. "Treat", "treating" and similar terms refer to providing medical and/or surgical management of a subject. Treatment can include, but is not limited to, administering a compound or composition (e.g., a pharmaceutical composition) to a subject. Treatment is typically undertaken in an effort to alter the course of a disease, disorder, or undesirable condition in a manner beneficial to the subject. The effect of treatment can generally include reversing, alleviating, reducing severity of, delaying the onset of, curing, inhibiting the progression of, and/or reducing the likelihood of occurrence or reoccurrence of the disease, disorder, or condition to which such term applies, or one or more symptoms or manifestations of such disease, disorder or condition. A composition of this invention can be administered to a subject who has developed a disease or condition or is at increased risk of doing so relative to a member of the general population. A composition of this invention can be administered prophylactically, i.e., before development of any symptom or manifestation of a condition. Typically in this case the subject will be at risk of developing the condition. For example, an inventive composition can be administered prior to exposure of the subject to an infectious agent or prior to the occurrence of a pathogenic event. "Preventing" can refer to administering a compound or composition (e.g., a pharmaceutical composition) to a subject who has not developed a disease or condition, so as to reduce the likelihood that the disease or condition will occur or so as to reduce the severity of the disease or condition should it occur. The subject may be identified as at risk of developing the disease or condition (e.g., at increased risk relative to many most other members of the population or as having a risk factor that increases likelihood of developing the disease).

Cell-based therapies in which progenitor cells generated according to the inventive methods may be employed include the treatment of a wide variety of diseases and conditions. Examples include neurological diseases or other conditions affecting the nervous system such as Parkinson's disease, Alzheimer's disease, spinal cord injury, traumatic brain injury, and stroke. Traumatic injuries (e.g., tissue injuries, fractures), burns, heart disease (e.g., cardiomyopathy due to any of a variety of different causes), diabetes (e.g., type I diabetes involving, loss of insulin-producing beta cells), baldness, vision loss and blindness, tooth loss, osteoarthritis, tendon and ligament damage, osteochondrosis, and muscular dystrophy are other conditions that may benefit through cell-based therapies. Bone, muscle (e.g., cardiac, skeletal, smooth muscle), skin, cartilage, nerve, and brain are among the cells and tissues toward which progenitor cell-based therapies can be directed. One of skill in the art would be aware of compositions and methods useful to differentiate progenitor cells towards a desired cell lineage or type of interest. Desired cell types may be separated from other cells using methods such as cell sorting, binding to resins or matrices, etc. Such separation may be based, e.g., on expression of markers characteristic of the cell type(s) of interest or lack of expression of markers not characteristic of such cell type(s). Progenitor cells or differentiated progeny may be implanted into failing organs (e.g., the heart) to augment function. In some embodiments, progenitor cells or differentiated progeny, may be used to aid in reconstruction or sealing tissues in the context of orthopedic, urologic, gynecologic, plastic, colorectal, and/or oto-laryngological surgeries, hernia repair, etc. Moreover it is envisioned that progenitor cells and/or differentiated progeny thereof may be used in the ex vivo and/or in vivo construction of tissues or organs such as skin, soft tissues, blood vessels, kidney, liver, bladder, etc. In certain embodiments cells may, if desired, be combined with appropriate scaffolds or matrices comprising naturally occurring and/or synthetic materials such as biocompatible, optionally biodegradable, polymers, polypeptides, etc. In some embodiments, where progenitor cells are introduced into the subject, substances may be administered to promote the differentiation of such cells in vivo. In some embodiments, the epithelial cells to be used to derive progenitor cells for use in cell therapy are obtained from the subject who is the intended recipient. In some embodiments, the epithelial cells are obtained from a different individual, typically a member of the same species. In other embodiments, if desired, cells can be modified to improve their histocompatibility and/or compatible donors can be selected.

In some embodiments of the invention, components of an EMT induction composition are administered to a subject in order to induce an EMT in vivo. In some embodiments, the components are administered in combination. The phrase "in combination", as used herein, with regard to combination treatment means with respect to administration of first and second compounds, administration performed such that (i) a dose of the second compound is administered before more than 90% of the most recently administered dose of the first agent has been metabolized to an inactive form or excreted from the body; or (ii) doses of the first and second compound are administered within 48 hours of each other, or (iii) the agents are administered during overlapping time periods (e.g., by continuous or intermittent infusion); or (iv) any combination of the foregoing. Multiple compounds are considered to be administered in combination if the afore-mentioned criteria are met with respect to all compounds, or in some embodiments, if each compound can be considered a "second compound" with respect to at least one other compound of the combination. The compounds may, but need not, be administered together as components of a single composition. In some embodiments, they may be administered individually at substantially the same time (by which is meant within less than 10 minutes of one another). In some embodiments they may be administered individually within a short time of one another (by which is meant less than 3 hours, sometimes less than 1 hour, apart). The compounds may, but need not, be administered by the same route of administration. Administration of multiple compounds in any order is encompassed. When administered in combination with a second compound, the effective amount of a first compound needed to elicit a particular biological response may be less or more than the effective amount of the first compound when administered in the absence of the second compound (or vice versa), thereby allowing an adjustment of the amount dose of the either or both agent(s) relative to the amount that would be needed if one compound were administered in the absence of the other. For example, when the compounds of the invention are administered in combination, a sub-therapeutic dosage of either of the compounds, or a sub-therapeutic dosage of both, may be used in the treatment of a subject in need of treatment. In some embodiments, when two compounds are used in combination, the second compound may in some embodiments be administered at a sub-therapeutic amount to produce a desirable therapeutic result. A "sub-therapeutic amount" as used herein refers to an amount that is less than that amount which would be expected to produce a therapeutic result in the subject if administered in the absence of the other compound, e.g., less than a recommended amount. The effects of multiple compounds may, but need not be, additive or synergistic. One or more of the compounds may be administered multiple times.

In some embodiments, a BMP inhibitor is administered to provide an environment that is permissive for a subsequently administered TGF beta agonist. In some embodiments, the compounds are administered within 2, 4, 8, 12, 24, or 48 hours of each other at least once.

Inducing an EMT in vivo could be of benefit in the various diseases and conditions for which cell-based therapy is of use. For example, inducing an EMT in vivo may provide an increased number of stem cells for repair of a damaged or defective organ or tissue. To that end, compounds that induce EMT may be administered locally, at or near a site of tissue or organ damage or defect.

In another aspect, the invention provides methods of inhibiting EMT in a subject in need thereof, the method comprising administering the components of an EMT inhibition composition of the invention to the subject in combination. The subject may be at risk of or suffering from a condition in which EMT occurs in vivo and contributes to one or more pathologic features of the condition. In some embodiments of the invention, the EMT inhibition composition comprises a Wnt antagonist and a BMP agonist. For example, one such composition comprises SFRP1 and BMP4. In some embodiments, administration of a BMP pathway activator to a subject in combination with a TGFb inhibitor enhances the therapeutic effect of a given dose of the TGFb inhibitor. In some embodiments of the invention, administration of a BMP pathway activator to a subject in combination with a TGFb inhibitor allows a smaller dose of TGFb inhibitor to be used with at least equivalent therapeutic effect.

In some embodiments, the subject is in need of treatment for cancer. As known in the art, cancer is a disease characterized by uncontrolled or aberrantly controlled cell proliferation and other malignant cellular properties. The EMT process allows cells to acquire migratory properties, which facilitate cancer cell dissemination and metastasis. In addition, cancer cells that have undergone EMT exhibit increased self-renewal capacity and tumor-initiating capacity, properties characteristic of cancer stem cells. In some embodiments of the invention, interfering with autocrine signaling loops that induce and/or maintain EMT in accordance with the present invention reduces tumor metastasis and/or tumor relapse or recurrence. Interfering with autocrine signaling loops that induce and/or maintain EMT in accordance with the present invention may help reduce resistance to therapy (e.g., chemotherapeutic agents) and render cancer cells more susceptible to endogenous immune-mediated defense mechanisms. In some embodiments, the cancer is also treated using chemotherapy, radiation, and/or surgery. It is contemplated that EMT inhibition compositions may be administered locally, e.g., at the site of a tumor, e.g., prior to, during, and/or following surgery or radiation. For example, in a non-limiting embodiment, an EMT inhibition composition may be administered at least once within the 4 weeks preceding surgery and/or at least once within the 4 weeks following surgery. In another non-limiting embodiment, an EMT inhibition composition may be administered at least once within the 4 weeks preceding initiation of a course of radiation treatments and/or at least once within the 4 weeks following completion of a course of radiation treatments, and optionally one or more times between radiation treatments.

In one aspect, the invention provides a method of treating a subject in need of treatment for cancer, the method comprising administering components of an EMT inhibition composition of the invention to the subject. In some embodiments, components of the EMT inhibition composition are administered locally, in the vicinity of the tumor, or at a site where a tumor has been or will be surgically removed or irradiated. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, Ewing's sarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. In some embodiments, cancer is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, or a testicular tumor. In one embodiment, cancer is a lung carcinoma. In one embodiment, cancer is a breast carcinoma. In some embodiments, the cancer is believed to be of epithelial origin. In some embodiments, the cancer is of unknown cellular origin, but possesses molecular or histological characteristics that are associated with epithelial cells, such as the production of E-cadherin, cytokeratins or intercellular bridges.

For example, non-limiting examples of cancer chemotherapeutics that can be useful with the methods disclosed herein for treating cancer include alkylating and alkylating-like agents such as Nitrogen mustards (e.g., Chlorambucil, Chlormethine, Cyclophosphamide, Ifosfamide, and Melphalan), Nitrosoureas (e.g., Carmustine, Fotemustine, Lomustine, and Streptozocin), Platinum agents (i.e., alkylating-like agents) (e.g., Carboplatin, Cisplatin, Oxaliplatin, BBR3464, and Satraplatin), Busulfan, Dacarbazine, Procarbazine, Temozolomide, ThioTEPA, Treosulfan, and Uramustine; Antimetabolites such as Folic acids (e.g., Aminopterin, Methotrexate, Pemetrexed, and Raltitrexed); Purines such as Cladribine, Clofarabine, Fludarabine, Mercaptopurine, Pentostatin, and Thioguanine; Pyrimidines such as Capecitabine, Cytarabine, Fluorouracil, Floxuridine, and Gemcitabine; Spindle poisons/mitotic inhibitors such as Taxanes (e.g., Docetaxel, Paclitaxel) and Vincas (e.g., Vinblastine, Vincristine, Vindesine, and Vinorelbine); Cytotoxic/antitumor antibiotics such anthracyclines (e.g., Daunorubicin, Doxorubicin, Epirubicin, Idarubicin, Mitoxantrone, Pixantrone, and Valrubicin), compounds naturally produced by various species of *Streptomyces* (e.g., Actinomycin, Bleomycin, Mitomycin, Plicamycin) and Hydroxyurea; Topoisomerase inhibitors such as *Camptotheca* (e.g., Camptothecin, Topotecan and Irinotecan) and Podophyllums (e.g., Etoposide, Teniposide); Monoclonal antibodies for cancer immunotherapy such as anti-receptor tyrosine kinases (e.g., Cetuximab, Panitumumab, Trastuzumab), anti-CD20 (e.g., Rituximab and Tositumomab), and others for example Alemtuzumab, Bevacizumab, and Gemtuzumab; Photosensitizers such as Aminolevulinic acid, Methyl aminolevulinate, Porfimer sodium, and Verteporfin; Tyrosine kinase inhibitors such as Cediranib, Dasatinib, Erlotinib, Gefitinib, Imatinib, Lapatinib, Nilotinib, Sorafenib, Sunitinib, and Vandetanib; serine/threonine kinase inhibitors, (e.g., inhibitors of Abl, c-Kit, insulin receptor family member(s), EGF receptor family member(s), mTOR, Raf kinase family, phosphatidyl inositol (PI) kinases such as PI3 kinase, PI kinase-like kinase family members, cyclin dependent kinase family members, Aurora kinase family), growth factor receptor antagonists, and others such as retinoids (e.g., Alitretinoin and Tretinoin), Altretamine, Amsacrine, Anagrelide, Arsenic trioxide, Asparaginase (e.g., Pegaspargase), Bexarotene, Bortezomib, Denileukin diftitox, Estramustine, Ixabepilone, Masoprocol, Mitotane, and Testolactone, Hsp90 inhibitors, proteasome inhibitors, HDAC inhibitors, angiogenesis inhibitors, e.g., anti-vascular endothelial growth factor agents such as Bevacizumab, matrix metalloproteinase inhibitors, pro-apoptotic agents (e.g., apoptosis inducers), anti-inflammatory agents, etc.

In other embodiments, methods of inhibiting EMT in vivo are employed in the treatment of diseases and conditions characterized by fibrosis, which term refers to the formation or development of excess fibrous connective tissue in an organ or tissue, e.g., as a reparative or reactive process. For example, myofibroblasts may arise through EMT and accumulate in affected tissues, where they secrete ECM components such as collagen, Fibrosis can be caused, e.g., by exposure to particular agents (e.g., chemical agents including a variety of medication, infectious agents), as a consequence of inflammation, or may be idiopathic. For example, pulmonary fibrosis may occur as a consequence of treatment or exposure to various chemotherapy drugs (e.g., methotrexate, cyclophosphamide); medications used to treat heart arrhythmias and other cardiovascular problems (e.g., amiodarone, propranolol); and some antibiotics (e.g., nitrofurantoin, sulfasalazine), among others. Fibrosis can occur after trauma or surgery. Fibrosis may affect a variety of organs and tissues such as the kidney, lungs, liver, hear, skin, intestine, bone marrow, eye (e.g., lens, retina), retroperitoneum, mediastinum, mesentery, vascular system, lymphatic system, musculoskeletal system (e.g., muscles, joints) etc. Fibrosis can also be systemic, affecting multiple tissues and organs. Fibrosis can adversely affect the function of such organs and tissues, potentially at least in part replacing normal tissue and compromising its function and/or interfering with proper repair of damaged tissue (e.g., after surgery, trauma, burns), Myocardial, renal, and pulmonary fibrosis, for example, can be debilitating and may be fatal. In accordance with embodiments of the instant invention, an EMT inhibition composition may be used inhibit the processes that induce EMT and/or maintain cells in a state in which they contribute to fibrosis. Such compositions may be used to inhibit and/or reverse accumulation of fibrotic tissue.

Inventive methods of treatment can include a step of identifying or providing a subject suffering from or at risk of a disease or condition of interest, e.g., a condition in which it is desirable to inhibit or induce EMT. "At risk of" implies at increased risk of, relative to the risk such subject would have in the absence of one or more circumstances, conditions, or attributes of that subject, and/or relative to the risk that an average, healthy member of the population would have and/or relative to the risk that the subject had at a previous time. In some embodiments the subject is at least at a 20% increased risk (1.2 fold increased risk) of developing a disease or condition. Examples of conditions that may place a subject "at risk" will vary depending on the particular disease or condition and may include, but are not limited to, family history of the disease or condition; exposure or possible exposure (e.g., due to occupation, habits, etc.) to particular physical or chemical agents known or believed in the art to increase risk of developing the disease or condition; a mutation, genetic polymorphism, gene or protein expression profile, and/or presence of particular substances in the blood that is/are associated with increased risk of developing or having the disease relative to other members of the general population not having such mutation or genetic polymorphism; immunosuppression; presence of other diseases or conditions, age, surgery or other trauma; presence of symptoms; or any other condition that within the judgement and skill of the subject's health care provider place the subject at increased risk. In some embodiments a subject is suspected of having a disease or condition, e.g., as a result of having one or more risk factors and, typically, one or more symptoms or signs of the disease or condition. Any suitable methods may be employed to identify a subject in need of treatment according to the present invention. For example, such methods may include clinical diagnosis based at least in part on symptoms, medical history (if available), physical examination, laboratory tests, imaging studies, immunodiagnostic assays, nucleic acid based diagnostics, etc. In some embodiments, diagnosis can at least in part be based on serology (e.g., detection of an antibody that specifically reacts with a marker associated with the disease).

In some embodiments the subject is at risk of cancer or cancer recurrence. A subject at risk of cancer may be, e.g., a subject who has not been diagnosed with cancer but has an increased risk of developing cancer as compared with an age-matched control, e.g., of the same sex. For example, the subject may have a risk at least 1.2 times that of a matched control. For example, a subject may be considered "at risk" of developing cancer if (i) the subject has a mutation, genetic polymorphism, gene or protein expression profile, and/or presence of particular substances in the blood, associated with increased risk of developing or having cancer relative to other members of the general population not having such mutation or genetic polymorphism; (ii) the subject has one or more risk factors such as having a family history of cancer, having been exposed to a mutagen, carcinogen or tumor-promoting agent or condition, e.g., asbestos, tobacco smoke, aflatoxin, radiation, chronic infection/inflammation, etc., advanced age. In some embodiments the subject has one or more symptoms of cancer but has not been diagnosed with the disease, e.g., the subject may be suspected of having cancer.

The compounds and compositions disclosed herein and/or identified using a method described herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or by inhalation, e.g., as an aerosol. Depending upon the type of disease condition to be treated, compounds of the invention may, for example, be inhaled, ingested, administered locally, or administered by systemic routes. Thus, a variety of administration modes, or routes, are available. The particular mode selected will depend, of course, upon the particular compound selected, the particular condition being treated and the dosage required for therapeutic efficacy. If multiple compounds are administered they may be administered using the same or different routes in various embodiments. The methods of this invention, generally speaking, may be practiced using any mode of administration that is medically or veterinarily acceptable, meaning any mode that produces acceptable levels of efficacy without causing clinically unacceptable (e.g., medically or veterinarily unacceptable) adverse effects. In some embodiments, a route of administration is parenteral, which includes intravenous, intramuscular, intraperitoneal, subcutaneous, intraosseus, and intrasternal injection, or infusion techniques. In some embodiments, a route of administration is oral. In some embodiments, a compound or composition may be delivered to or near a site of diseased or damaged tumor. In some embodiments, inhaled medications are of use. Such administration allows direct delivery to the lung, for example in subjects in need of treatment for lung cancer or lung fibrosis, although it could also be used to achieve systemic delivery of certain compounds. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. In other embodiments, intrathecal or intracranial administration may be of use, e.g., in a subject with a tumor of the central nervous system. Other appropriate routes and devices for administering therapeutic agents will be apparent to one of ordinary skill in the art.

Suitable preparations, e.g., substantially pure preparations, of one or more compound(s) (e.g., components of an EMT inhibition composition or an EMT induction composition of the invention) may be combined with one or more pharmaceutically acceptable carriers or excipients, etc., to produce an appropriate pharmaceutical composition suitable for administration to a subject. Such pharmaceutically acceptable compositions are an aspect of the invention. The term "pharmaceutically acceptable carrier or excipient" refers to a carrier (which term encompasses carriers, media, diluents, solvents, vehicles, etc.) or excipient which does not significantly interfere with the biological activity or effectiveness of the active ingredient(s) of a composition and which is not excessively toxic to the host at the concentrations at which it is used or administered. Other pharmaceutically acceptable ingredients can be present in the composition as well. Suitable substances and their use for the formulation of pharmaceutically active compounds is well-known in the art (see, for example, "Remington's Pharmaceutical Sciences", E. W. Martin, 19th Ed., 1995, Mack Publishing Co.: Easton, Pa., and more recent editions or versions thereof, such as Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types, which are incorporated herein by reference in their entirety). Furthermore, compounds and compositions of the invention may be used in combination with any compound or composition used in the art for treatment of a particular disease or condition of interest.

A pharmaceutical composition is typically formulated to be compatible with its intended route of administration. For example, preparations for parenteral administration include sterile aqueous or non-aqueous solutions, suspensions, and emulsions. Aqueous carriers include water, alcoholic/aqueous solutions, emulsions or suspensions, including saline and buffered media, e.g., sodium chloride solution. Ringer's dextrose, dextrose and sodium chloride, lactated Ringer's. Examples of non-aqueous solvents are propylene glycol, polyethylene glycol, vegetable oils such as olive oil, and injectable organic esters such as ethyl oleate. fixed oils, polyethylene glycols, glycerine, propylene glycol or other synthetic solvents; preservatives, e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. pH can be adjusted with acids or bases, such as hydrochloric acid or sodium hydroxide. Such parenteral preparations can be enclosed in ampoules, disposable syringes or multiple dose vials made of glass or plastic.

Pharmaceutical compositions and compounds for use in such compositions may be manufactured under conditions that meet standards, criteria, or guidelines prescribed by a regulatory agency. For example, such compositions and compounds may be manufactured according to Good Manufacturing Practices (GMP) and/or subjected to quality control procedures appropriate for pharmaceutical agents to be administered to humans. Cells to be administered to a subject and compositions containing them may be maintained and handled as appropriate for such purpose in accordance with applicable standards, criteria, or guidelines.

For oral administration, compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Suitable excipients for oral dosage forms are, e.g., fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art.

Formulations for oral delivery may incorporate agents to improve stability in the gastrointestinal tract and/or to enhance absorption.

For administration by inhalation, inventive compositions may be delivered in the form of an aerosol spray from a pressured container or dispenser which contains a suitable propellant, e.g., a gas such as carbon dioxide, a fluorocarbon, or a nebulizer. Liquid or dry aerosol (e.g., dry powders, large porous particles, etc.) can be used. The present invention also contemplates delivery of compositions using a nasal spray or other forms of nasal administration.

For topical applications, pharmaceutical compositions may be formulated in a suitable ointment, lotion, gel, or cream containing the active components suspended or dissolved in one or more pharmaceutically acceptable carriers suitable for use in such composition.

For local delivery to the eye, the pharmaceutically acceptable compositions may be formulated as solutions or micronized suspensions in isotonic, pH adjusted sterile saline, e.g., for use in eye drops, or in an ointment.

Pharmaceutical compositions may be formulated for transmucosal or transdermal delivery. For transmucosal or transdermal administration, penetrants appropriate to the barrier to be permeated may be used in the formulation. Such penetrants are generally known in the art. Inventive pharmaceutical compositions may be formulated as suppositories (e.g., with conventional suppository bases such as cocoa butter and other glycerides) or as retention enemas for rectal delivery.

Direct administration to a tissue, e.g., a site of disease (e.g., at or near a tumor site) could be accomplished, e.g., by injection or by implanting a sustained release implant within the tissue. In some embodiments at least one of the compounds is administered by release from an implanted sustained release device, by osmotic pump or other drug delivery device. A sustained release implant could be implanted at any suitable site. In some embodiments, a sustained release implant is used for prophylactic treatment of subjects at risk of developing a recurrent cancer or having a chronic condition (e.g., one that typically lasts for at least 6 months and often for years or indefinitely). In some embodiments, a sustained release implant or drug delivery device delivers therapeutic levels of the active agent(s) for at least 30 days, e.g., at least 60 days, e.g., up to 3 months, 6 months, or more. Compounds may be encapsulated or incorporated into particles, e.g., microparticles, microcapsules, or nanoparticles. Biodegradable, biocompatible polymers can be used, such as ethylene vinyl acetate, polyanhydrides, polyglycolic acid, PLGA, collagen, polyorthoesters, polyethers, and polylactic acid. Methods for preparation of such formulations will be apparent to those skilled in the art. For example, and without limitation, a number of particle-based delivery systems are known in the art for delivery of siRNA. The invention contemplates use of such compositions. Liposomes or other lipid-based particles can also be used as pharmaceutically acceptable carriers.

It will be appreciated that pharmaceutically acceptable salts, esters, salts of such esters, prodrug, active metabolite, or any derivative which upon administration to a subject in need thereof is capable of providing the compound, directly or indirectly may be used in certain embodiments. The term "pharmaceutically acceptable salt" refers to those salts which are, within the scope of sound medical judgment, suitable for use in contact with the tissues of humans and/or lower animals without undue toxicity, irritation, allergic response and the like, and which are commensurate with a reasonable benefit/risk ratio. A wide variety of appropriate pharmaceutically acceptable salts are well known in the art. Pharmaceutically acceptable salts include, but are not limited to, those derived from suitable inorganic and organic acids and bases.

A variety of approaches can be used to increase plasma half-life, reduce clearance, or otherwise modify properties of a compound, e.g., a polypeptide, if desired. See, e.g., Werle M, et al., Strategies to improve plasma half life time of peptide and protein drugs. Amino Acids 30(4):351-67, 2006 and Jevsevar S, et al, PEGylation of Therapeutic Proteins, Biotechnology Journal, 5(1): 113-128, 2010 for reviews discussing some of these approaches.

Pharmaceutical compositions of the invention, when administered to a subject, are preferably administered for a time and in an amount sufficient to treat the disease or condition for which they are administered. Therapeutic efficacy and toxicity of active agents can be assessed by standard pharmaceutical procedures in cell cultures or experimental animals. The data obtained from cell culture assays and animal studies can be used in formulating a range of dosages suitable for use in humans or other subjects. Different doses for human administration can be further tested in clinical trials in humans as known in the art. The dose used may be the maximum tolerated dose or a lower dose. A therapeutically effective dose of an active agent in a pharmaceutical composition may be within a range of about 0.001 to about 100 mg/kg body weight, about 0.01 to about 25 mg/kg body weight, about 0.1 to about 20 mg/kg body weight, about 1 to about 10 mg/kg. Other exemplary doses include, for example, about 1 µg/kg to about 500 mg/kg, about 100 µg/kg to about 5 mg/kg). In some embodiments a single dose is administered while in other embodiments multiple doses are administered. Those of ordinary skill in the art will appreciate that appropriate doses in any particular circumstance depend upon the potency of the agent(s) utilized, and may optionally be tailored to the particular recipient. The specific dose level for a subject may depend upon a variety of factors including the activity of the specific agent(s) employed, the particular disease or condition and its severity, the age, body weight, general health of the subject, etc. Similarly, the number of cells to be administered in a cell-based therapy can be determined by those skilled in the art based on such considerations, the type of cell administered, etc. and will often be in the tens to hundreds of thousand, millions, or more.

It may be desirable to formulate pharmaceutical compositions, particularly those for oral or parenteral compositions, in unit dosage form for ease of administration and uniformity of dosage. Unit dosage form, as that term is used herein, refers to physically discrete units suited as unitary dosages for the subject to be treated; each unit containing a predetermined quantity of active agent(s) calculated to produce the desired therapeutic effect in association with an appropriate pharmaceutically acceptable carrier. It will be understood that a therapeutic regimen may include administration of multiple unit dosage forms over a period of time, which can extend over days, weeks, months, or years. In some embodiments, treatment may be continued indefinitely, e.g., in order to achieve prophylaxis or in the case of a chronic disease. A subject may receive one or more doses a day, or may receive doses every other day or less frequently, within a treatment period.

EXAMPLES

Example 1

Characterization of a Mesenchymal Subpopulation Isolated from Immortalized Human Mammary Epithelial Cells We examined the properties of a minority sub-population of cells that we isolated from immortalized human MECs (hereafter referred to as HMLE cells, Experimental Procedures). Similar to HMLE cells driven through EMT by ectopic expression of the Twist TF (HTwist cells; Yang et al., 2004), these cells exhibited a mesenchymal morphology and were termed MSP for "mesenchymal sub-population" (FIG. 1A). These MSP cells were initially isolated as a population of cells floating in the supernatant medium of a monolayer culture of HMLE cells. For our analyses, we also wished to eliminate from the parental HMLE culture the small minority of mesenchymal cells, which have been shown to display a CD44high/CD24low-negative cell-surface profile (Mani et al., 2008). Using MACS (Magnet-Activated Cell Separation), HMLE cells expressing CD24, a marker tightly associated with the epithelial state of MECs, were positively selected to yield a purified epithelial HMLE$^{24+}$ population.

Figure 1B:
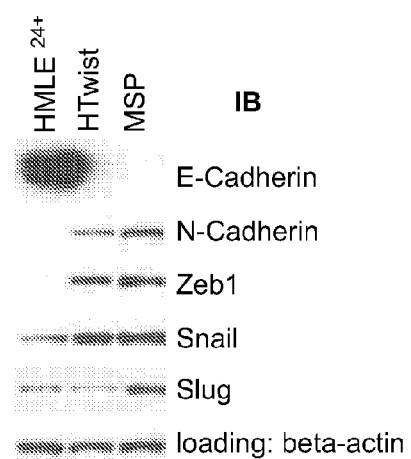
Figure 1C:
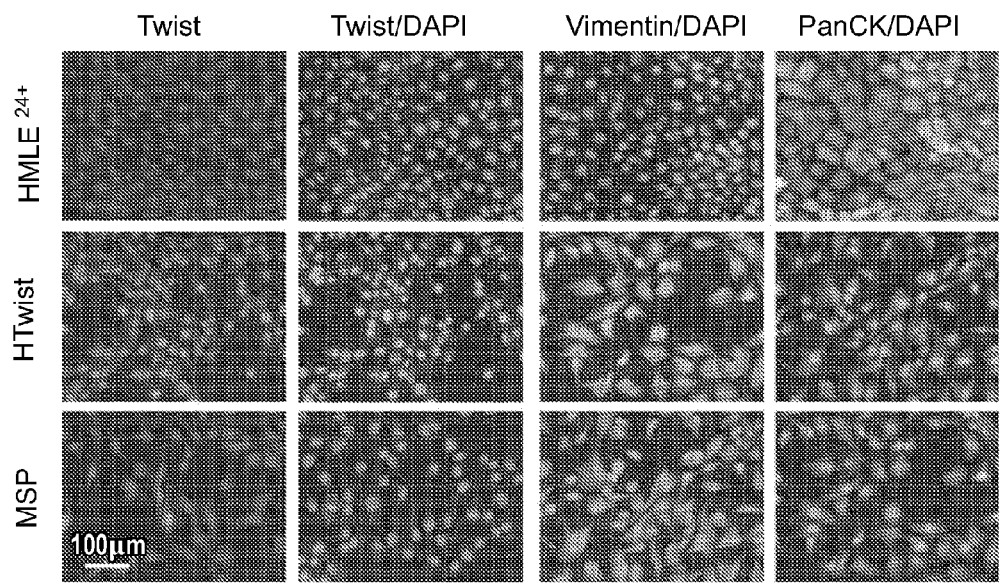
Figure 1D:
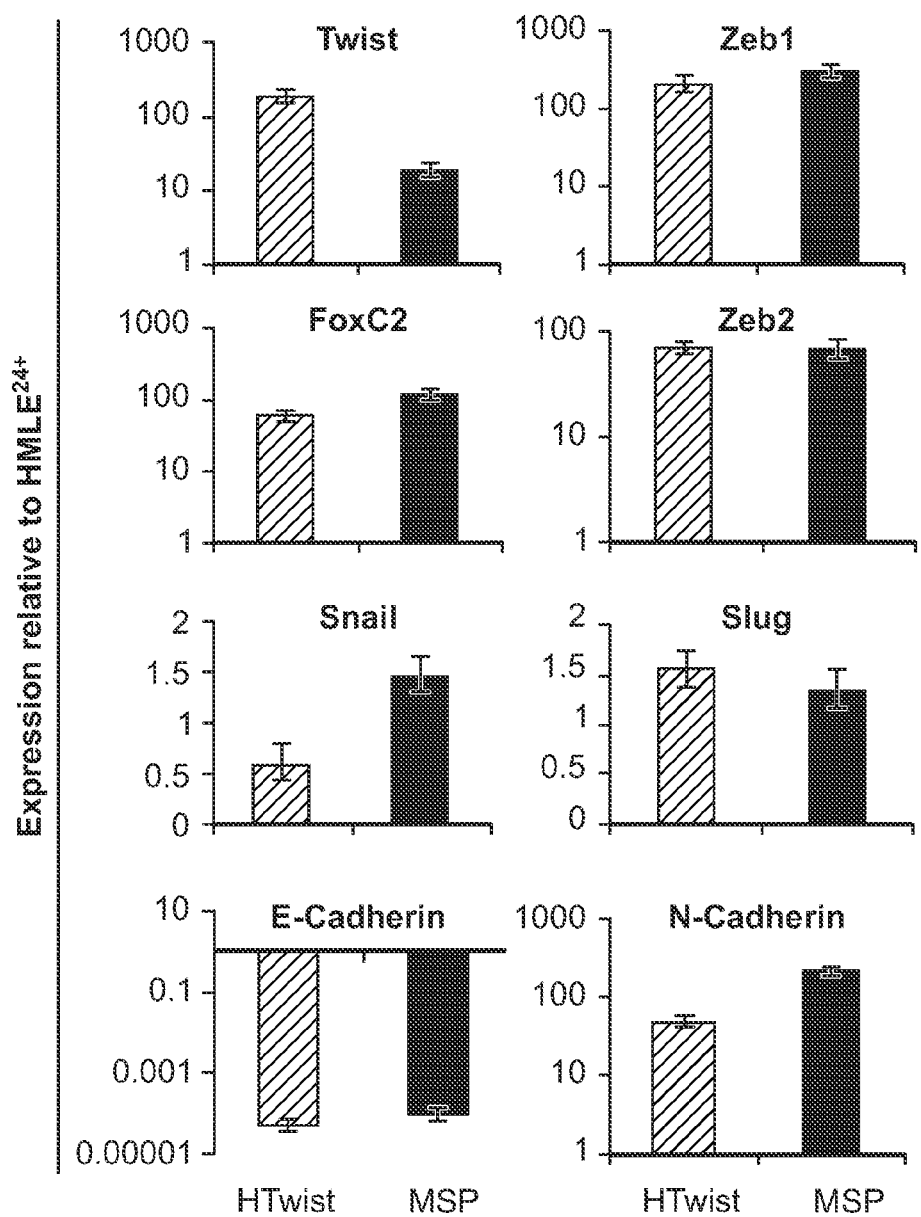

Through various analyses, we noted that, in comparison to HMLE$^{24}$ cells, epithelial markers were downregulated in MSP cells; instead, they expressed mesenchymal markers and components of the EMT program similar to HTwist cells (FIGS. 1B-1D). Thus, we found that endogenous mRNA levels of Twist were up-regulated 10-fold in the MSP compared to HMLE$^{24+}$ cells. Further, MSP and HTwist cells expressed the Zeb1, Zeb2, FoxC2 and Snail EMT-inducing TFs at elevated levels (FIGS. 1B-1D). Of note, increased protein expression of the EMT-TF Slug was found only in MSP cells (FIG. 1B).

Figure 1E:
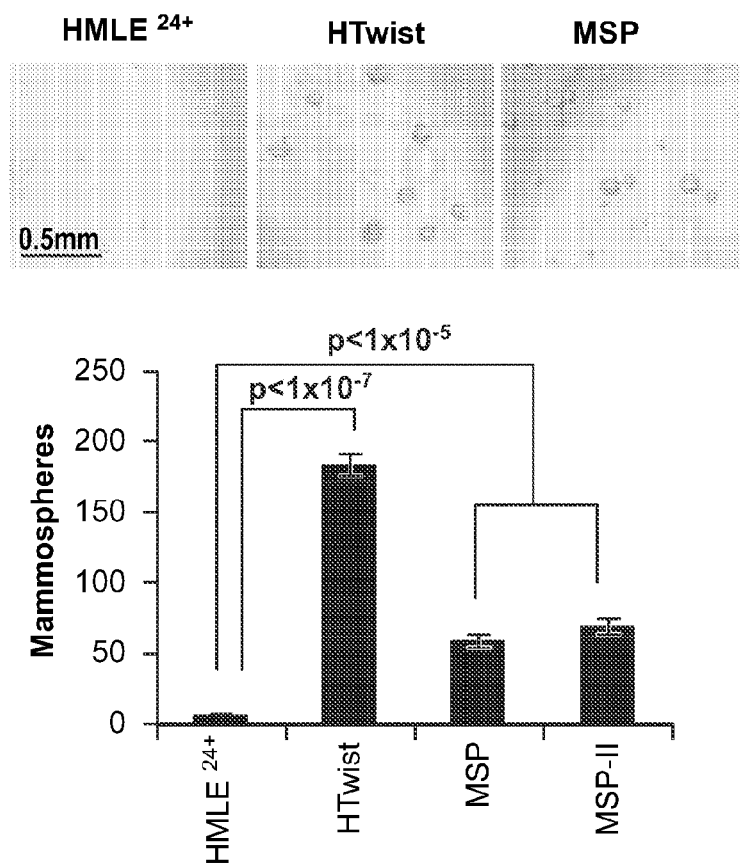

The ability of MECs to proliferate and form mammospheres when plated at clonal density in suspension cultures has been associated with the presence of murine and human mammary epithelial progenitor and SC populations (Dontu et al., 2003; Pece et al., 2010; Yu et al., 2007). We therefore compared the mammosphere-forming ability of HMLE$^{24+}$, HTwist and MSP cells. Relative to the HMLE$^{24+}$ cells, mammosphere-forming ability was increased 30-fold in HTwist cells and 10- to 20-fold in two independently derived MSP cell lines (FIG. 1E).

Figure 1F:
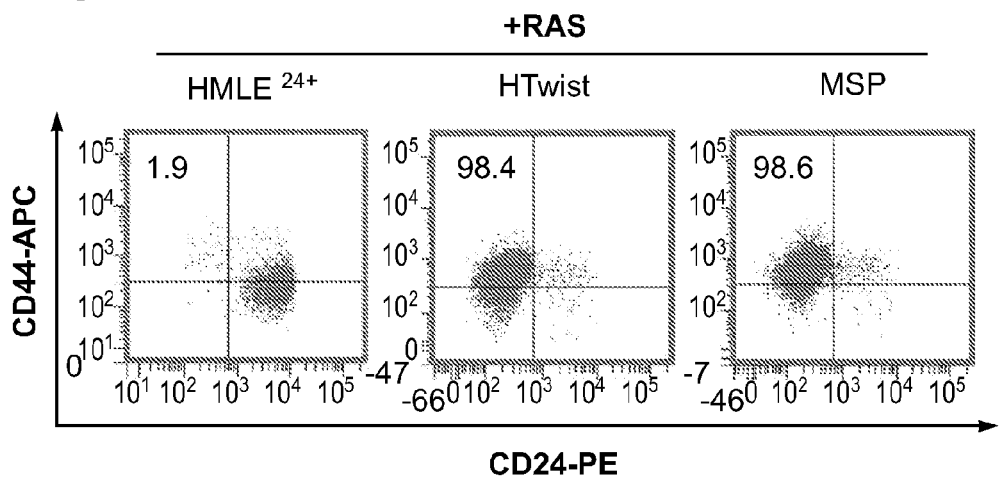

Like patient-derived human breast cancer cell populations enriched for tumor-initiating cells (Al-Hajj et al., 2003), HTwist cells transformed with the H-RAS oncogene were previously shown to exhibit a CD44high/CD24low-negative profile (termed HTwist-RAS, Mani et al., 2008). Similarly, 98% of MSP cells transformed with RAS (MSP-RAS) showed a CD44high/CD24low-negative profile (FIG. 1F). In contrast, this fraction of cells comprised less than 2% of the RAS-transformed HMLE$^{24+}$ cell populations, the bulk residing in a CD24high/CD44low-negative state.

Figures 1G, 1H:
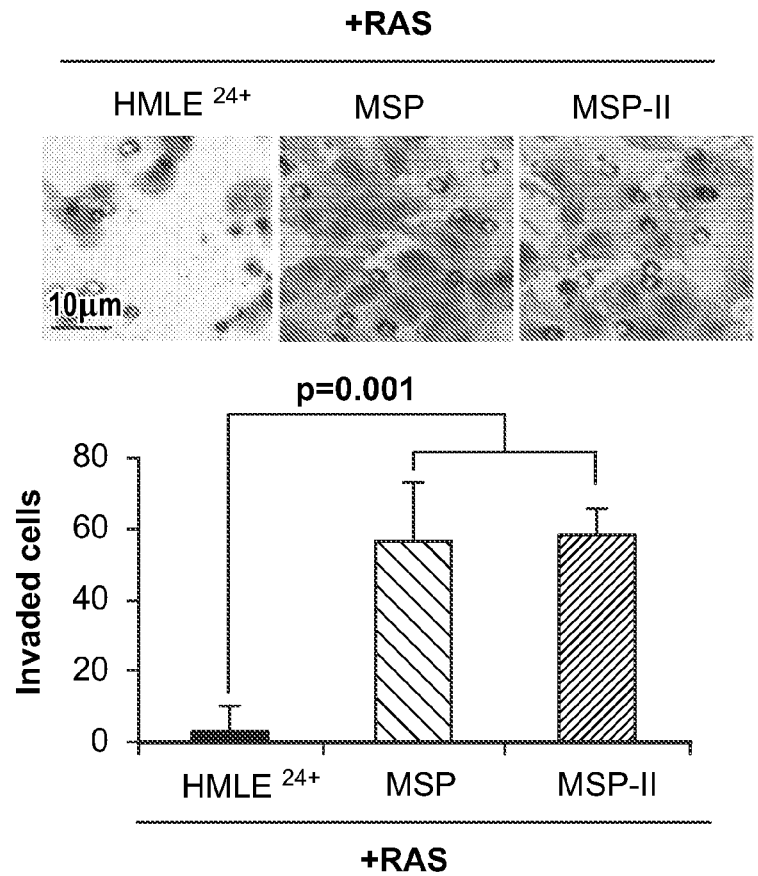

HTwist-RAS cells generate tumors with enhanced efficiency compared to HMLE-RAS cells (Mani et al., 2008). Therefore, we tested the tumor-initiating ability of MSP-RAS cells relative to the HMLE$^{24+}$-RAS population. In accord with previously published results (Mani et al., 2008), implantation of 1×10$^5$ HMLE$^{24+}$-RAS cells was necessary for subcutaneous tumor formation, whereas HTwist-RAS and MSP-RAS populations were enriched for tumor-initiating cells by at least two orders of magnitude (FIG. 1G). Together, these data indicated that MSP cells, like HTwist cells, exhibited certain properties of normal SCs, and their transformed derivatives of tumor-initiating cells.

Figure 1I:
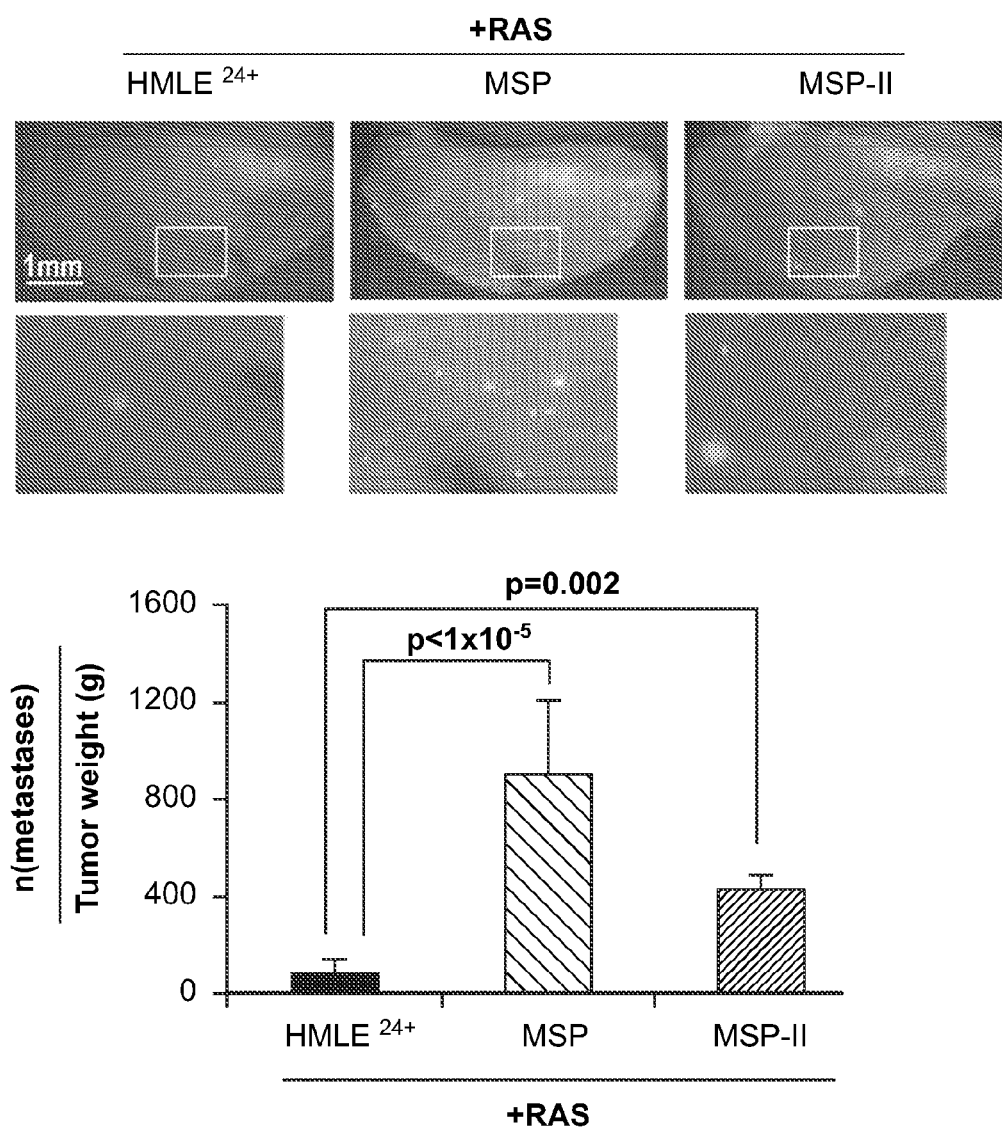

Expression of Twist has been shown to be necessary for metastasis in a mouse model of breast cancer pathogenesis (Yang et al., 2004). These observations caused us to examine the invasive and metastatic abilities of two independently isolated MSP cell lines (MSP, MSP-II) transformed with RAS. Relative to HMLE$^{24+}$-RAS cells, both MSP-RAS cell lines demonstrated a 20-fold increase in invasiveness in vitro (FIG. 1H). GFP-labeled MSP-RAS and MSP-II-RAS cells implanted in the mammary fat pads of mice gave rise to tumors that had a 10- and 5-fold increased ability, respectively, to seed metastatic foci in the lung compared to the weakly metastatic HMLE$^{24+}$-RAS cells (FIG. 1I).

Taken together, these observations indicated that MSP cells reside in a cellular state characterized by the display of mesenchymal and motility traits as well as properties associated with cell populations containing normal SCs; their transformed derivatives, the MSP-RAS cells, continued to express traits associated with passage through an EMT and associated acquisition of certain SC and tumor-initiating traits. Hence, MSP are phenotypically similar to HTwist cells. However, the initial induction of their cellular state arose spontaneously and was thus not provoked by an introduced, experimentally predetermined genetic factor.

Example 2

Figure 8A:
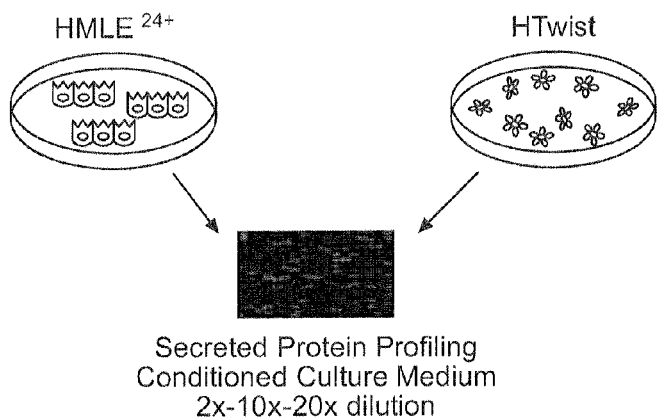
FIGS. 8A-8D. EMT secreted protein and gene expression profile.
Figure 8C:
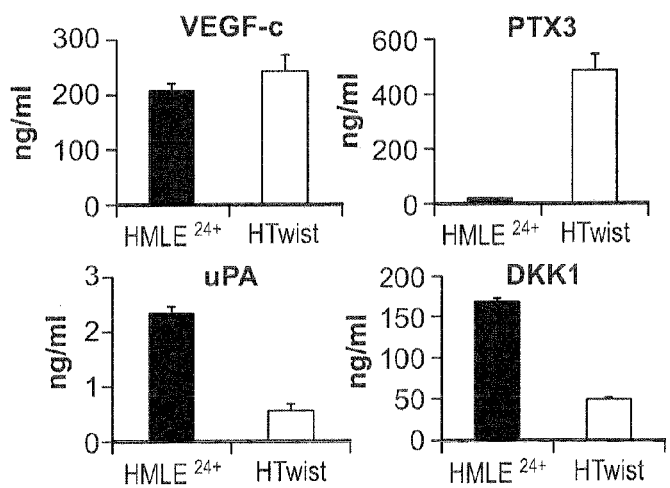
Figure 8B:
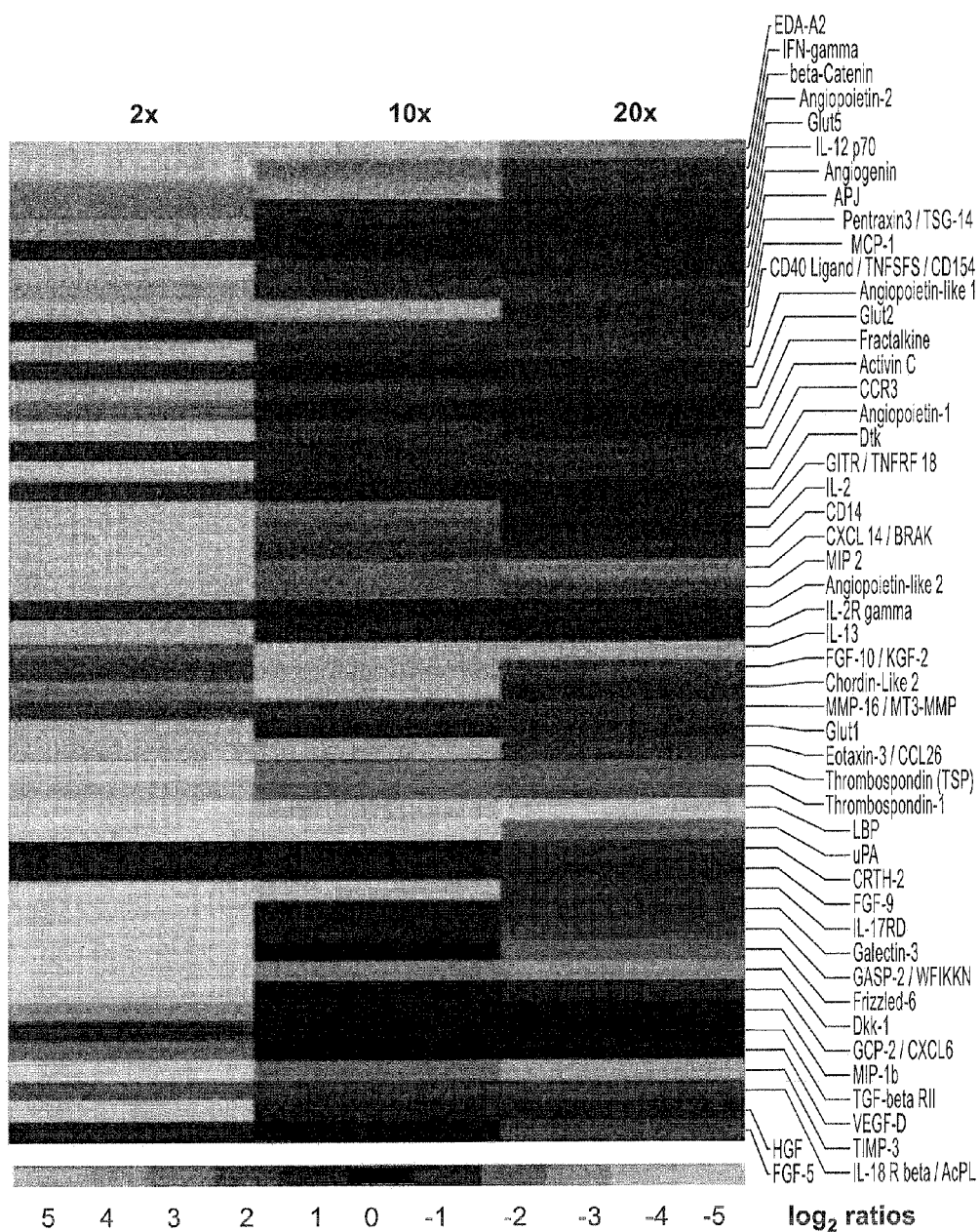

Comparative Profiling of the Autocrine Signaling Context in HMLE, HTwist and MSP Cells We speculated that maintenance of the mesenchymal and SC-like state associated with passage through an EMT might depend on the activation of autocrine signaling loops. The nature of such autocrine loops, we reasoned, might be revealed by comparing the factors that are released into the culture medium by MECs before and after they have passed through an EMT. To test this notion, we characterized the secreted protein profile of HMLE$^{24+}$ and HTwist cells using antibody arrays (FIG. 8A). To identify differentially regulated secreted proteins in HTwist cells, we selected the top 10% proteins exhibiting consistent changes across a dilution series for visualization in a heatmap (FIG. 8B. We also verified differential secretion of several proteins by ELISA (FIG. 8C). Based on functional grouping of the antibodies on the array, this "EMT Secreted Protein Profile" was found to contain predominantly pro-angiogenic factors, proteins acting in Wnt, TGF-beta, and FGF signaling pathways, chemo- and cytokines, as well as other proteins that we were unable to assign to functional groups (Table 3).

TABLE 3

Functional grouping of top 50 differentially secreted protein in HTwist cells.

| Functional group | Antibodies on array | | Antibodies Top 50 | | Enrichment |
|---|---|---|---|---|---|
| | n | % | n | % | fraction |
| Angiogenesis | 31 | 6.1 | 7 | 14.0 | 2.3 |
| Wnt | 22 | 4.3 | 4 | 8.0 | 1.8 |
| FGF | 22 | 4.3 | 3 | 6.0 | 1.4 |
| TGF + BMP | 43 | 8.5 | 5 | 10.0 | 1.2 |
| Chemokines/Cytokines | 143 | 28.2 | 14 | 28.0 | 1.0 |
| Other | 216 | 42.6 | 16 | 32.0 | 0.8 |
| MMP | 20 | 3.9 | 1 | 2.0 | 0.5 |
| IGF | 10 | 2.0 | 0 | 0.0 | 0.0 |
| TOTAL | 507 | 100.0 | 50 | 100.0 | 1.0 |

We concluded that some of the factors in the EMT Secreted Protein Profile were likely to operate via heterotypic paracrine signaling channels. For example, several angiopoietin-like growth factors were contained among the proteins upregulated in HTwist; such factors might affect endothelial cells comprising the vasculature of normal and neoplastic tissues. For our initial studies, however, we wished to focus on those factors that were likely to function in an autocrine manner. For this reason, the work described below emphasizes other signaling pathways with components included in the Secreted Protein Profile. Since two out of three FGF ligands contained in the EMT Secreted Protein Profile were downregulated, we examined the two remaining functional groups, Wnt and TGF-beta signaling, in more detail.

Figure 8D:
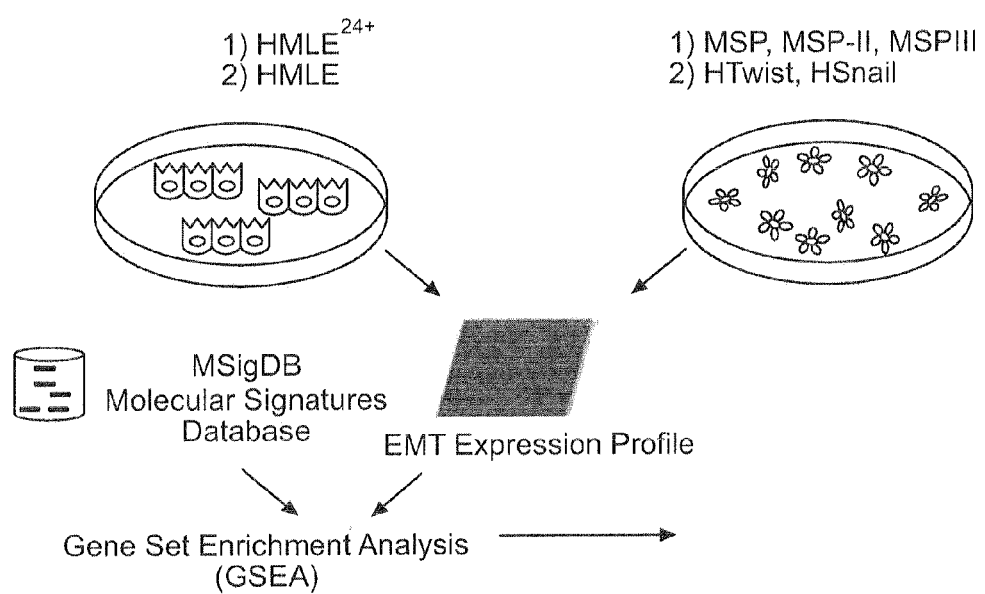
Figure 8D:
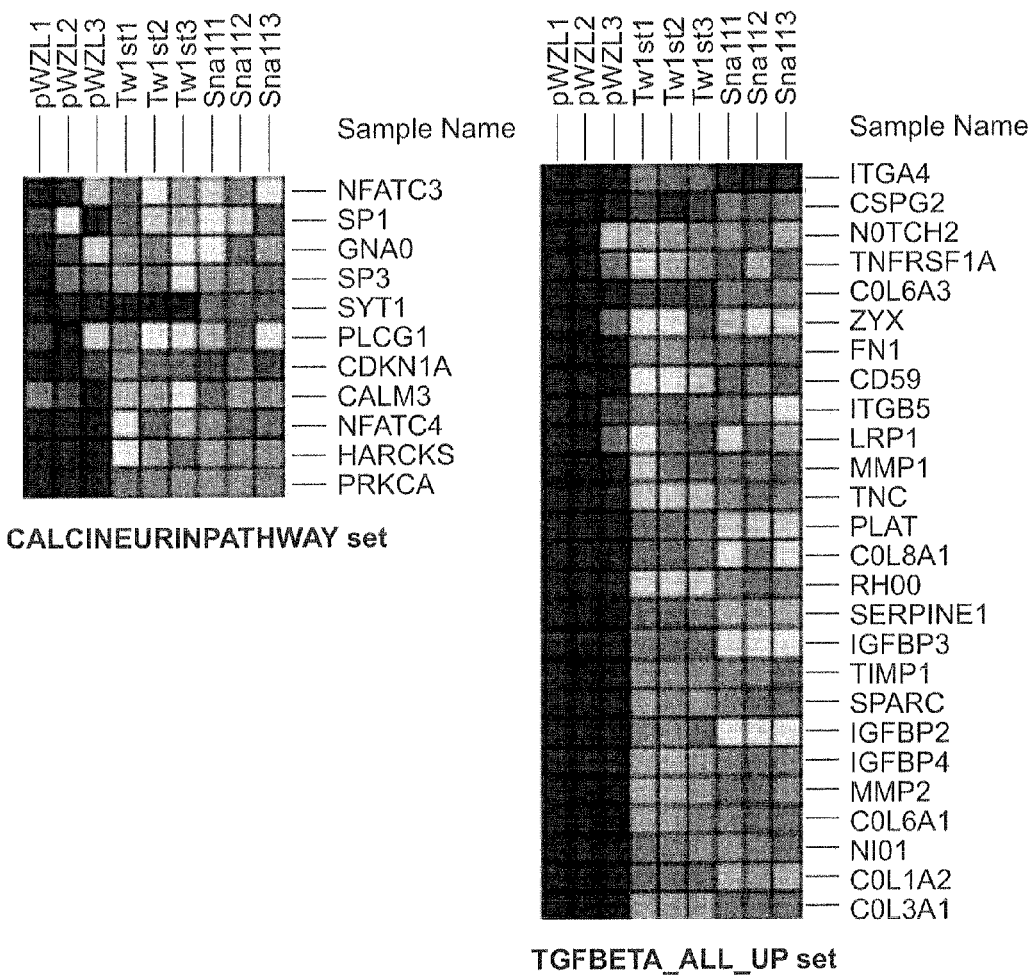

In order to connect changes in secreted proteins with activation of downstream pathways and to overcome bias created by the representation of antibodies on the array, we complemented the above analyses with microarray gene expression profiling of HMLE, HMLE$^{24+}$, HTwist, HMLE cells expressing the Snail TF (HSnail) and three independently derived MSP cell lines to generate an "EMT Gene Expression Profile" (FIG. 8D). To find pathways commonly involved in the EMT programs of all of these cell populations, we subjected the EMT Expression Profile to Gene Set Enrichment Analysis (GSEA). Two gene sets showed a significant enrichment in both the HTwist, HSnail and MSP cells: these encompassed the Calcineurin/NFAT signaling pathway, generally indicative of calcium signaling and a migratory phenotype (Jauliac et al., 2002; Yoeli-Lerner et al., 2005), as well as genes upregulated by TGF-beta signaling (FIG. 8D). Together, the EMT Secreted Protein and Gene Expression Profiles provided some indication that Wnt, calcium signaling and TGF-beta pathways might be specifically modulated in HTwist and MSP cells. The well-recognized role of TGF-beta in the induction of EMTs in both the developmental and tumor contexts (Zavadil et al., 2001) served as one means to validate our experimental approach.

Example 3

Figure 2A:
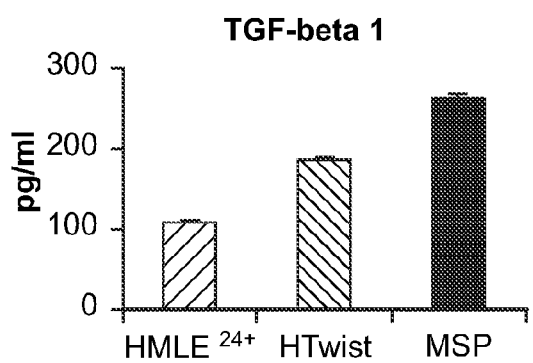
Figure 2C:
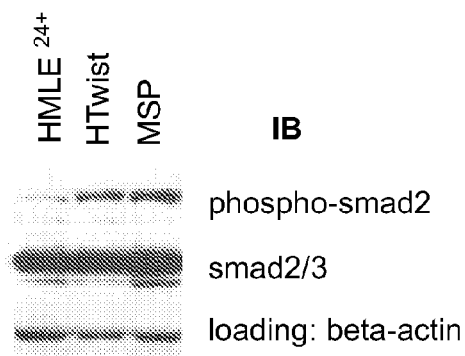
Figure 2B:
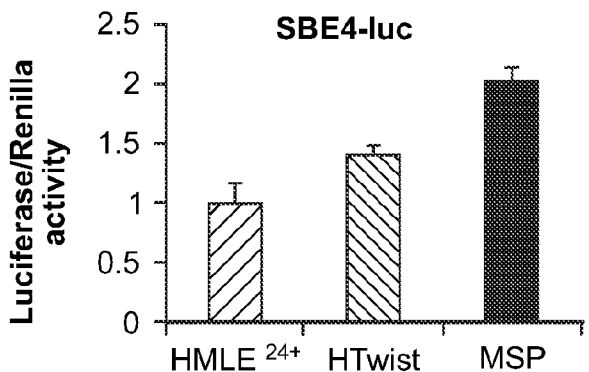
Figure 2D:
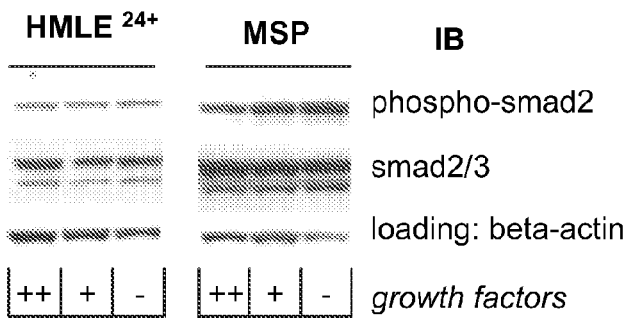

EMT-associated Autocrine Signaling: Activation of TGF-beta and Restriction of BMP Signaling In response to the above findings, we initially focused our attention on the activation state of TGF-beta signaling in HMLE$^{24+}$, HTwist and MSP cells. We noted increased secretion of TGF-beta-1 protein by HTwist and MSP cells, relative to HMLE$^{24+}$ cells (2-fold and 3-4 fold, respectively by ELISA, FIG. 2A). We also observed increased activity (1.5-2-fold) of a Smad-reporter plasmid (SBE4-luc, FIG. 2B). Finally, Smad2 phosphorylation, an indicator of active TGF-beta signaling, was nearly absent in the epithelial HMLE$^{24+}$ cells, while it was readily detected in MSP cells (FIG. 2C). When MSP cells were propagated in culture medium depleted of all growth factors, Smad2 phosphorylation remained robust, providing support for the autocrine origin of TGF-beta signaling (FIG. 2D). Together, these results indicated that autocrine TGF-beta signaling is active in HTwist and MSP cells, while this pathway was relatively inactive in the parental HMLE$^{24+}$ cells.

Figure 2E:
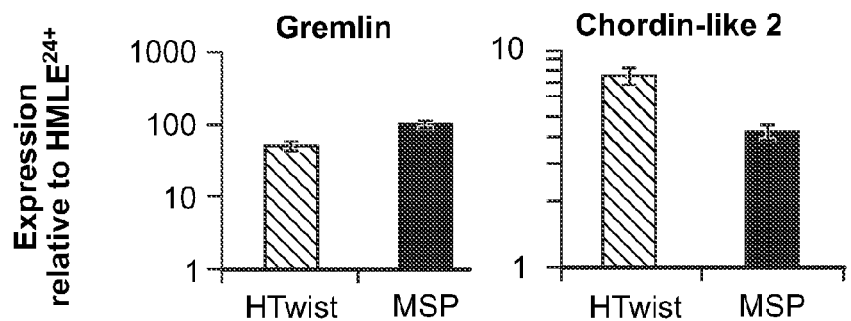
Figure 9A:
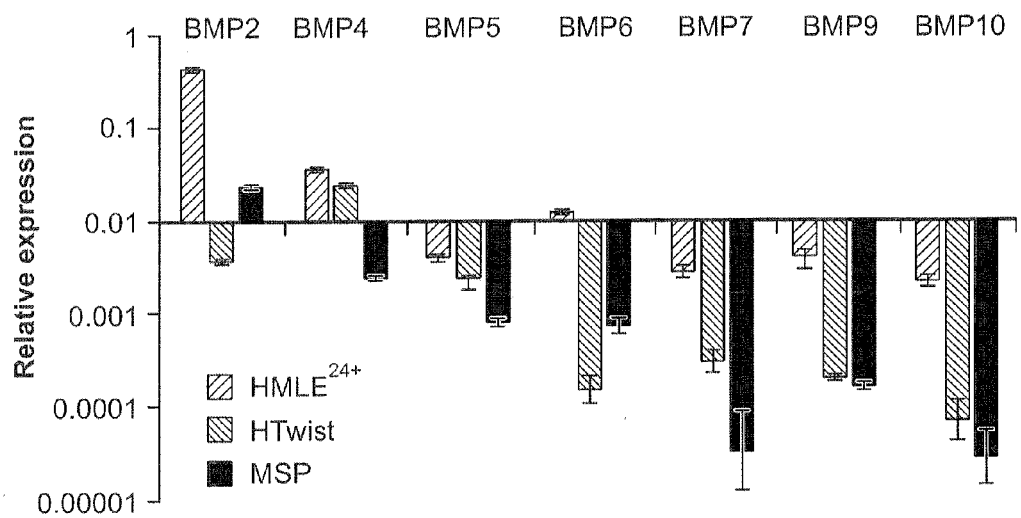

Our attention was also drawn to BMP signaling, because the EMT Secreted Protein and Expression Profile revealed upregulation of two secreted BMP antagonists, Chordin-like 2 and Gremlin. This was confirmed by RT-PCR analysis in MSP and in HTwist cells compared to the parental HMLE$^{24+}$ cell population (FIG. 2E). We interrogated the expression status of BMP ligands. We observed a dramatic and unanticipated outcome: several BMP ligands were downregulated in HTwist and MSP cells (>10-fold for BMPs 2, 4, 5, 6, 7, 9, 10, FIG. 9A. Together, these observations provided indication that HTwist and MSP cells exhibit an extracellular signaling environment that restricts BMP signaling via (1) loss of BMP ligand production and (2) upregulation of the secreted BMP antagonists Chordin-like 2 and Gremlin, We concluded that these changes, acting in concert, create an extracellular environment that is permissive for autocrine TGF-beta signaling.

Example 4

Figure 9B:
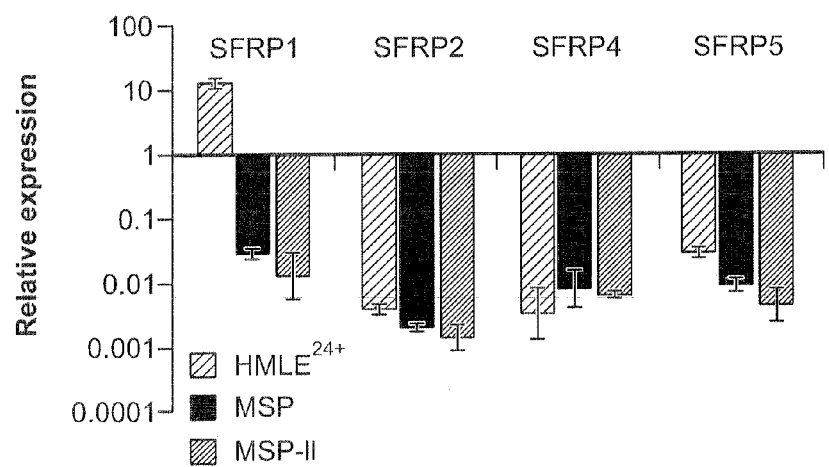
Figure 9C:
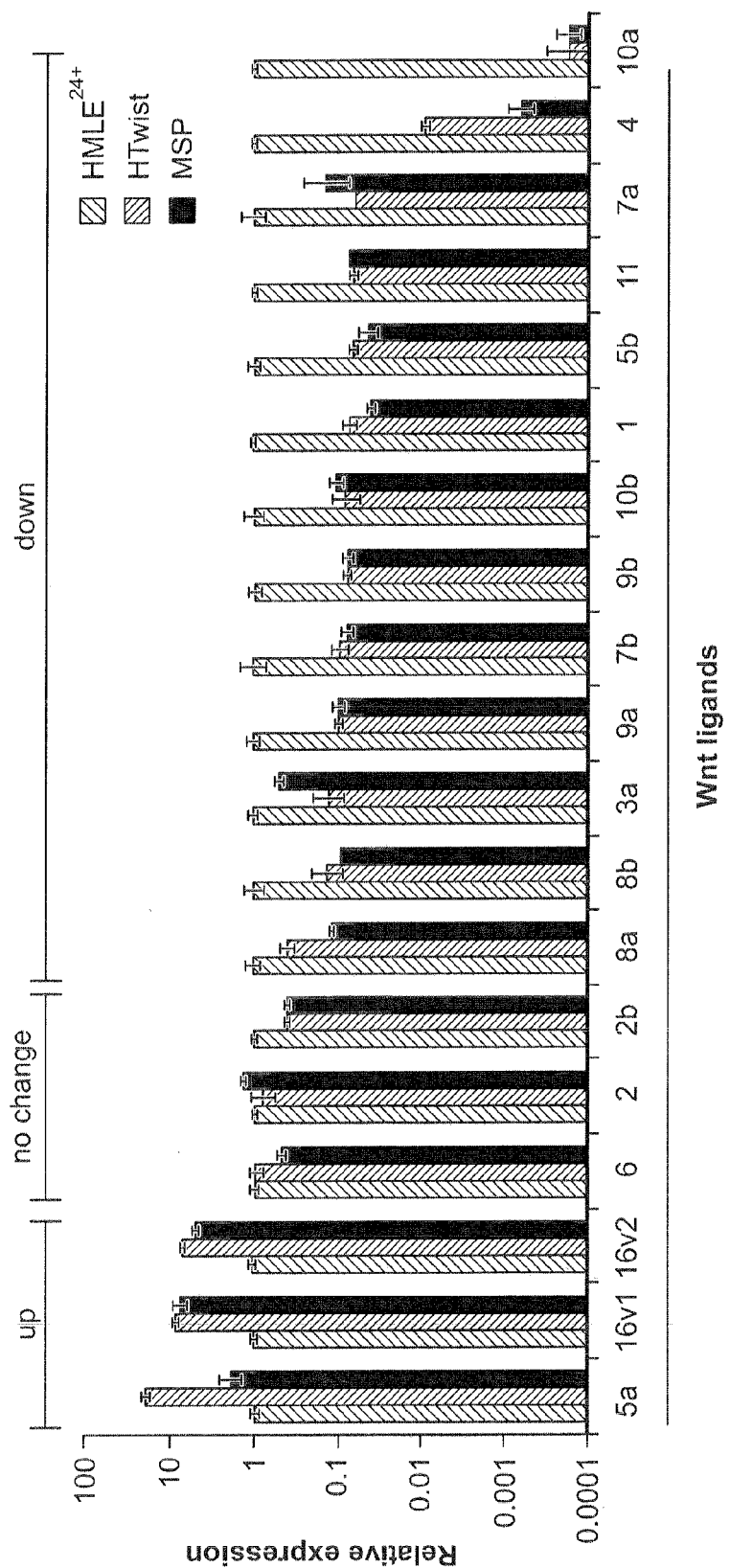

EMT-associated Autocrine Signaling: Canonical and Non-canonical Wnt Signaling Facilitated by Downregulation of Wnt Antagonists Given the presence of Wnt and calcium signaling pathways in the EMT Secreted Protein and Gene Expression Profiles, we wished to determine whether additional autocrine signaling pathways might collaborate with TGF-beta signaling in HTwist and MSP cells. The downregulation of two classes of secreted Wnt antagonists in HTwist and MSP cells directed our attention to Wnt signaling pathways. To begin, mRNA levels of Secreted Frizzled Related Protein-1 (SFRP1) were downregulated in the EMT Expression Profile. Subsequent RT-PCR analysis confirmed a 5-fold downregulation of SFRP1 mRNA in HTwist cells relative to HMLE$^{24+}$ and the near absence of its expression in MSP cell lines (FIG. 2F). Importantly, SFRP1 was the only SFRP isoform that was expressed at significant levels in HMLE$^{24+}$ cells relative to MSP cells (FIG. 9B). Functionally, SFRP1 acts as a secreted decoy receptor binding both canonical and non-canonical Wnt ligands in the extracellular space (Galli et al., 2006). In addition, Dickkopf-1 (DKK1) was downregulated in the EMT Secreted Protein Profile, which we confirmed by ELISA in both HTwist and MSP cells (8- and 5-fold, respectively, FIG. 2G). By perturbing receptor complex formation, DKK1 is thought to primarily inhibit the canonical Wnt pathway (Bafico et al., 2004).

Figure 2H:
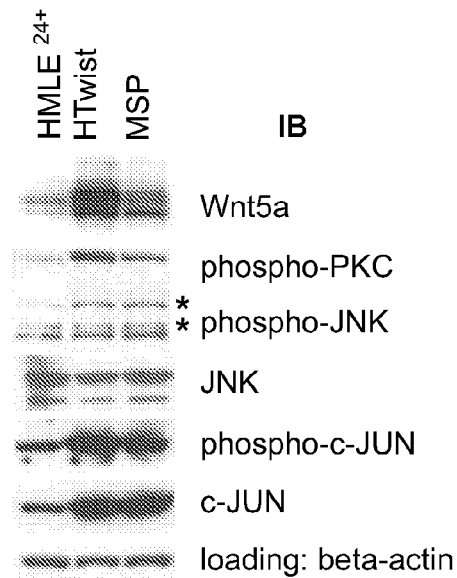

We also examined whether production of Wnt ligands was changed upon passage through an EMT. Indeed, expression of the non-canonical Wnt5a ligand was upregulated in the EMT expression profile, which was confirmed by Immunoblotting (FIG. 2H). RT-PCR analysis of the 21 remaining Wnt ligands revealed up-regulation of non-canonical Wnt ligands 16v1 and 16v2 (both 10-fold) in HTwist and MSP cells, whereas other Wnt ligands were expressed at similar levels (Wnt2, 2b and 6) and all others were downregulated (5-100-fold, FIG. 9D).

Given the observed upregulation of the Wnt5a, Wnt16v1 and 16v2 non-canonical ligands in both the HTwist and MSP cells, we analyzed the activity of associated downstream signaling pathways. Wnt5a binding to non-canonical Frizzled receptors has been shown to activate the calcium signaling that converges on protein kinase C (PKC) isoforms and is necessary for melanoma cell invasiveness (Dissanayake et al., 2007). Indeed, using a pan-phospho PKC antibody, we observed a significant level of activated PKCs in HTwist and MSP cells but not in the HMLE$^{24+}$ cells (FIG. 2F).

In addition, JNK signaling has been shown to be activated by Wnt5a as an essential component of breast cancer invasion (Pukrop et al., 2006). We found elevated phosphorylation of JNK and its downstream target, c-Jun, in HTwist and MSP populations relative to the parental HMLE$^{24+}$ cells (FIG. 2H). Since no exogenously added Wnt ligands were present in the culture medium, these results suggested that autocrine non-canonical Wnt signaling is active in HTwist and MSP cells, acting via at least two downstream pathways involving the PKC and JNK proteins.

Figure 2I:
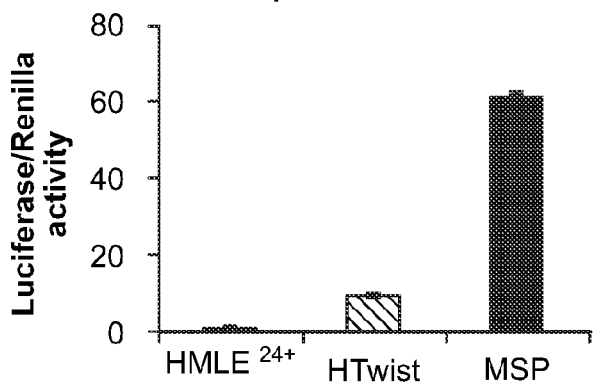
Figure 2J:
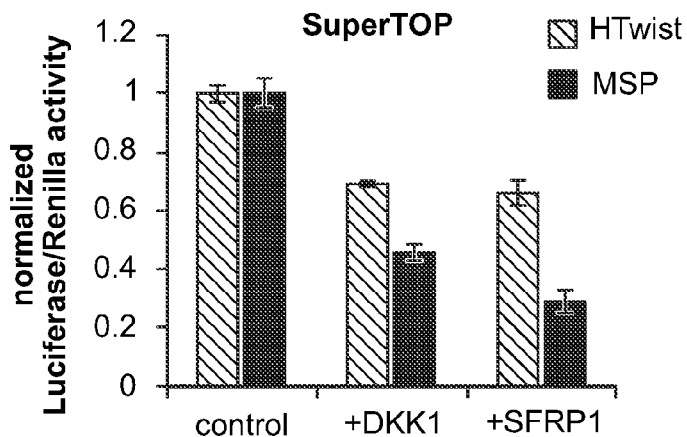

To determine changes in the activity of canonical, beta-catenin-dependent Wnt signaling, we utilized the TOPFlash reporter assay (Veeman et al., 2003). These analyses revealed a 5-fold higher TOP (beta-catenin/TCF-LEF reporter) activity relative to FOP activity (a control plasmid with mutated TCF-LEF-binding sites) in HTwist cells, and a 10- to 20-fold higher TOP/FOP activity in the two MSP lines (FIG. 2I). In contrast, beta-catenin/TCF-LEF transcriptional activity was undetectable in the HMLE$^{24+}$ cells. These observations demonstrated that beta-catenin-dependent, canonical Wnt signaling is active in HTwist and MSP cells but not in the HMLE$^{24+}$ cells. The observed downregulation of Wnt antagonists appears to be necessary for beta-catenin/TCF-LEF transcriptional activity: addition of either recombinant DKK1 or SFRP1 resulted in 1.5 to 2-fold reduction of TOPFlash reporter activity in the HTwist or MSP cells, respectively (FIG. 2J). Indeed, expression of DKK1 and SFRP1 has been shown to be a rate-limiting determinant of autocrine Wnt signaling in certain breast cancer cell lines (Bafico et al., 2004; Suzuki et al., 2004). When taken together with our earlier observations, these experiments indicated that autocrine signaling through the canonical and non-canonical Wnt pathways as well as the TGF-beta pathway, was enabled in HTwist and MSP cells, at least in part through significant downregulation of secreted antagonists of these three pathways (FIG. 9D).

Example 5

Autocrine Signaling Controls Migration and Mammosphere Formation of HTwist and MSP Cells While autocrine signaling through Wnt and TGF-beta pathways was active in HTwist and MSP cells, it remained unclear whether ongoing autocrine signaling through these pathways was required to maintain the functional properties of these cells. Accordingly, we determined whether continued expression of two EMT-associated cell-biological traits depended on such autocrine signaling: the abilities to migrate and to form mammospheres. The latter trait serves as an in vitro measure of anchorage-independent survival and growth as well as self-renewal (Dontu et al., 2003; Pece et al., 2010; Yu et al., 2007). For this purpose, we added back to cultured HTwist and MSP cell cultures several of the secreted inhibitory factors that we had found were downregulated in these cells relative to HMLE$^{24+}$ cells.

Figure 3B:
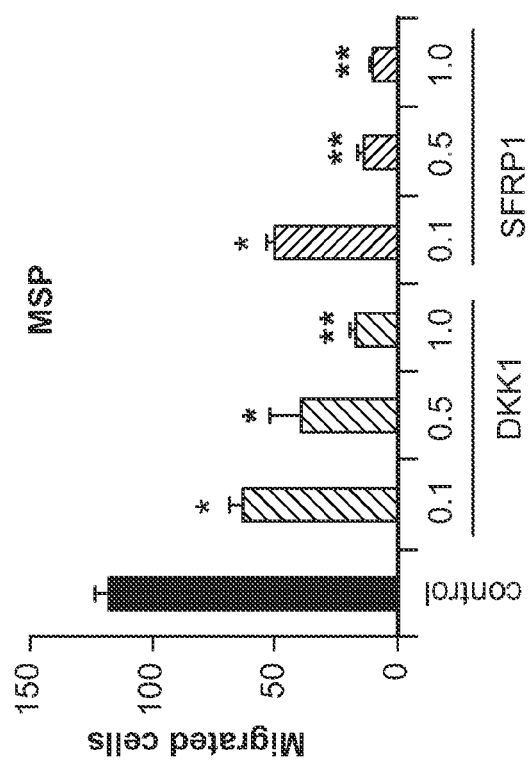
Figure 3A:
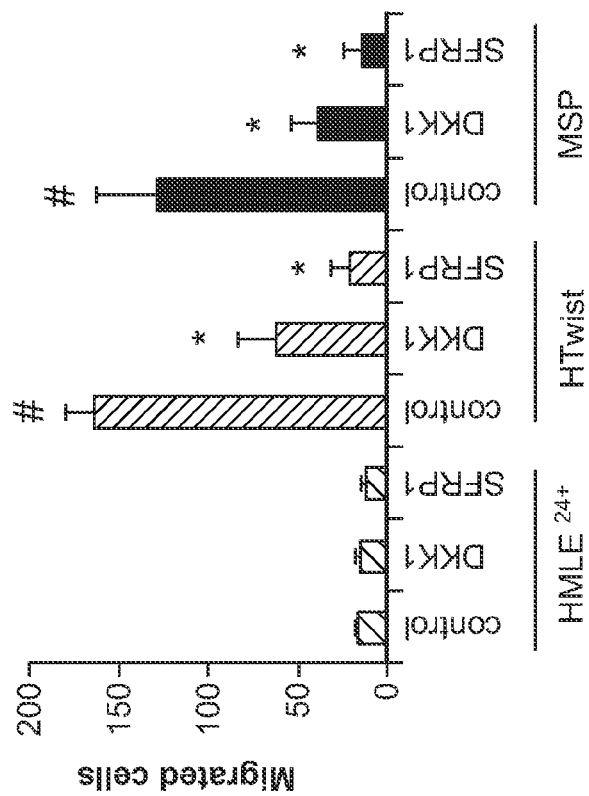
Figure 3C:
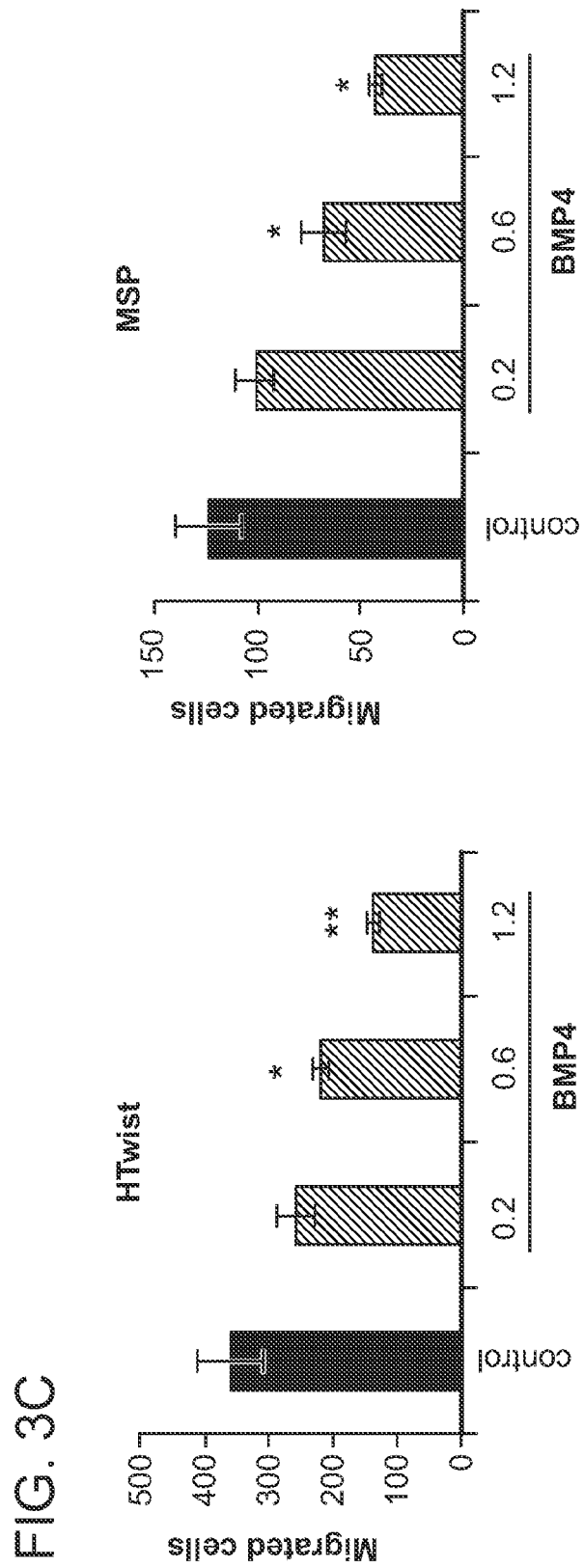
Figure 10A:
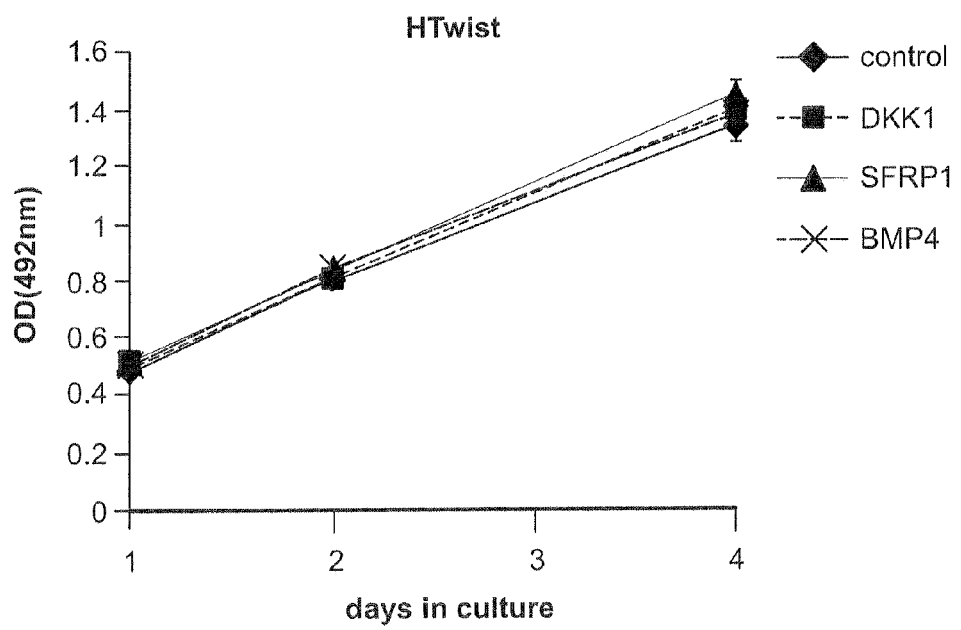
Figure 10A:
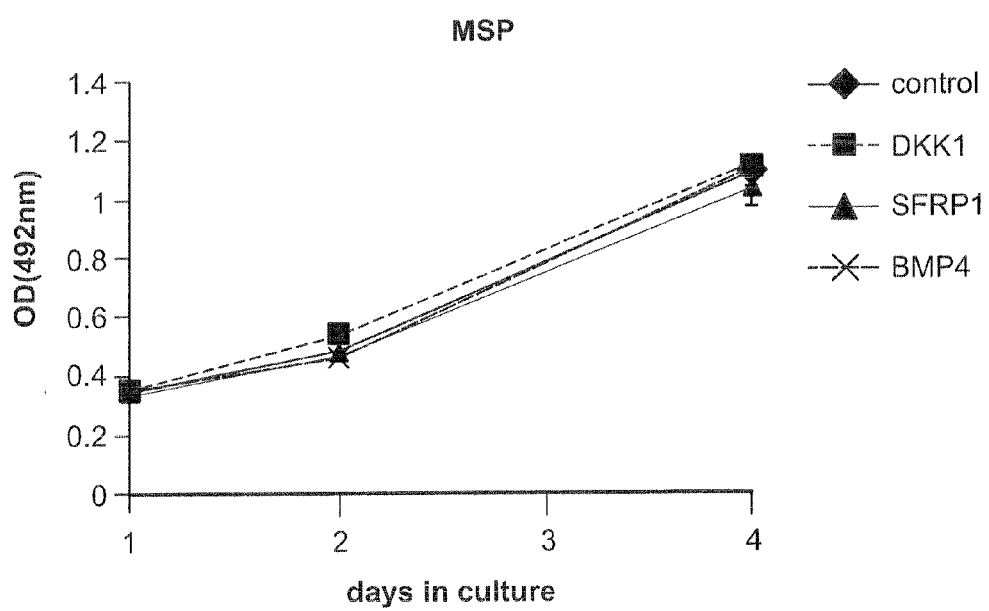
Figure 10B:
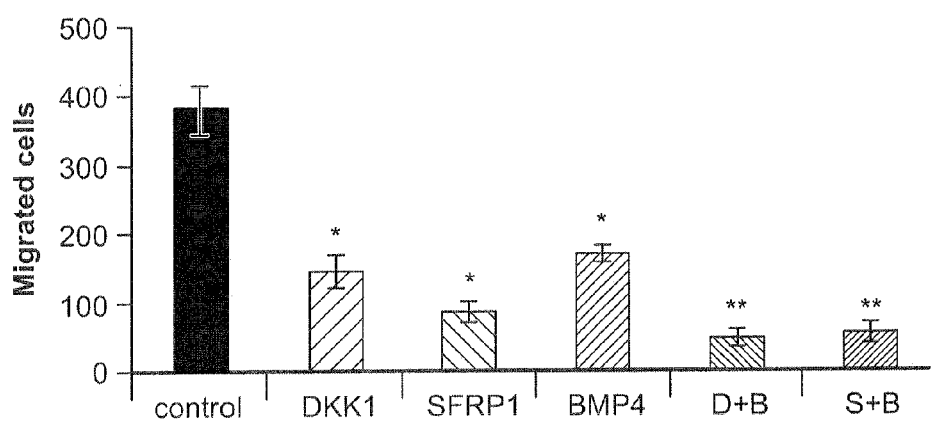

Relative to the HTwist and MSP cells, HMLE$^{24+}$ cells showed a 10-fold lower ability to migrate in vitro. This marginal motility was not further reduced upon addition of either recombinant DKK1 or SFRP1 protein (FIG. 3A). In contrast, addition of either DKK1 or SFRP1 to the culture medium of HTwist and MSP cells inhibited their migration in a dose-dependent manner (FIGS. 3A and 3B). At the highest concentration, recombinant DKK1 reduced migration 10-fold, while SFRP1 reduced the motility of these cells by a factor of 20 (FIGS. 3A and 3B). Recombinant BMP4 had a less potent effect on migration, inducing a maximum 2-fold reduction in HTwist or MSP cells (FIG. 3C). Importantly, proliferation of adherent cultures of HMLE$^{24+}$, HTwist and MSP cells was not affected by the presence of any of these recombinant proteins, excluding general cytostatic and cytotoxic effects of these agents (FIG. 10A).

We also tested the respective abilities of DKK1, SFRP1 and BMP4 to inhibit mammosphere formation in HTwist and MSP cells. When added daily for a period of 5 days beginning from the time of initial seeding of these cultures, recombinant DKK1 reduced the number of mammospheres that formed by 40% in HTwist and by 20% in MSP cells (FIG. 3D). When cells from the initially formed mammospheres were dissociated and re-introduced into secondary mammosphere cultures in the absence of further DKK1 treatment, we found that both cell lines exhibited a reduction in secondary sphere-forming ability by 25% (FIG. 3F). Since secondary mammospheres were seeded in the absence of further treatment, these results indicated a significant, albeit modest, reduction in the sub-populations of cells with self-renewal ability. SFRP1 had a more potent effect on primary and secondary mammosphere formation than DKK1: added SFRP1 protein reduced primary mammosphere formation of HTwist and MSP cells by 50% and 40%, respectively, and secondary sphere formation by 90% and 80% (FIGS. 3D and 3E). Recombinant BMP4 reduced primary mammosphere formation by 60% and inhibited secondary sphere formation by 90% (FIGS. 3D and 3E). Taken together, these data indicated that SFRP 1 and BMP4, and to a lesser extent DKK1, inhibit both migration as well as self-renewal in mammosphere cultures.

Figure 10C:
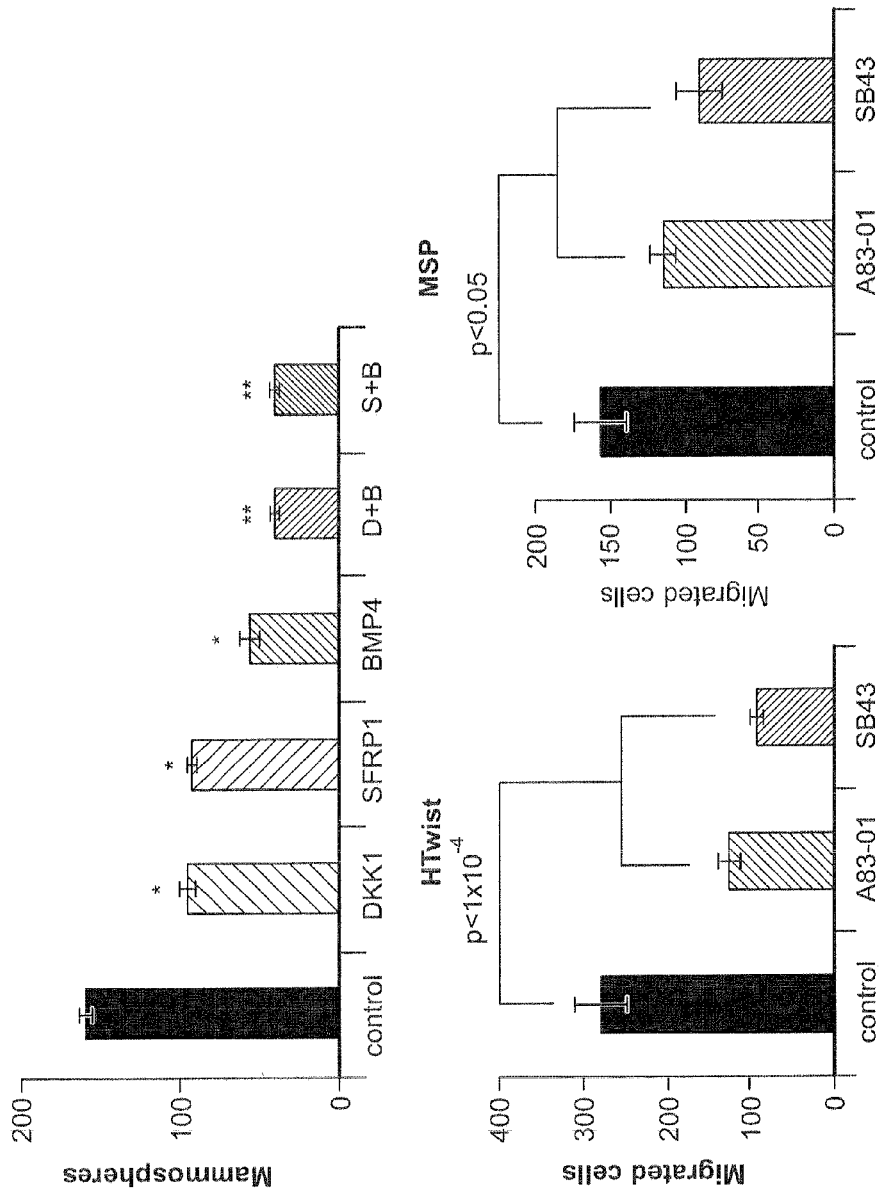

Adding either DKK1 or SFRP1 in combination with BMP4 to HTwist cells had an additive effect on migration (8- and 7-fold respectively, compared to 3-, 5- and 2-fold when added individually, FIG. S3B). During primary mammosphere formation, we observed a 74% reduction in sphere-forming efficiency when DKK1 or SFRP1 were added together with BMP4 (FIG. 10C). This compared to 40% reduction when DKK1 and SFRP1 were added singly, and a 64% reduction when BMP4 was added singly (FIG. 10C). These responses suggested that the three agents work, at least in part, through distinct downstream pathways and reinforce the notion that maintenance of migration and self-renewal abilities is dependent on the combined activation and continuous signaling of autocrine Wnt signaling pathways as well as the inactivation of BMP signaling.

Figure 10D:
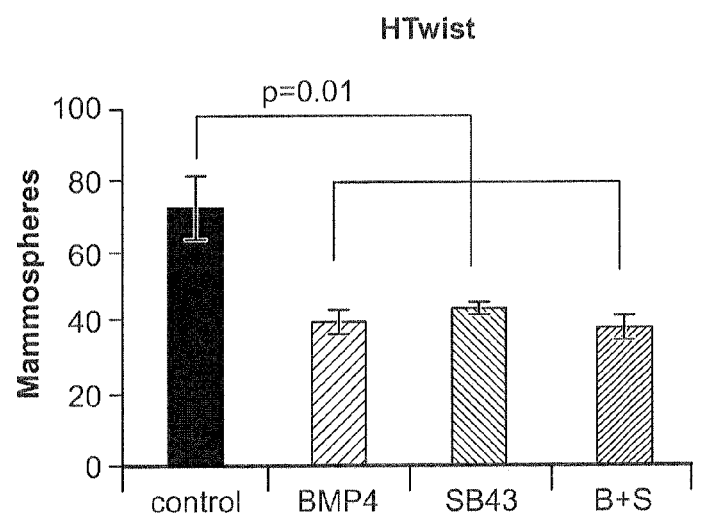
Figure 10D:
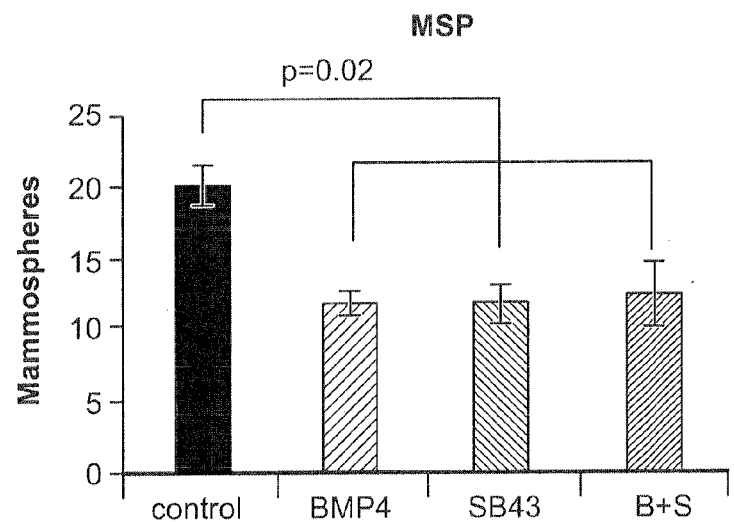

We note that inhibition of autocrine TGF-beta signaling by inhibitors specific for the TGF-beta Receptor Type I (A83-01 and SB431542) attenuated migration and mammosphere formation of HTwist and MSP cells to a similar extent as added BMP4 protein (FIGS. 10D and 10E). However, the combination of these two agents did not have an additive effect (FIGS. 10D and 10E), suggesting that BMP4 exerts most of its inhibitory effects by interfering with TGF-beta signaling. Together, these data suggested that maintenance of migration and self-renewal ability by ongoing autocrine TGF-beta signaling in HTwist and MSP depends on concomitant reduction of BMP signaling.

Example 6

Autocrine Signaling Controls Tumorigenicity and Metastasis of MSP-RAS Cells

Figure 11:
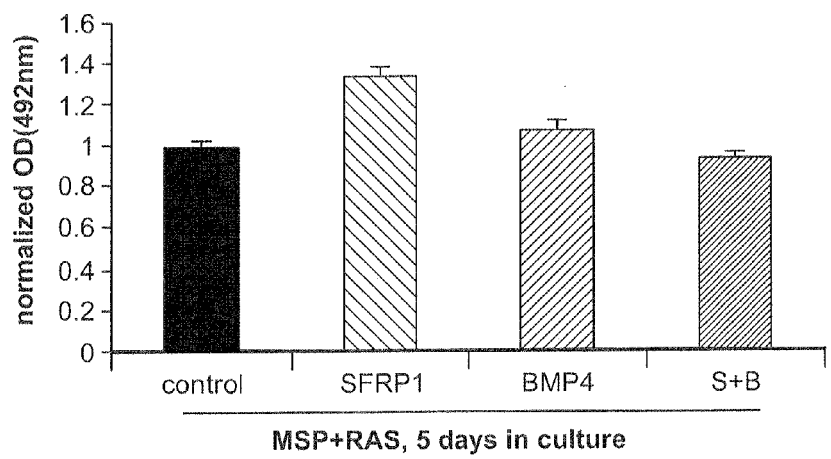
FIG. 11. Proliferation Assay. MSP-RAS cells were treated daily for 5 days with SFRP1 (1 µg/ml), BMP4 (0.5 µg/ml), protein or a combination of both, cumulative proliferation was measured by the MTS assay, n=6.

After establishing a role for autocrine signaling in controlling migration and self-renewal abilities of immortalized, non-tumorigenic MSP cells, we wished to determine whether their transformed derivatives—the MSP-RAS cells—employ similar regulatory loops to maintain tumorigenic and metastatic behavior. Similar to their immortalized counterparts, MSP-RAS cells remained sensitive to inhibition of migration and tumorsphere formation by SFRP1 or BMP4, the latter trait gauging anchorage-independent proliferation of transformed cells at clonal densities. Exposure of MSP-RAS cells to recombinant SFRP1 led to a 9-fold decrease of motility in vitro, while BMP4 treatment yielded a 4-fold inhibition of migration (FIG. 4A). The combination treatment of these cells with SFRP1 and BMP4 inhibited migration synergistically by 30-fold (FIG. 4A). Importantly, proliferation of MSP-RAS cells was unaffected by the presence of these recombinant proteins, once again excluding non-specific cytostatic and cytotoxic effects (FIG. 11).

When MSP-RAS cells were treated with recombinant SFRP1 and BMP4 during primary tumorsphere formation, both primary and secondary sphere formation were reduced by 40% by each factor added alone, and by 60% when SFRP1 and BMP4 were added in combination (FIG. 4B). Inhibition of secondary tumorsphere formation suggested a long-term loss of self-renewal abilities upon treatment with SFRP1 and BMP4. Together, these data indicated that autocrine signaling continues to control migration and self-renewal ability, as gauged by tumorsphere formation, in MSP cells following transformation with the RAS oncogene. Similar to their immortalized, untransformed precursors, these properties of MSP-RAS could be perturbed by exposing them to naturally occurring, secreted signaling antagonists.

To test whether the observed attenuation of tumorsphere formation correlated with the loss of expression of cell-surface markers characteristic of tumor-initiating cells (Al-Hajj et al., 2003), we conducted flow cytometry to analyze the CD44/CD24 cell-surface marker profile of MSP-RAS primary tumorspheres. We found that MSP-RAS control tumorspheres contained only a small fraction of CD24-positive cells (6.4%, FIG. 4C), with the majority displaying the CD44high/CD24low-negative profile that is associated with cell populations enriched for tumor-initiating ability. In contrast, in the smaller number of primary tumorspheres that formed in the presence of either SFRP 1 or BMP4, we observed an increase of CD24-positive cells from 6.4% to 40%, and to 43% in cells treated with both SFRP1 and BMP4 (FIG. 4C). However, most of these cells continued to express CD44, with only a minority changing to a CD44low-negative/CD24positive profile. Therefore, while indicative of a possible differentiation-like process, changes in expression of these cell-surface markers upon treatment did not closely correlate with the degree of tumorsphere inhibition.

Figure 4D:
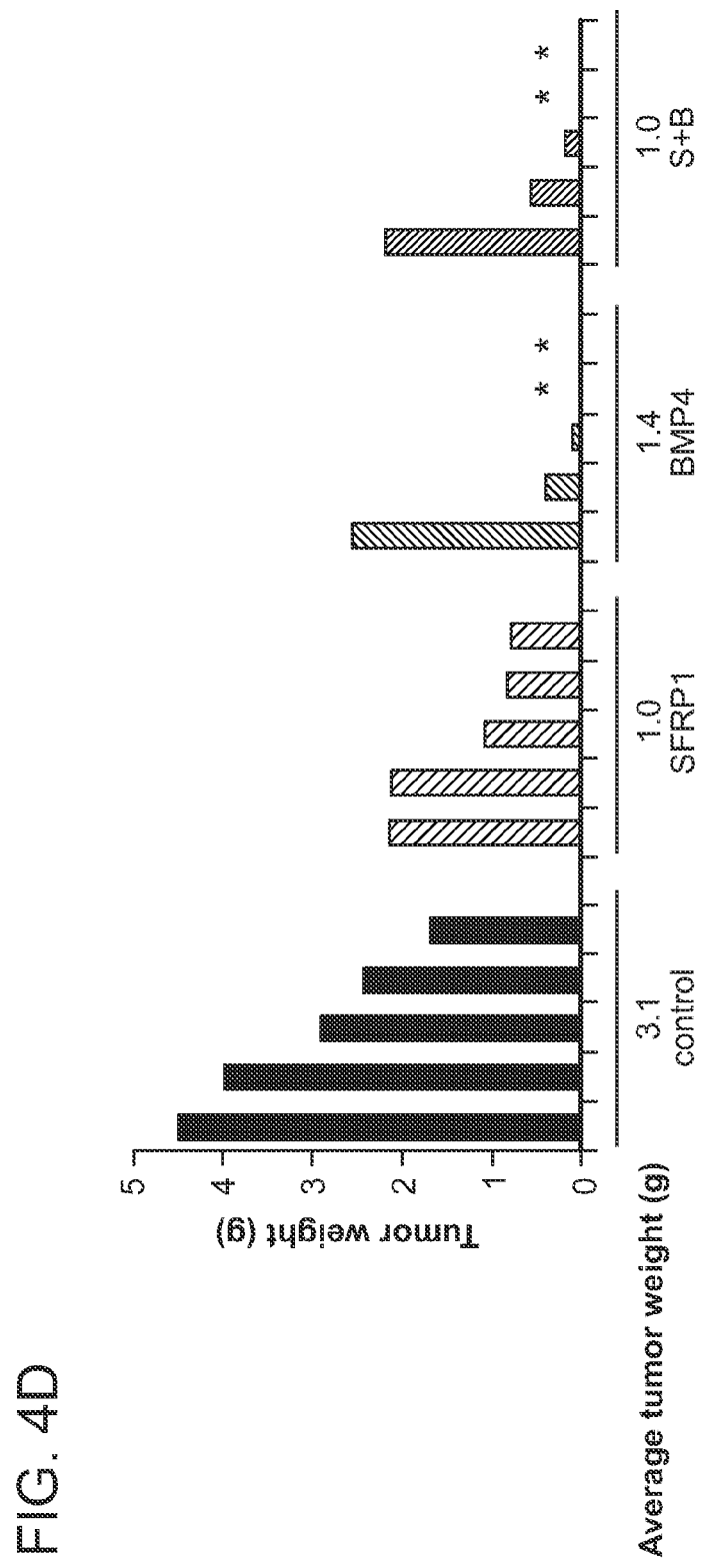

We also wished to determine whether in vitro exposure to SFRP1 and BMP4 influenced subsequent in vivo behavior of MSP-RAS cells. For this purpose, we prepared single-cell suspensions from primary control MSP-RAS tumorspheres or from the residual tumorspheres that had formed during a 5 day in vitro treatment with SFRP1, BMP4 or a combination of both. Following injection of these populations into the mammary fat pads of mice, we noted that the tumors that originated from mammospheres of MSP-RAS cells that had been exposed ex vivo to either SFRP1, BMP4 or a combination of both were reduced in weight by 3-fold on average (FIG. 4D). However, we only observed a modest reduction in tumor incidence for the BMP4 and combination-treated groups (30%, FIG. 4D). These data suggested that a sufficient number of tumor-initiating cells remained within the treated tumorspheres to give rise to tumors that were, however, compromised in their ability to vigorously proliferate and/or survive in vivo as indicated by the reduction in tumor weight.

Figure 4E:
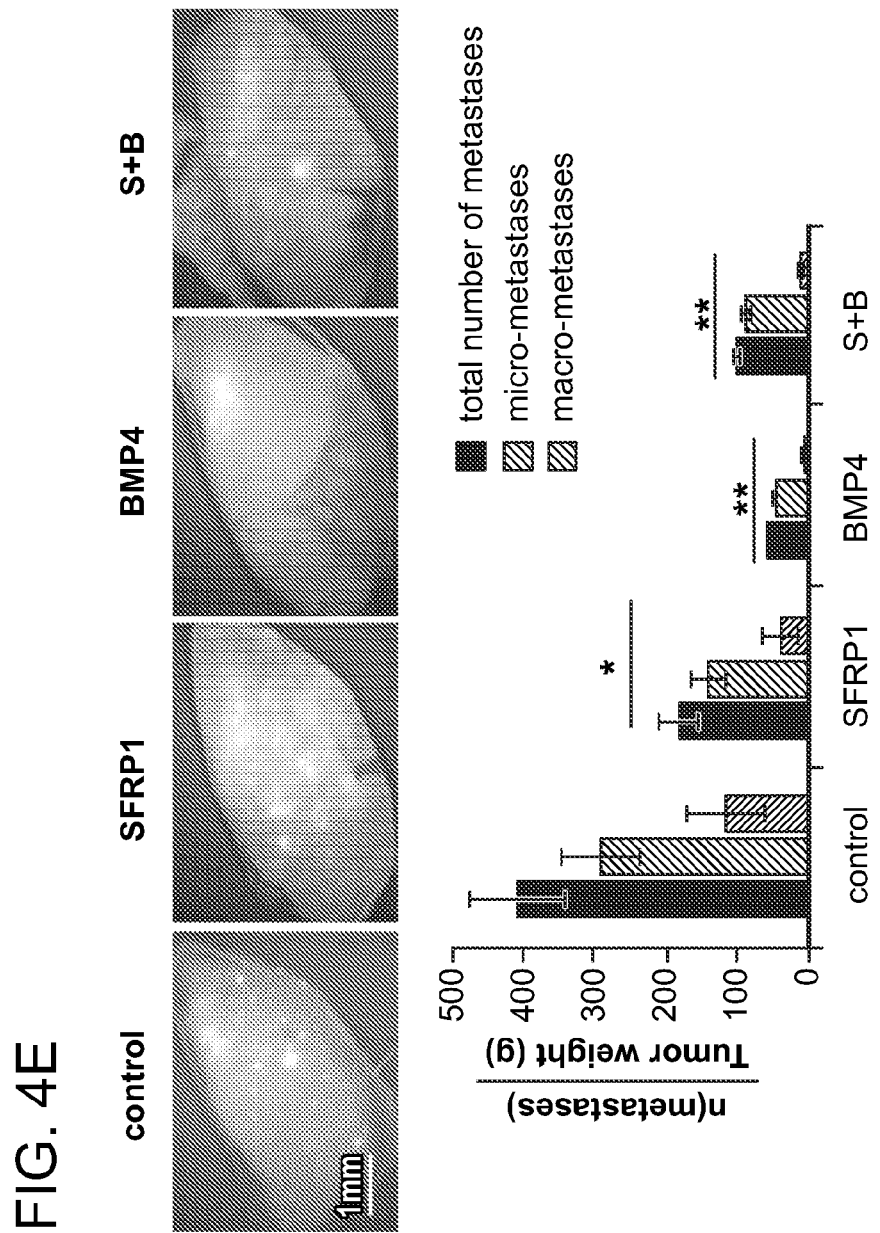
Figures 4F, 4G:
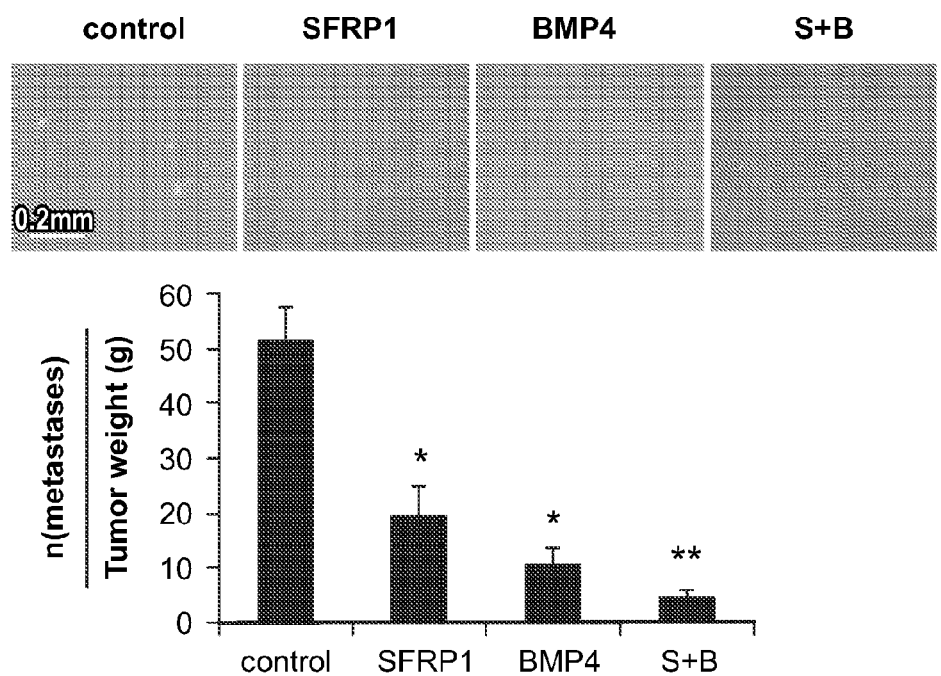

Further, we noted a significant reduction in lung and liver metastasis following orthotopic injection of ex vivo treated cells compared to control cells (FIGS. 4E and 4F). To account for the differences in primary tumor burden, we normalized the number of metastatic foci counted on the surfaces of the lungs and liver by the corresponding primary tumor weights. Using this metric, we observed a 2-fold reduction in lung metastases in the SFRP1-treated group, 7.5-fold in the BMP4, and 4.5-fold in the combination-treated group (FIGS. 4E and 4F). Echoing the effects on migration in vitro, combination treatment with SFRP1 and BMP4 had a synergistic effect on decreasing the number of metastatic foci in the liver, by >10-fold on average, compared to a 2.5- and 5-fold reduction in the mice that had been treated ex vivo either with SFRP1 and or BMP4 singly treated groups.

We speculated that the presence of recombinant SFRP1 and BMP4 during actual tumor-initiation might exert a stronger effect on MSP-RAS cells compared to the ex vivo pre-treatment we conducted previously. For this purpose, we implanted MSP-RAS cells subcutaneously in mice in limiting dilutions together with SFRP1, BMP4, and a combination of both (FIG. 4G). In addition, 20 µl of PBS or PBS containing recombinant proteins at indicated doses was injected peritumorally at 1, 2, 3 and 7 days after implanting the MSP-RAS cells. Doing so reduced tumor incidence by at least one order of magnitude for SFRP1, BMP4 or combination treatment (FIG. 4G), suggesting that the presence of either protein during tumor initiation was sufficient to perturb the tumorigenicity of MSP-RAS cells.

In summary, ex vivo treatment of MSP-RAS cells with BMP4 and SFRP1 perturbed the ability of these cells to proliferate vigorously in vivo and subsequently give rise to metastases from an orthotopic implantation site. Furthermore, in vivo delivery of BMP4 and SFRP1 attenuated the ability of MSP-RAS cells to initiate tumors. Taken together with the earlier observations, these data indicated that ongoing autocrine signaling plays an important role in maintaining biological properties of immortalized, non-tumorigenic cells that reside in a mesenchymal and SC-like state as well as the corresponding traits of their transformed derivatives.

Example 7

Creation of a Permissive Extracellular Environment Allows TGF-beta to Initiate an EMT We wished to determine whether the signaling channels involving Wnt and TGF-beta pathways serve only to maintain migratory and self-renewal abilities, or whether they might also function to induce the initial entrance of epithelial cells into a mesenchymal and SC-like state. To begin, we investigated whether the same protein ligands that functioned in an autocrine manner in HTwist and MSP cells could be applied to $HMLE^{24+}$ cells to induce an EMT.

As an early and specific readout for activation of the EMT program, we monitored expression of the Zeb1 and Zeb2 EMT-TFs, because their mRNA expression was nearly absent in parental $HMLE^{24+}$ cells, but highly upregulated in HTwist and MSP cells (FIG. 1A). In contrast, other EMT-TFs were already expressed at significant levels in HMLE$^{24+}$ cells (Twist) or regulated post-translationally (Snail, Slug, FIG. 1B-1D). In addition, we measured expression of the mesenchymal marker N-cadherin, whose expression we found nearly absent in HMLE$^{24}$ cells (FIGS. 1B and 1D).

Figure 5A:
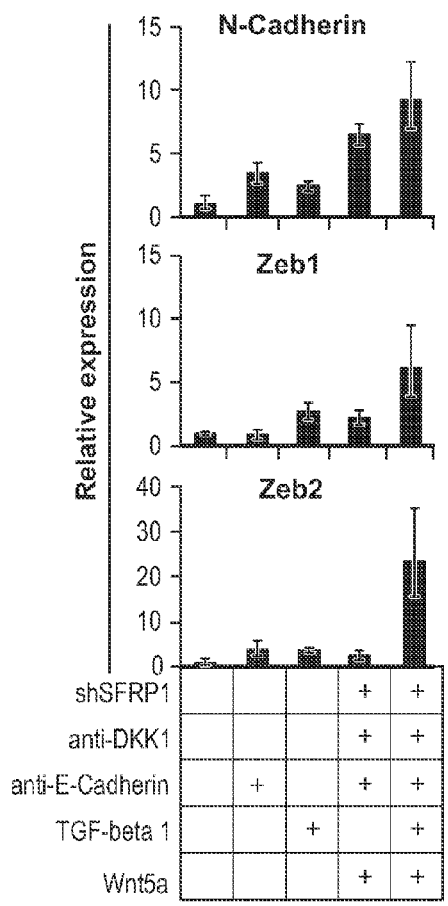
FIGS. 5A-5H. Concomitant stimulation of Wnt and TGF-beta pathways allows HMLE$^{24+}$ cells to enter into a mesenchymal and SC-like state.
Figure 12A:
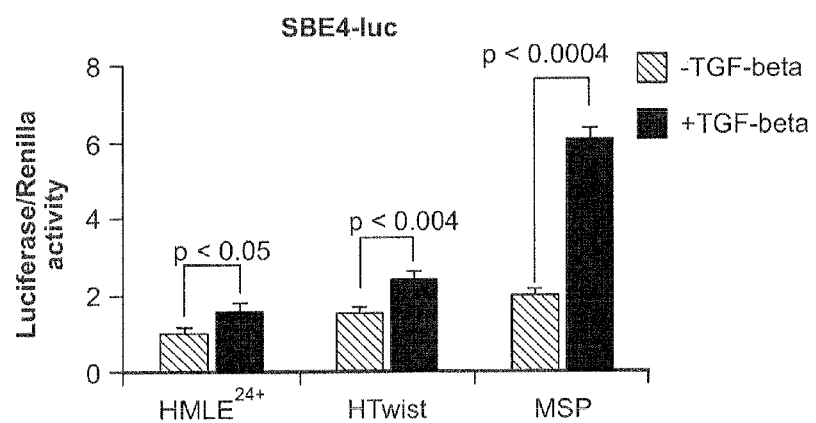

To begin, we attempted to induce an EMT in HMLE$^{24+}$ cells through exposure to TGF-beta, one of the three signaling factors that our prior experiments had implicated in maintenance of EMT-associated properties. Though TGF-beta was historically the first extracellular factor reported to induce an EMT (Oft et al., 1998), treatment of HMLE$^{24+}$ cells for a period of 3 days with recombinant TGF-beta 1 did not result in a significant induction of either N-Cadherin, Zeb1 or Zeb2 (FIG. 5A). Of note, the latter have been described as targets of TGF-beta signaling (Shirakihara et al., 2007). This lack of responsiveness was not due to an inability to process TGF-beta signals, since Smad-reporter assays demonstrated a modest upregulation of activity when HMLE$^{24+}$ cells were treated with TGF-beta (1.5-fold, FIG. 12A). Additionally, these data suggested that the amount of added TGF-beta sufficed to overwhelm any inhibitory signals from BMP ligands normally produced by HMLE$^{24+}$ cells.

Figure 12B:
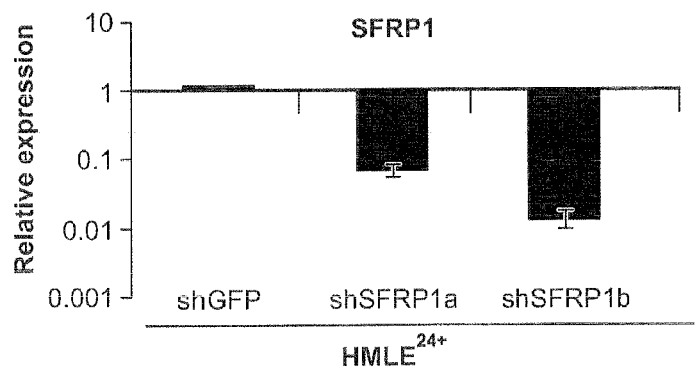
Figure 12C:
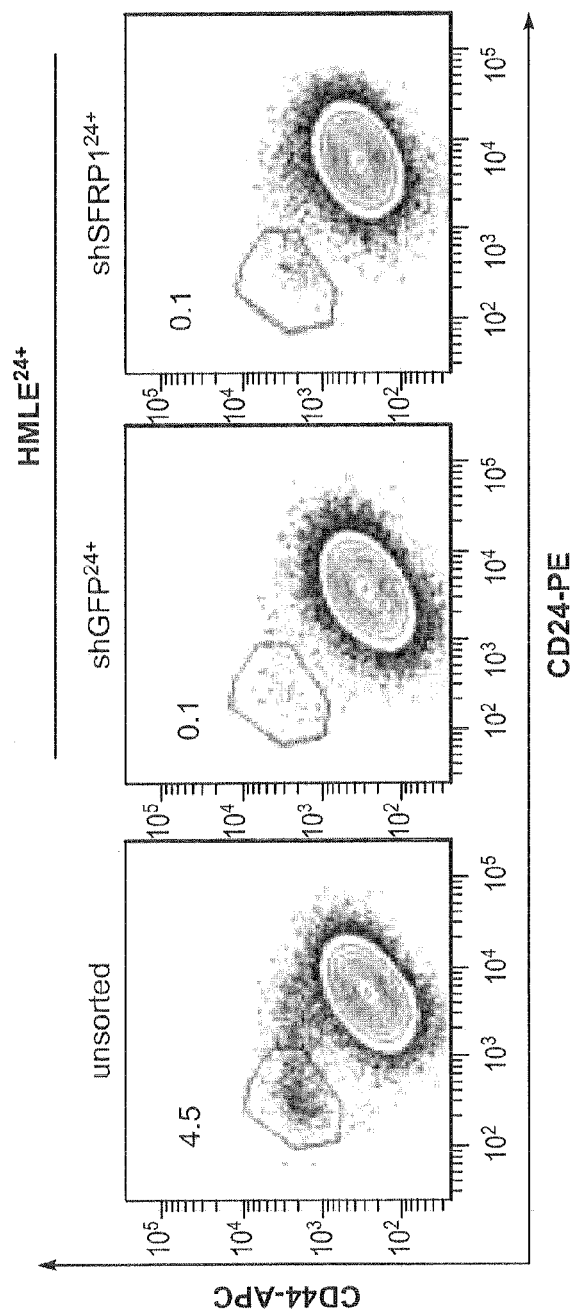

To explore the contributions of additional, collaborating signaling pathways to EMT induction, we investigated the effects of the following modulators, added singly or in combination to HMLE$^{24+}$ cells:

1) Unblocking of autocrine Wnt signaling in HMLE$^{24+}$ cells. Since SFRP1-neutralizing antibodies were not available, we knocked down expression of the SFRP1-encoding mRNA in HMLE$^{24+}$ cells using lentiviral vectors expressing small hairpin (sh)RNAs (FIGS. 12B and 12C). To complement this reduction of Wnt inhibition, we used an anti-DKK1-neutralizing antibody in combination with the shRNAs.

2) Addition of Wnt5a. Since Wnt5a was among the three non-canonical Wnt ligands upregulated in HTwist and MSP cells, we added recombinant Wnt5a to cultures of HMLE$^{24+}$ cells.

3) Promotion of cell scattering. Previously, we and others had noted that cells at the outer edges of epithelial islands lose some of their epithelial characteristics, presumably because they are unable to form cell-cell junctions on all sides (Godar et al., 2008; Savagner et al., 2005; Zavadil et al., 2001). Hence, as an additional potential EMT-inducing signal, we blocked the formation of adherens junctions through the addition of an anti-E-cadherin monoclonal antibody to the cultured cells.

To summarize the effects of these agents, compared to single factors or various combinations (FIG. 5A), only addition of all these EMT-inducing components together with TGF-beta led to a significant induction of both Zeb1 (6-fold) and Zeb2 (25-fold) as well as N-Cadherin RNA expression (9-fold, FIG. 5A). Hence, disinhibition of the canonical Wnt pathway, activation of non-canonical Wnt signaling, and perturbation of adherens junction formation, collaborate with the TGF-beta pathway to induce expression of EMT-TFs. Hereafter, we refer to this induction cocktail, employed with concomitant knockdown of SFRP1 expression, as "iEMT".

Example 8

Figure 5C:
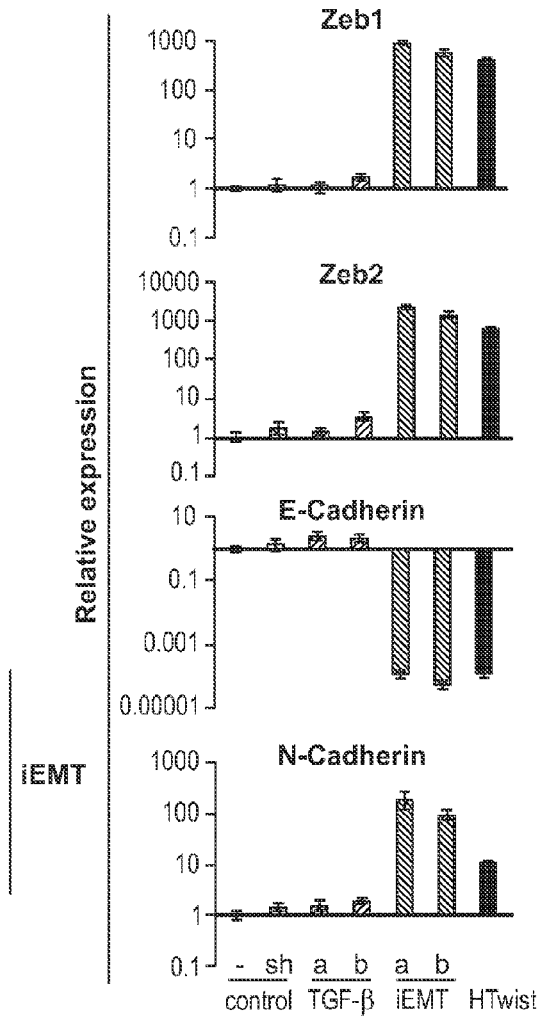
Figure 5B:
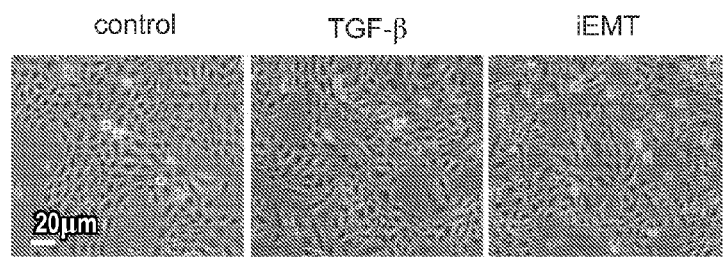
Figure 5D:
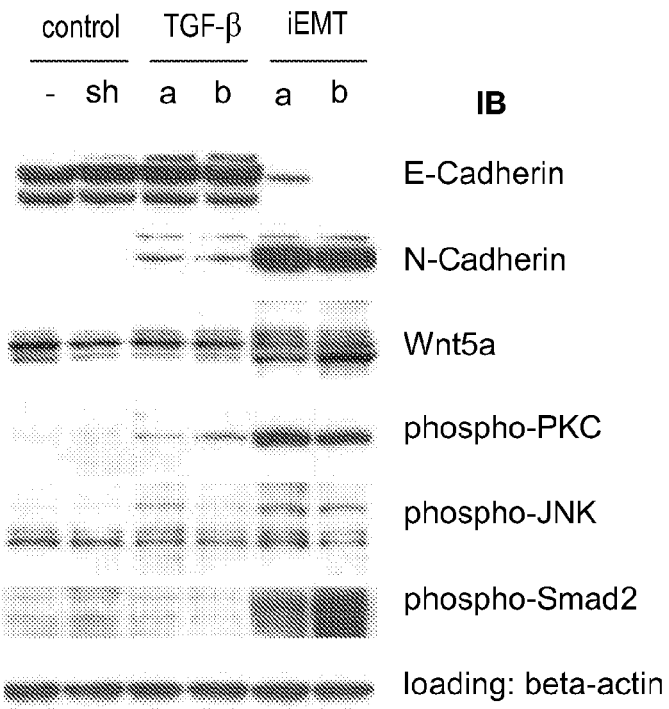

Concomitant Stimulation of Wnt and TGF-beta Pathways Allows HMLE$^{24+}$ Cells to Enter into a Mesenchymal and SC-Like State It remained unclear whether the EMT program triggered by the iEMT cocktail would yield cells that entered stably into the mesenchymal and SC-like state. To investigate this possibility, we treated two cultures of HMLE$^{24+}$-shGFP cells independently with TGF-beta alone and two cultures of HMLE$^{24+}$-shSFRP1 cells with the iEMT cocktail over a period of 14 days. We compared their response to untreated HMLE$^{24+}$-shGFP and -shSFRP1 control cells. Three days after the first treatment, pronounced cell scattering and dispersal of epithelial islands was only observed in the iEMT-cultures (FIG. 12D). Over a period of 14 days, these cells acquired a mesenchymal morphology characterized by single, front-to-end polarized cells (FIG. 12D). Following cessation of further treatment after these 14 days, iEMT-cells did not revert back to an epithelial phenotype, at least for 12 subsequent passages (~36 population doublings) in tissue culture (FIG. 5B, FIG. 12D). In these phenotypically stable iEMT-cells, we observed a switch from E- to N-Cadherin expression (FIGS. 5C and 5D, Thiery and Chopin, 1999). In contrast, cells that had been treated with TGF-beta only (TGF-beta-cells) displayed a marginal upregulation of N-Cadherin, but E-Cadherin levels remained robust (FIGS. 5C and 5D). Repression of E-Cadherin has been shown to be a rate-limiting step for induction of certain EMTs (Onder et al., 2008). RT-PCR analysis of EMT-TFs Zeb1, Zeb2 and Twist provided further evidence that iEMT-treated cells had moved stably into a mesenchymal state: these were all upregulated >100-fold compared to untreated control and TGFb-cells (FIG. 5C).

Figure 12E:
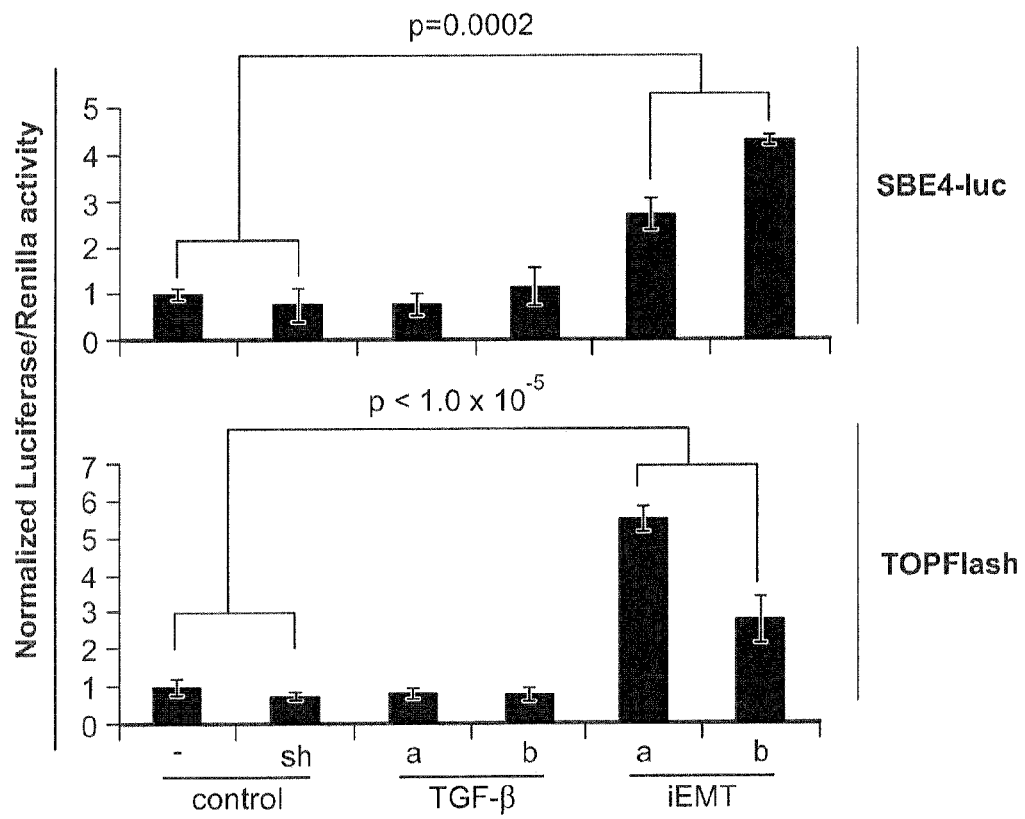
Figure 12F:
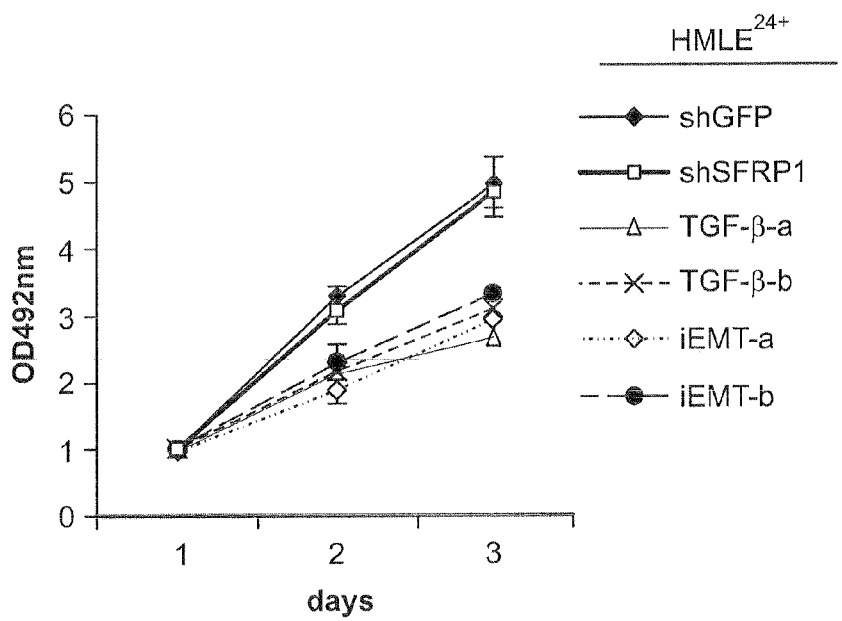

In addition, as indications of ongoing autocrine TGF-beta signaling, we observed a 3- to 4-fold increase in Smad-reporter activity (FIG. 12E) and readily detectable Smad2 phosphorylation in iEMT-cells, all relative to control and TGF-beta treated-cells (FIG. 5D). We also detected increased levels of Wnt5a that were paralleled by elevated phosphorylation of PKCs and JNK, indicative of autocrine non-canonical Wnt signaling in these cells (FIG. 5D). We measured a 4-fold increase in beta-catenin/TCF-LEF reporter activity, which is indicative of canonical Wnt signaling (FIG. 12E). We concluded that stable maintenance of an EMT was accompanied by the establishment of autocrine signaling loops involving the same factors that had previously triggered entrance into an EMT.

Figure 5E:
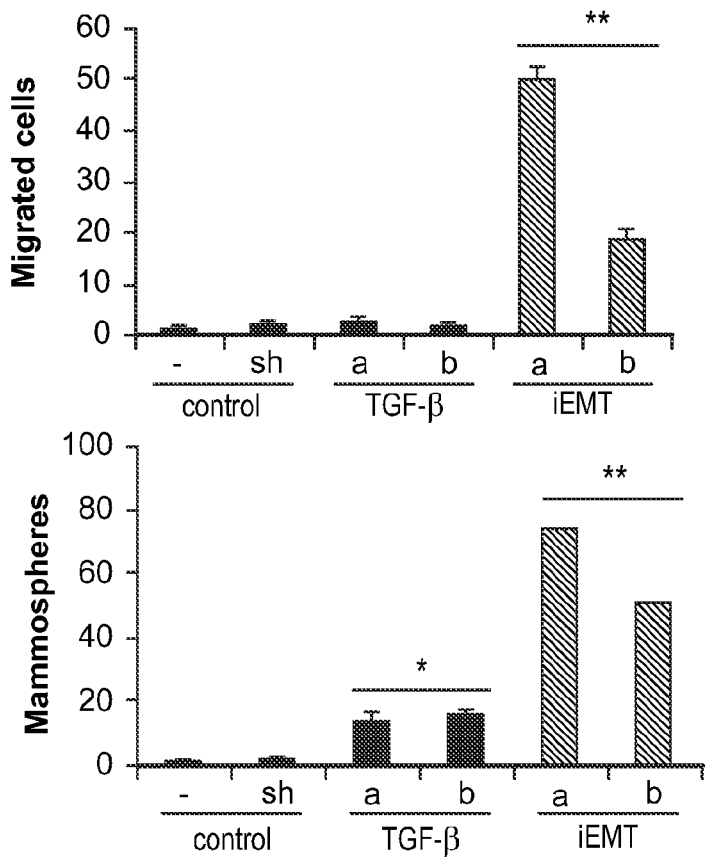
Figure 5F:
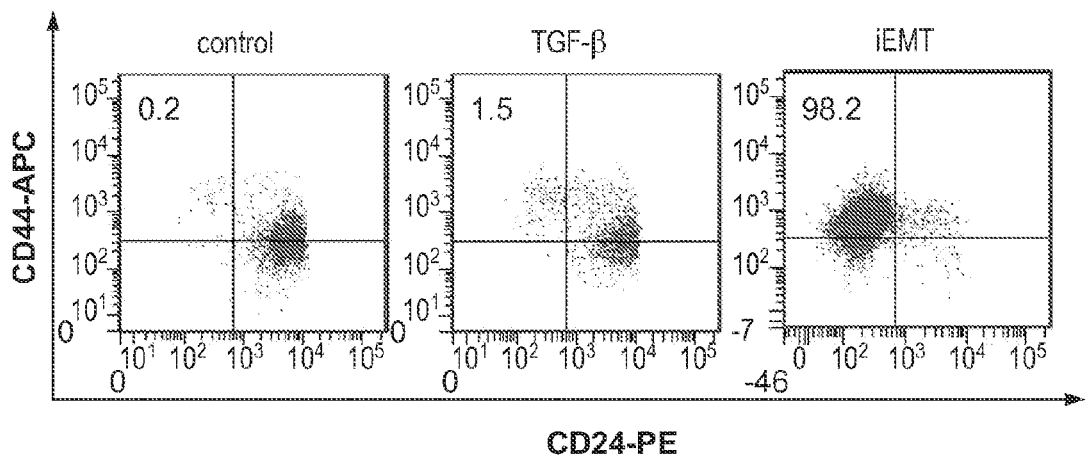
Figure 5G:
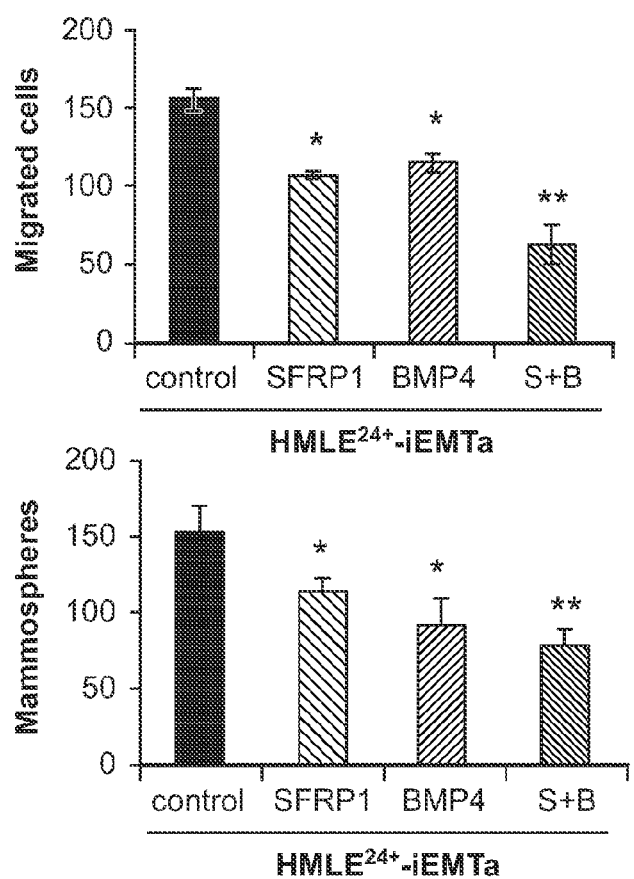

We also examined whether the stable induction of a mesenchymal phenotype was accompanied by the acquisition of self-renewal ability. Compared to untreated control cells, iEMT-cells formed 70 times more mammospheres and their ability to migrate increased 50-fold (FIG. 5E). In contrast, TGF-beta-cells displayed a significant, but smaller increase in mammosphere-forming efficiency (10-fold) but not in motility. Echoing these results, we observed a comparably small increase in the proportion of CD44high/CD24low-negative cells in TGF-beta-treated cells (from 0.2% to 1.5%) compared to the 98% representation of CD44 high/CD24 low-negative cells in iEMT-treated cells, FIG. 5F). Importantly, these effects could not be attributed to a difference in proliferation rates between iEMT-, TGF-beta and control cells; indeed, proliferation rates in adherent monolayer cultures were stably lower in TGF-beta- or iEMT-cells (FIG. 12G). Of note, the iEMT-cells remained sensitive to perturbation of their autocrine environment: treatment of these cells with recombinant SFRP1, BMP4 or a combination of both inhibited migration and mammosphere formation to an extent comparable to that of HTwist and MSP cells (FIG. 5G).

Figure 5H:
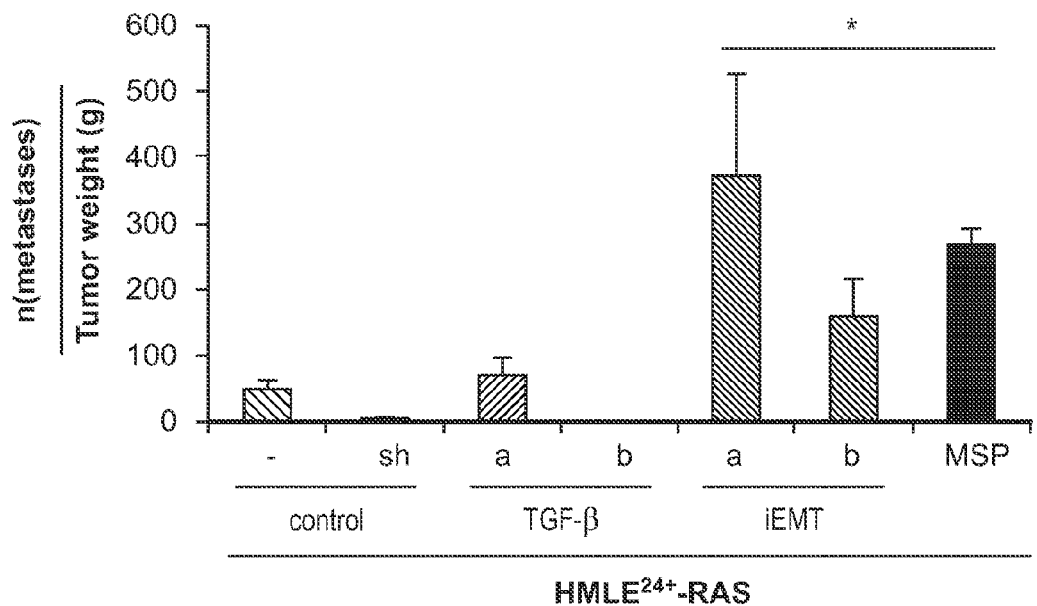

We also obtained evidence that the mesenchymal and SC-like state of cells treated with the iEMT-cocktail was maintained after such cells passed through the process of cell transformation. Thus, when these various cell populations were transformed with the RAS oncogene, only the iEMT-cells, implanted into the mammary fat pads of mice, gave rise to lung metastatic foci with a similar elevated frequency as MSP-RAS cells. In contrast, RAS-transformed control HMLE cells and the corresponding TGF-beta-treated population were only weakly metastatic (FIG. 5H).

Together, these findings indicated that the same factors involved in maintaining the mesenchymal and SC-like state can also serve as its inducers, allowing the derivation of cells with migratory and SC-like properties from populations that previously displayed these functional attributes at very low levels. The results also demonstrate the increased efficiency in eliciting these responses obtained through use of more than one factor.

Example 9

Figure 6A:
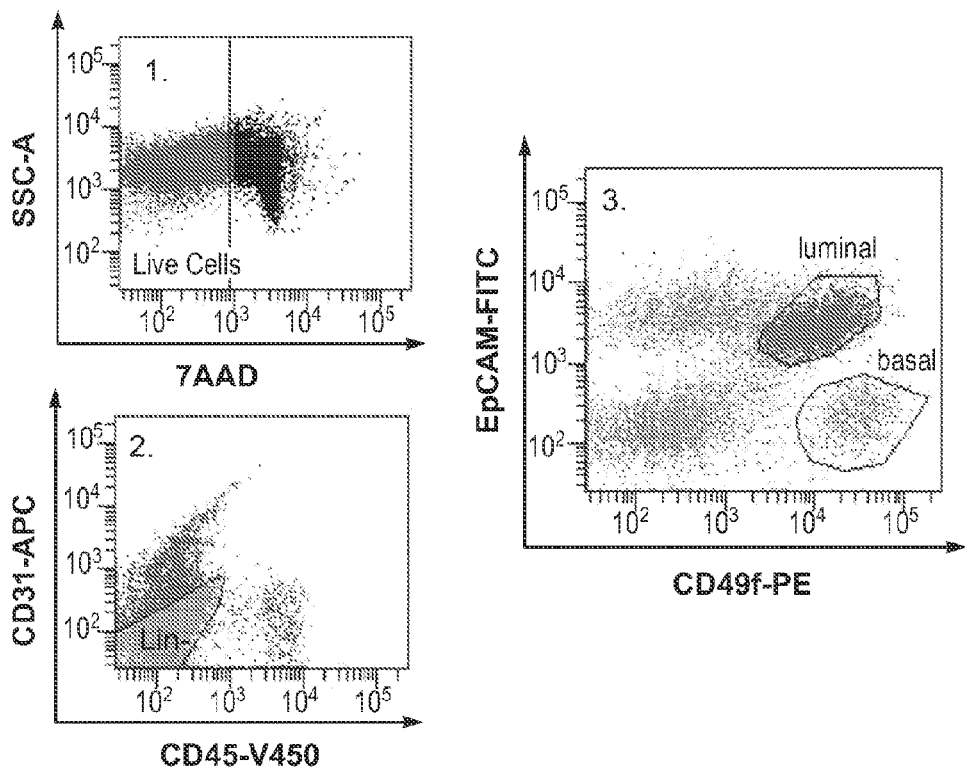
FIGS. 6A-6F. Basal cell populations isolated from human mammary gland express mesenchymal markers and EMT-TFs.

Basal Cell Populations Isolated from Human Mammary Gland Express Mesenchymal Markers and EMT-TFs To clarify whether the migratory and self-renewal traits of HTwist, MSP and HMLE$^{24+}$-iEMT cells reflected properties of certain cell populations residing within the normal mammary gland, we set out to identify populations of MECs from human mammary glands that were phenotypically similar to HMLE cells and their various mesenchymal and SC-like derivatives. To do so, we isolated and propagated in culture two distinct cell populations prepared from reduction mammoplasty tissue using recently reported cell-surface markers. Through FACS analyses we classified these populations as basal cells based on high expression of CD49f and low-or-absent expression of EpCAM, and as luminal lineage-restricted cells based on expression of CD49f and high levels of EpCAM (FIG. 6A, Eirew et al., 2008; Lim et al., 2009; Stingl et al., 2001). The presence of stem and bi-potent progenitor cells has been found to be restricted to basal cells (Eirew et al., 2008; Stingl et al., 2001).

We further characterized our sorted populations by a variety of previously described lineage markers (reviewed in Stingl, 2009; Visvader, 2009). As anticipated, the sorted luminal cells expressed lineage markers cytokeratin 8, 18 and MUC1, whereas sorted basal cells did not (FIG. 6C). Conversely, most basal cells expressed cytokeratin 14, while the great majority of luminal cells, with the exception of a few clusters, did not (FIG. 6D). Significantly, only basal cells displayed high levels of nuclear p63 (FIG. 6D), a functional marker of basal and stem cell populations in stratified epithelia (Senoo et al., 2007). Of note, we also observed some cells expressing alpha-smooth muscle actin, a marker of mature myoepithelial cells, exclusively within basal cultures (FIG. 6D). To summarize, we concluded that our cell sorts and subsequent propagation in monolayer cultures yielded highly purified populations of basal and luminal cells that continued to express appropriate markers.

Figure 6B:
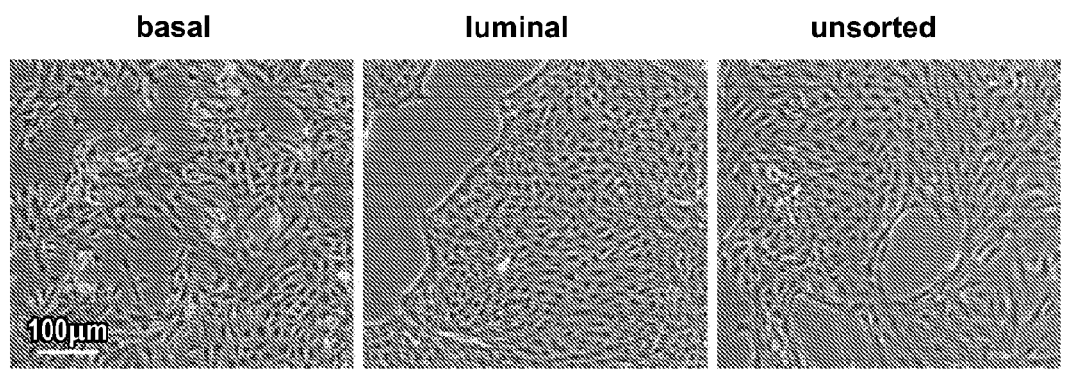
Figure 6C:
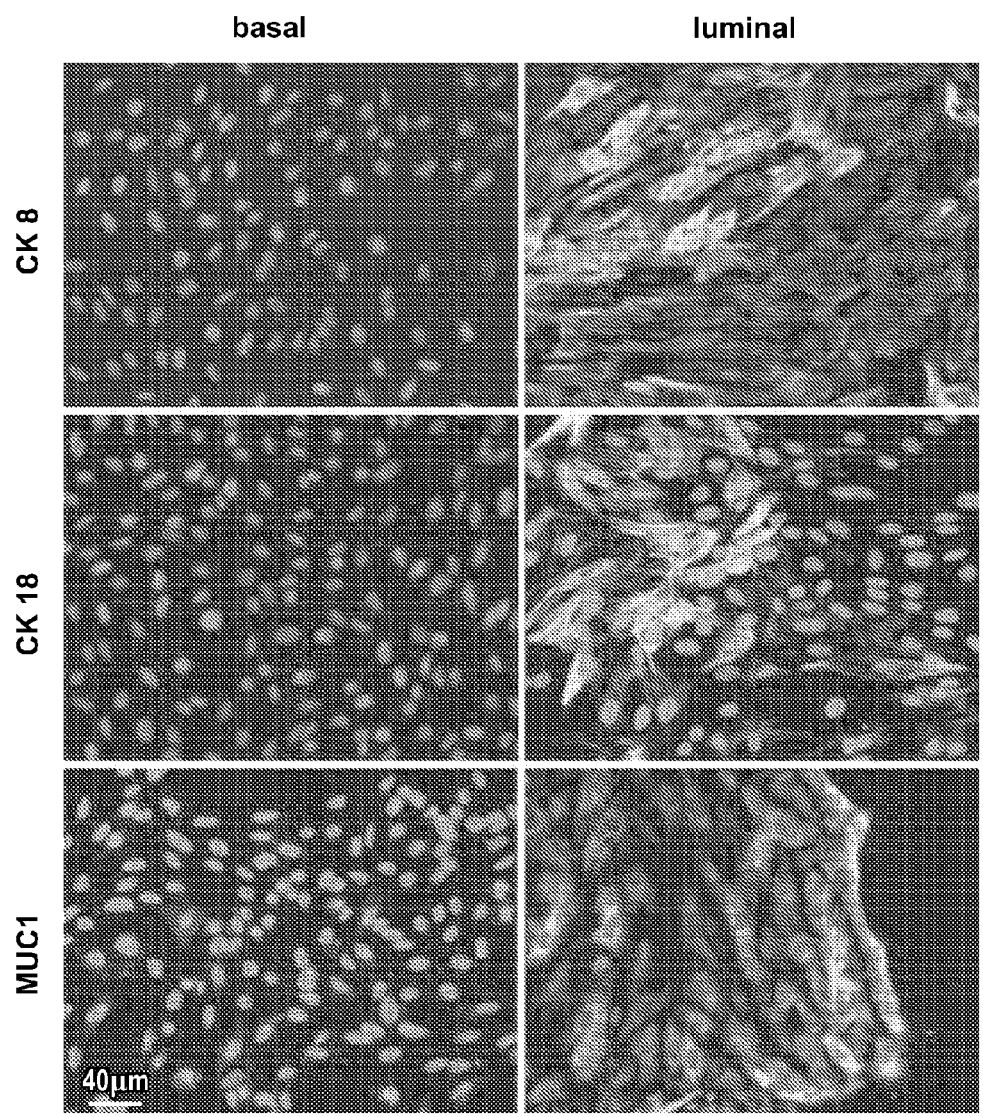
Figure 6D:
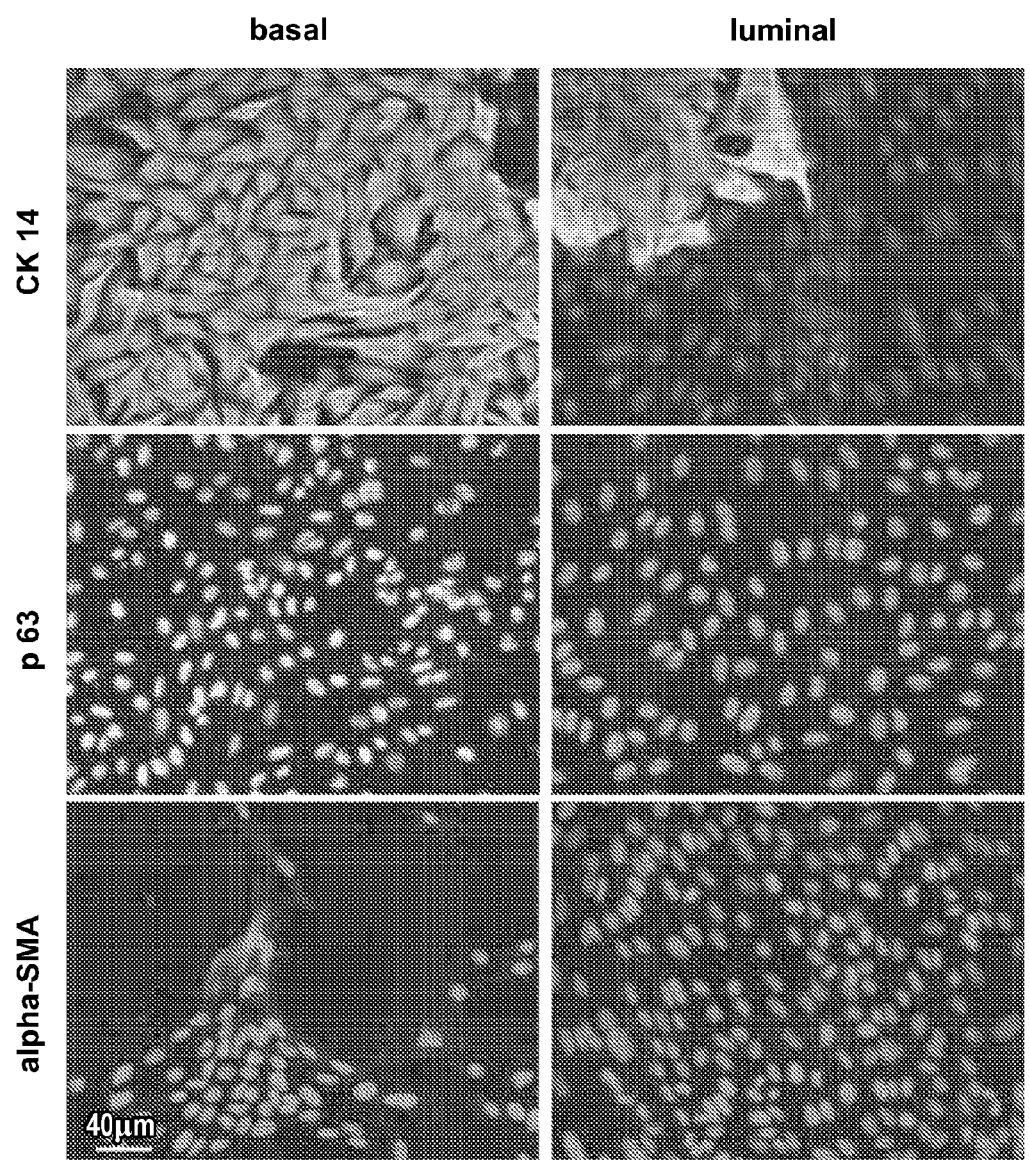
Figure 6E:
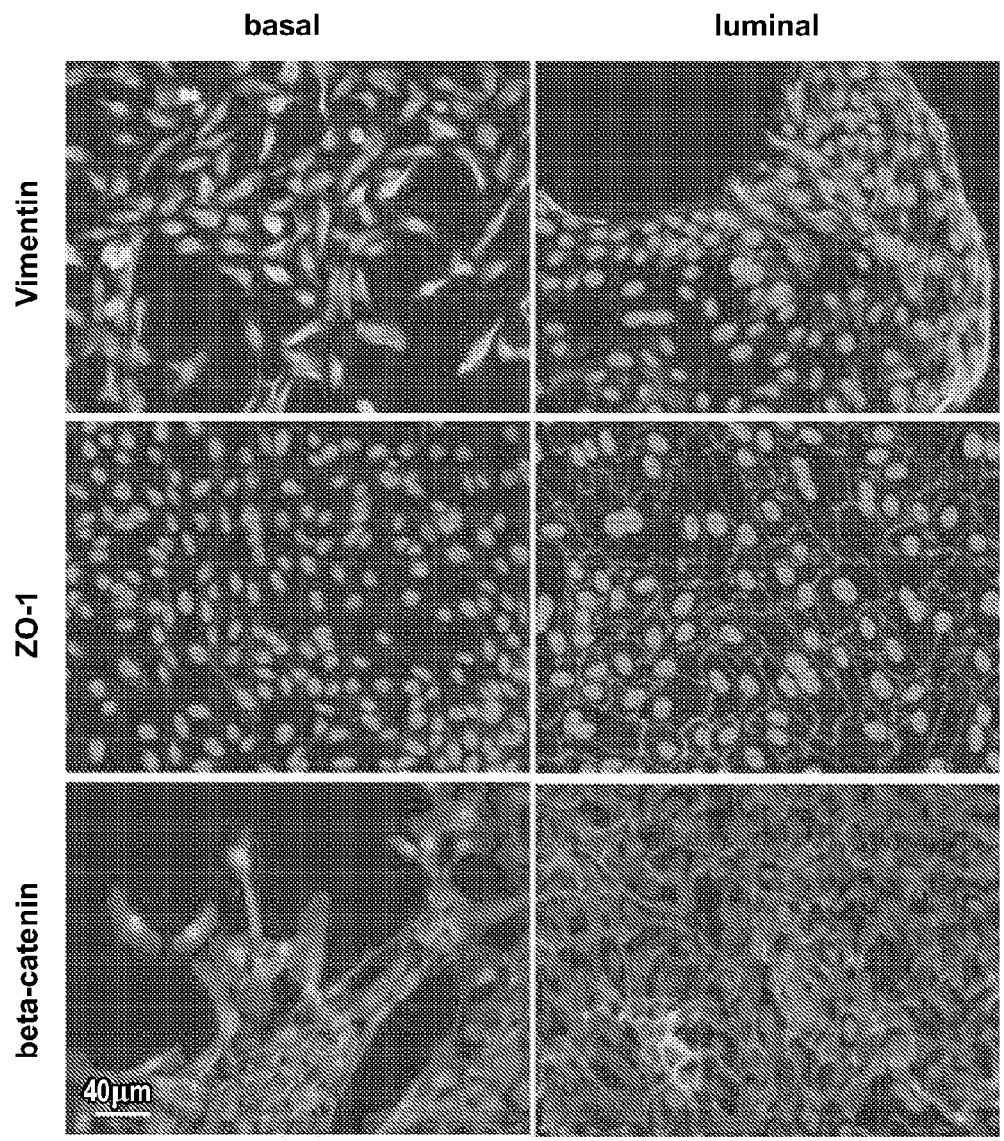
Figure 13A:
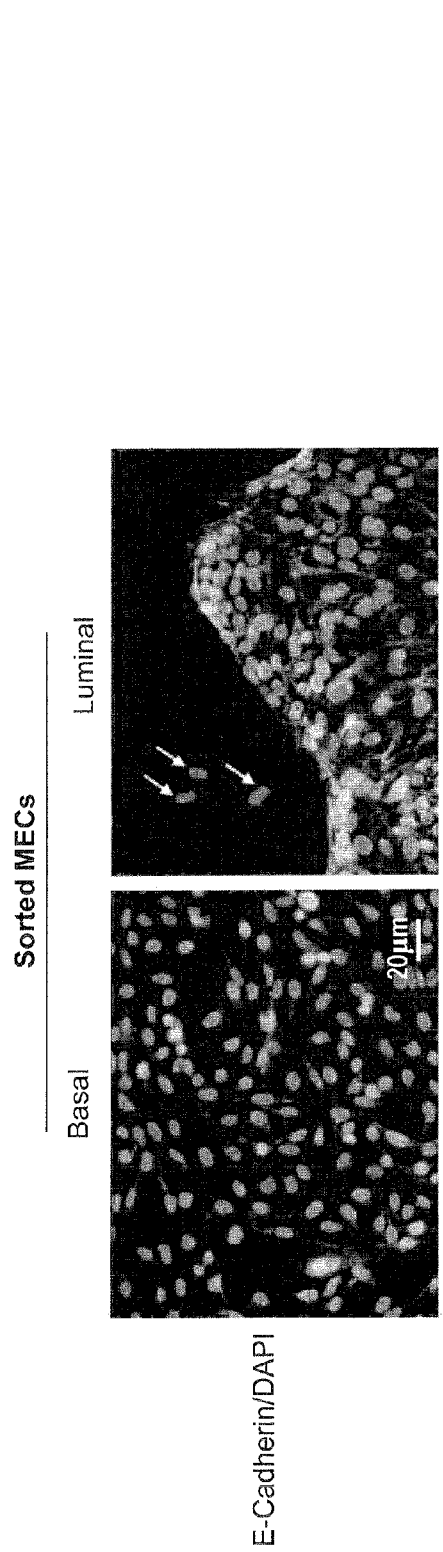
FIGS. 13A-13B. Immunofluorescence of primary MECs.
Figure 13B:
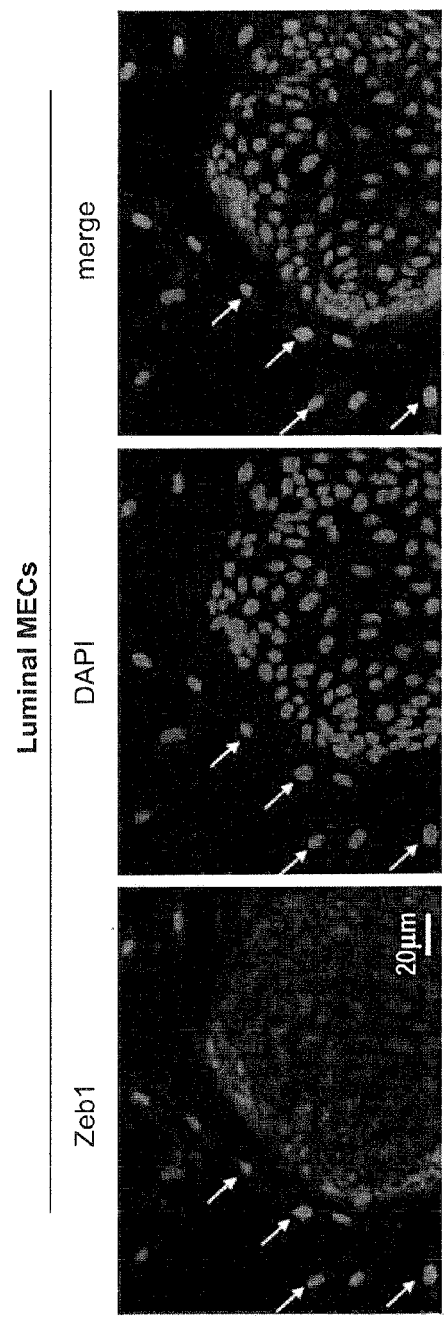

We noted that basal cell populations consisted mostly of single, front-to-end polarized cells, whereas luminal cells formed tightly clustered epithelial islands (FIG. 6B). We also measured the expression of epithelial and mesenchymal markers: indeed, basal cells expressed high levels of the mesenchymal marker vimentin, but they formed neither ZO-1-containing tight junctions (FIG. 6E) nor adherens junctions, as gauged by their low levels of E-Cadherin, little of which was localized to the plasma membrane (FIG. 13A). In striking contrast, the luminal cells expressed high levels of ZO-1 and E-Cadherin localized to the cell membrane, both of which are associated with differentiated epithelial cells (FIG. 6E, and 13A).

Figure 6F:
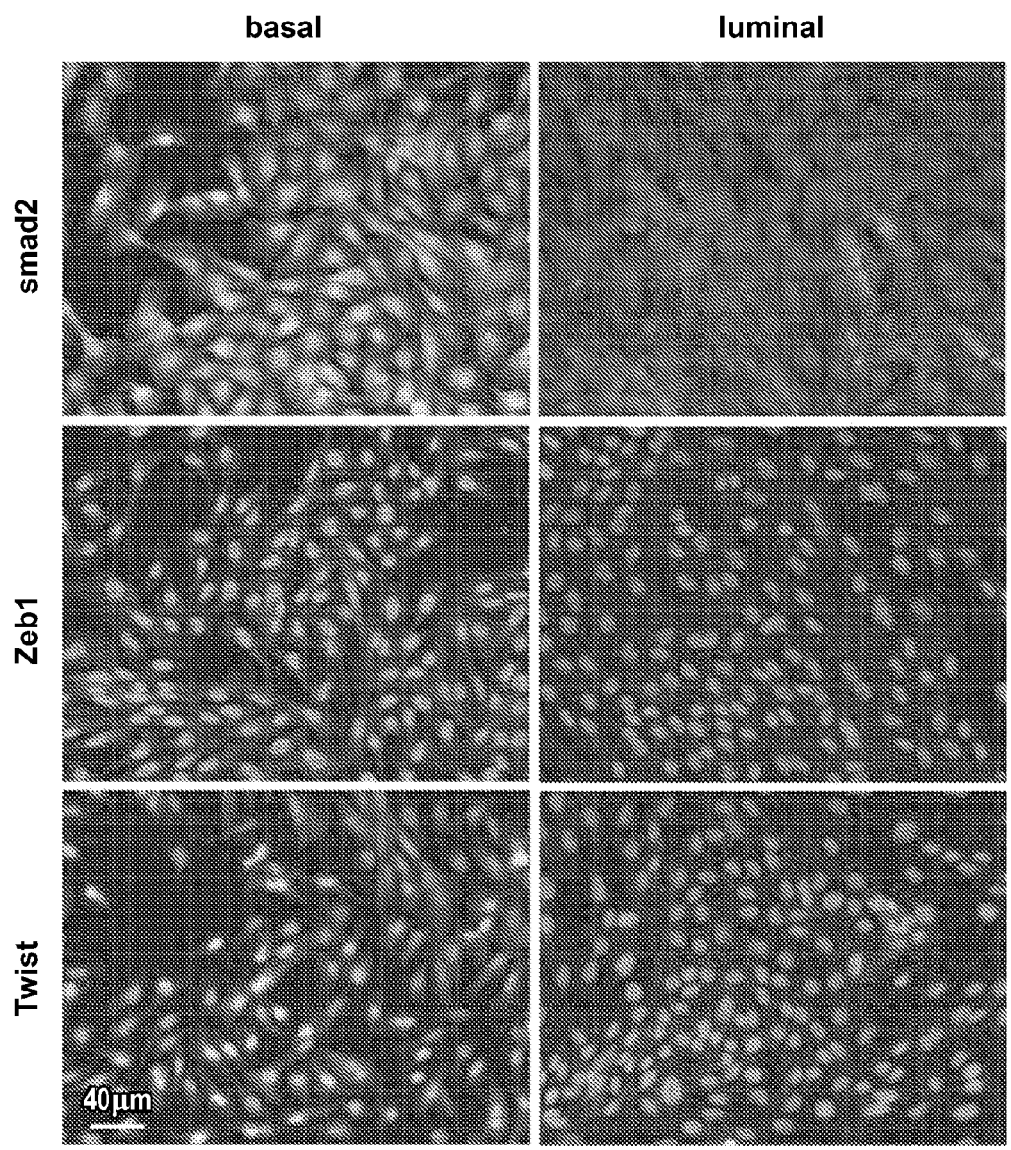
Figure 6G:
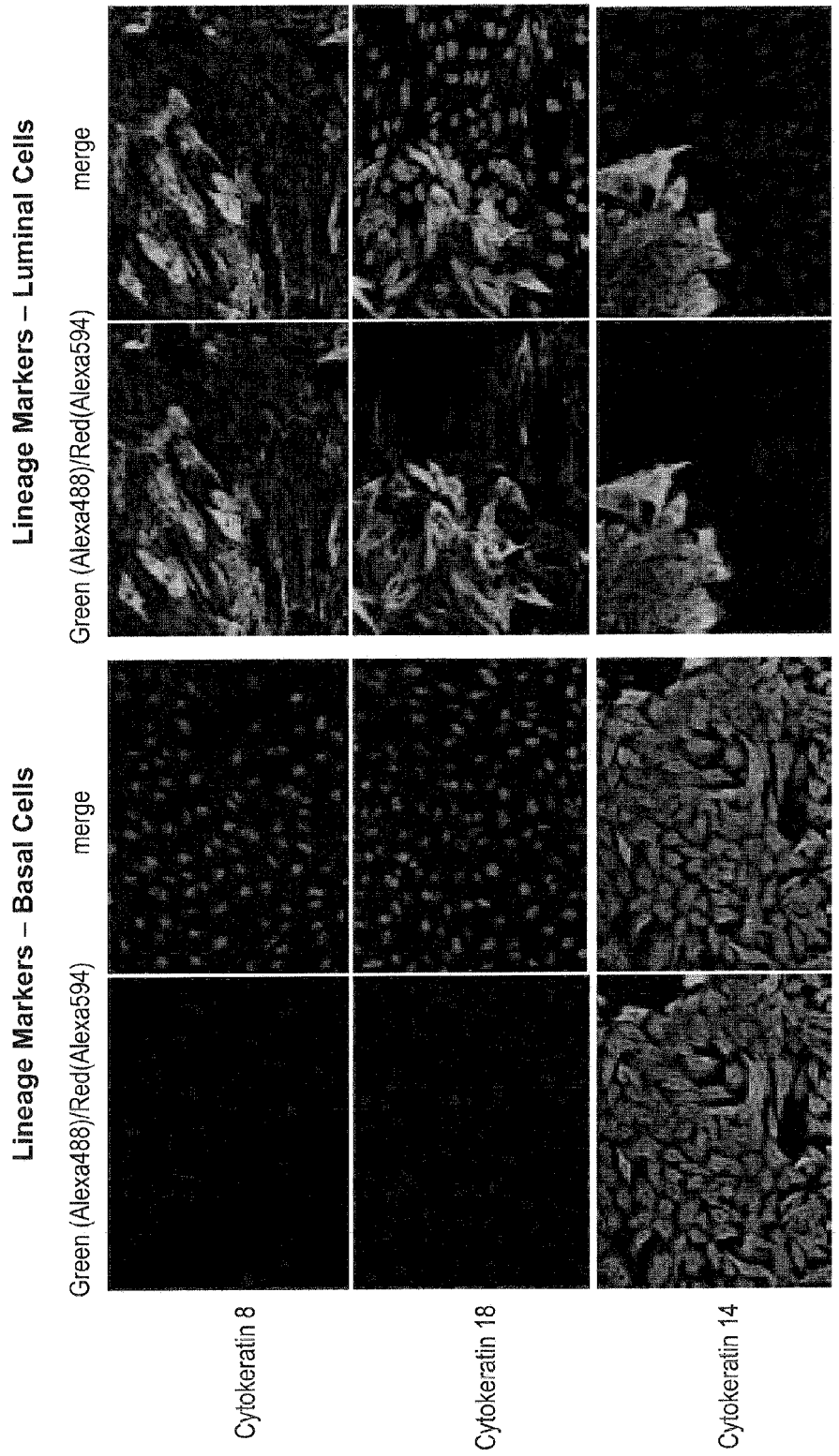
(FIG. 6G) and (FIG. 6H) show images of single-fluorescent signals.
Figure 6G:
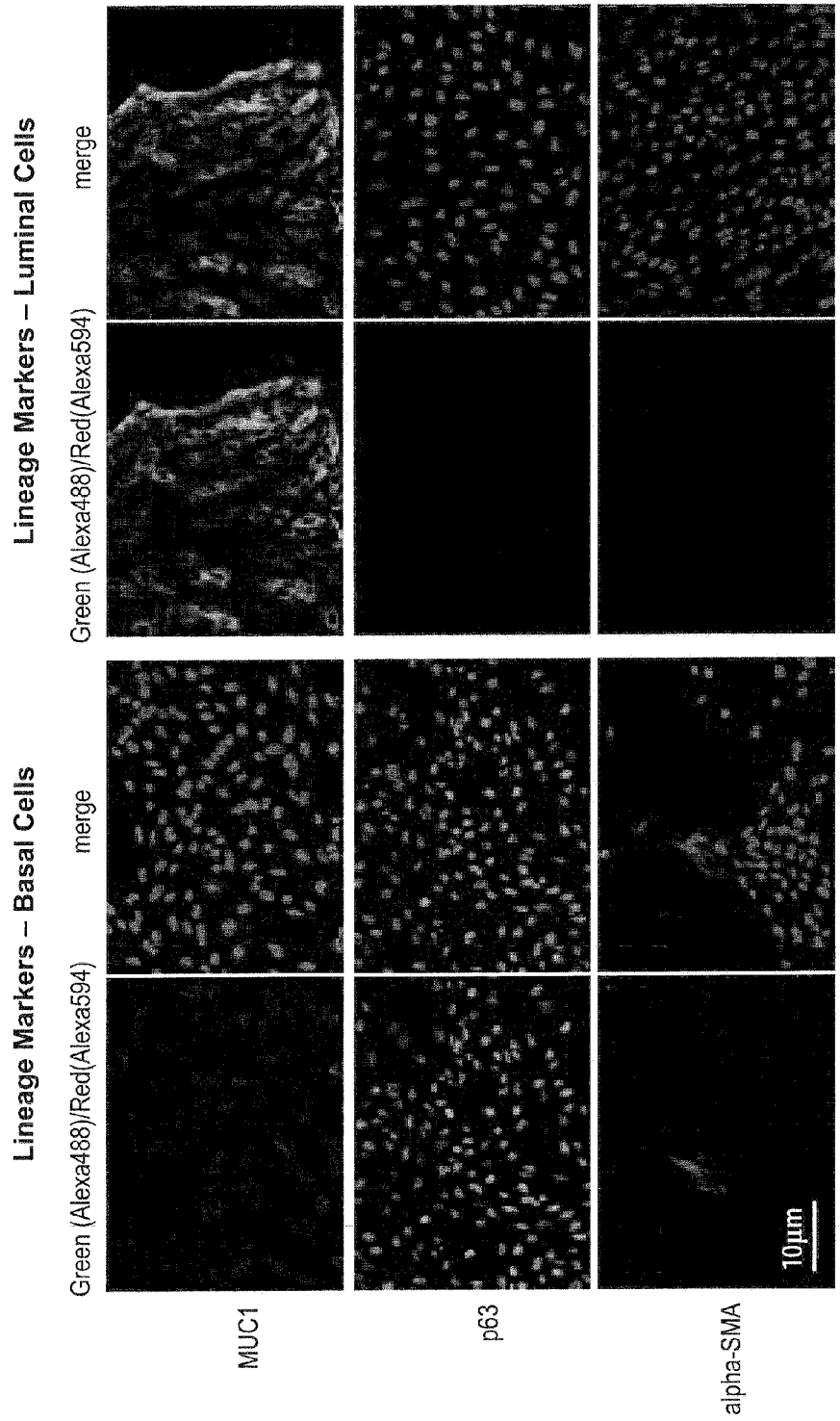
Figure 6H:
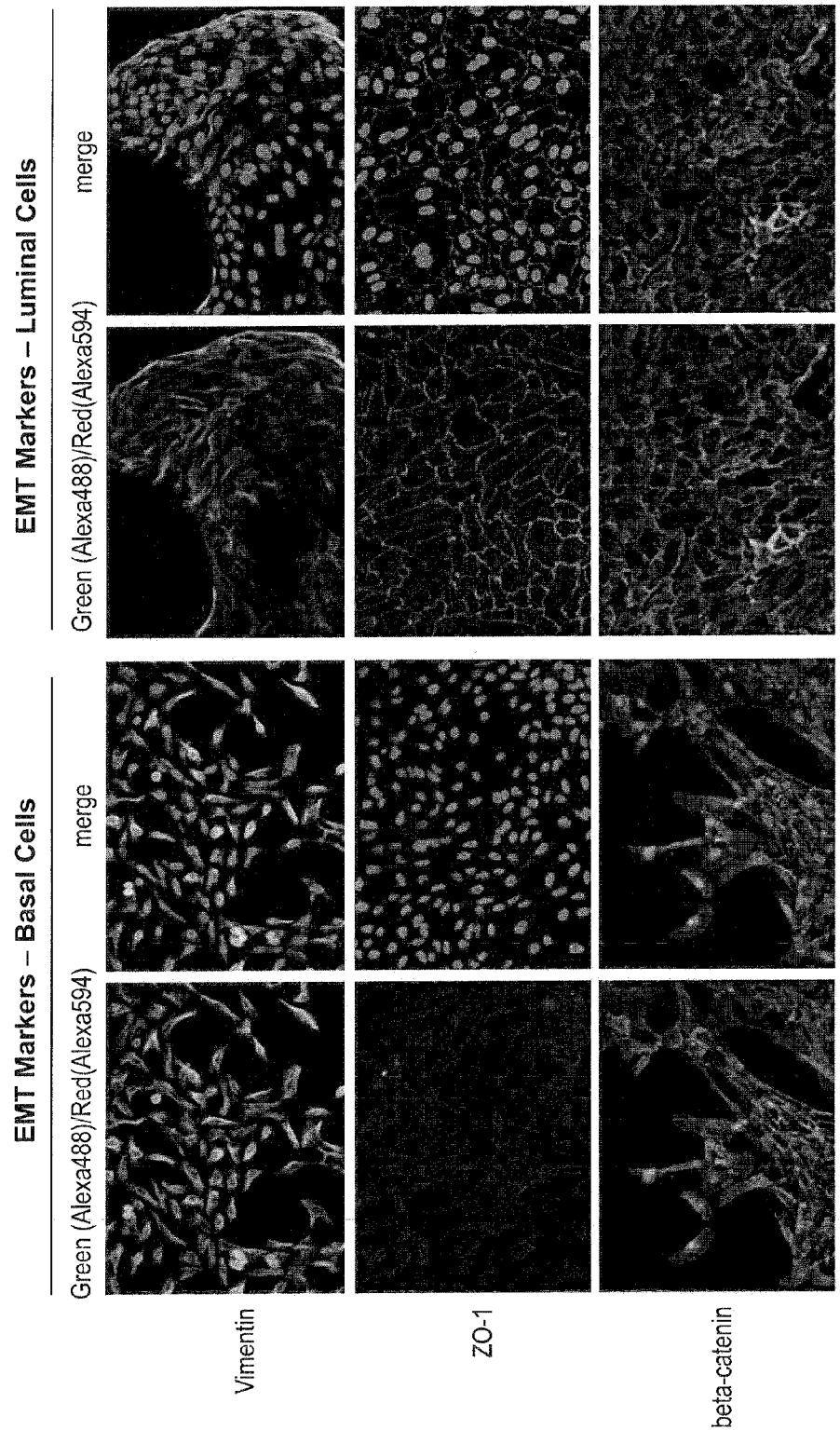
Figure 6H:
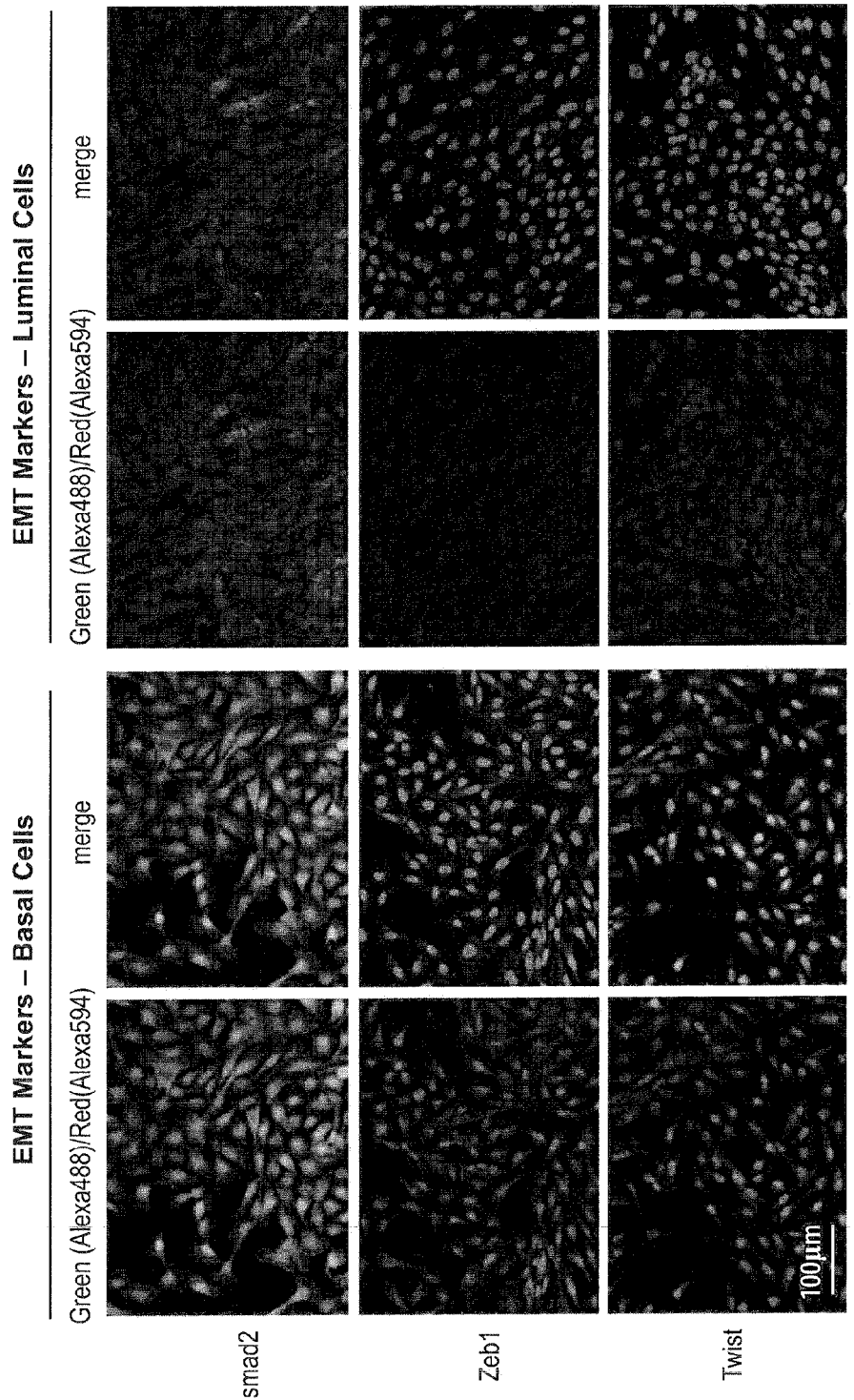

We proceeded to determine whether the mesenchymal properties of basal cells correlated with activation of signaling pathways that we had implicated in the induction and maintenance of EMT-associated traits, specifically Wnt and TGF-beta pathways. Indeed, basal cells displayed cytoplasmic and nuclear beta-catenin expression, indicative of active Wnt signaling. By contrast, beta-catenin expression was almost entirely confined to the plasma membrane in luminal cells (FIG. 6E). In addition, we found that basal cells expressed high levels of nuclear Smad2, indicative of TGF-beta signaling, and EMT-TFs ZEB1 and Twist (FIG. 6F). Expression levels of these three proteins were lower and cytoplasmic in luminal cells (FIG. 6F). These data indicated that basal cells reside in a more mesenchymal state and express EMT-TFs similar to the previously studied HTwist, MSP and HMLE$^{24+}$-iEMT cells. Since basal populations have been reported to contain stem cells and bipotent progenitor cells giving rise to both the myoepithelial and luminal lineages (Eirew et al., 2008; Stingl et al., 2001), our data indicated that mammary epithelial stem and progenitor populations might undergo a mesenchymal-epithelial transition (MET)-like process upon differentiation to luminal-restricted cells.

Example 10

Figure 7A:
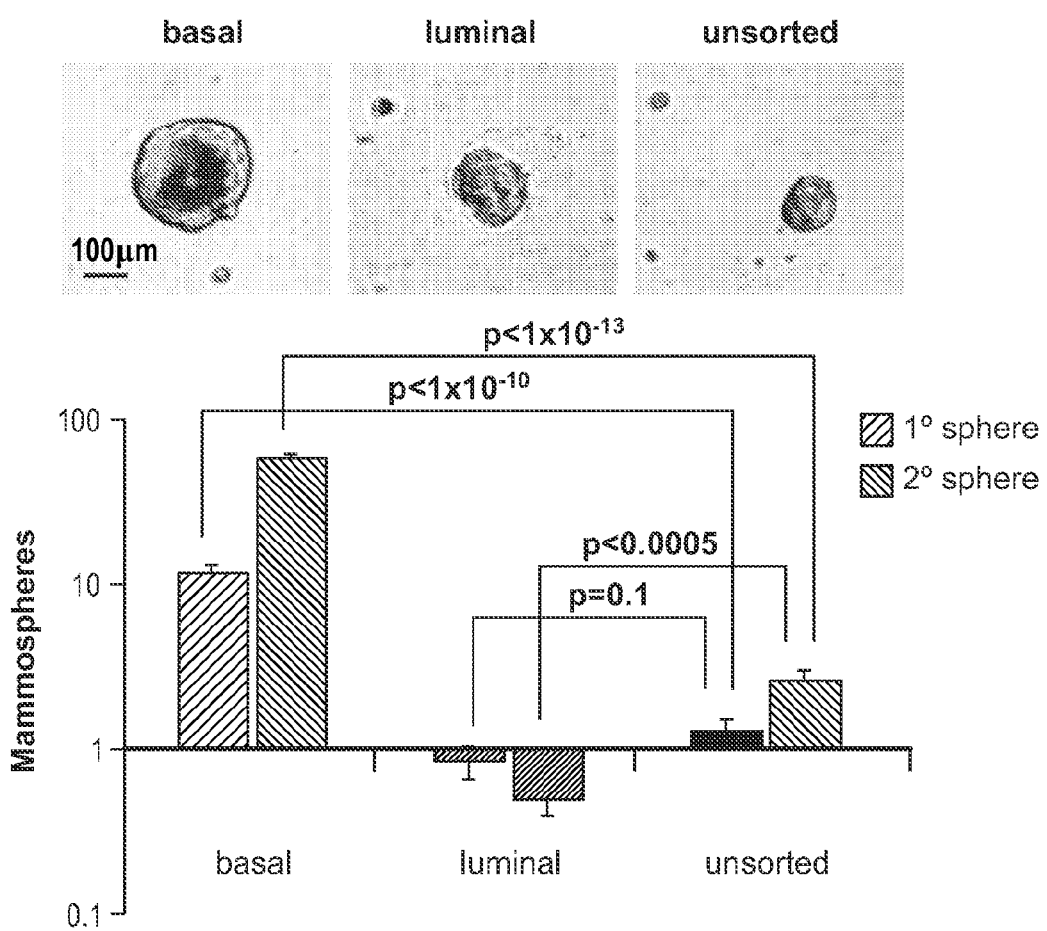

Migratory and Self-renewal Properties in Primary MECs are Controlled by Similar Signaling Mechanisms as in HTwist and MSP Cells We next wished to test whether the basal cells that we had we isolated displayed functional properties of the mesenchymal and SC-like state, similar to those of HTwist and MSP cells. To begin, we employed the mammosphere assay to test for the presence of progenitor or SCs. In our hands, unsorted, bulk MEC populations displayed a mammosphere-forming frequency of 0.15%, whereas 1-2% of the basal cells formed mammospheres, corresponding to a 10-fold enrichment (FIG. 7A). In contrast, only 0.09% of the luminal cells gave rise to mammospheres that were generally smaller in size (FIG. 7A). Remarkably, when primary spheres were dissociated and reintroduced into the mammosphere assay for secondary sphere formation, we observed a 5-fold increase in mammosphere-forming efficiency in basal cells, indicating an expansion of sphere-forming cells (FIG. 7A). In unsorted cells, we observed a 2-fold increase in mammosphere-forming efficiency. However, there was no expansion of the small mammospheres formed by luminal cells. These data suggest that basal cells self-renew in the mammosphere assay, reinforcing the notion that they are enriched for progenitor and SCs.

Figure 7B:
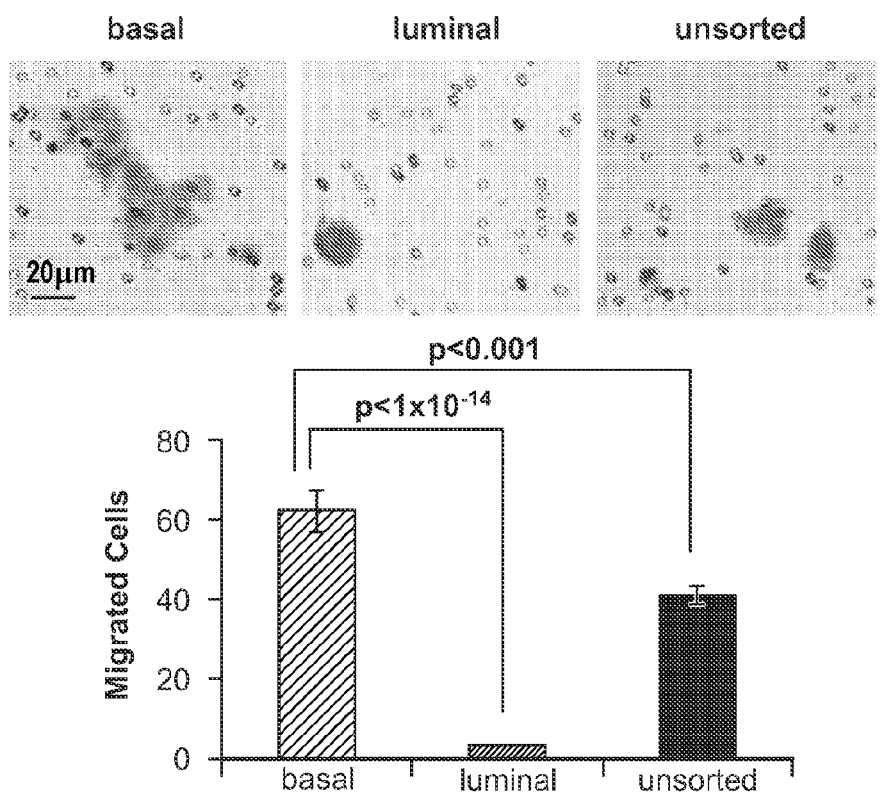

In the HMLE model system, we had observed that passage through an EMT conferred both migratory as well self-renewal properties, prompting us to measure the motility of sorted primary MECs. Indeed, basal cells were highly motile, displaying a 20-fold greater ability to migrate in vitro relative to unsorted bulk MECs. In contrast, very few of the luminal cells migrated, corresponding to a 2-fold lower motility relative to bulk MECs (FIG. 7B). Together, these data demonstrate that, like HTwist and MSP cells, primary basal cells are enriched both for self-renewal as well as migratory abilities.

Figure 14A:
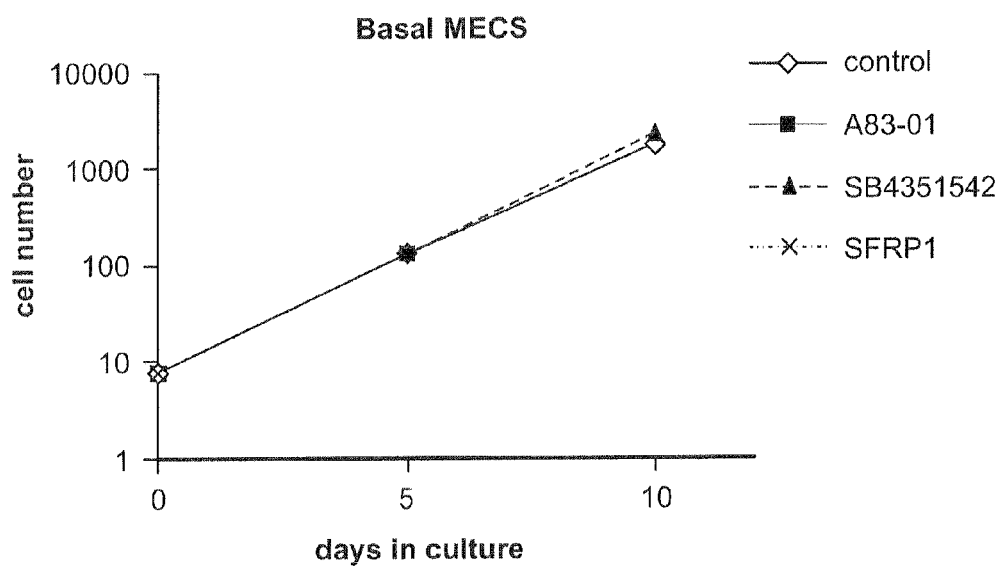
FIGS. 14A-14D. Modulation of migratory and self-renewal abilities in basal and luminal MECs.
Figure 14B:
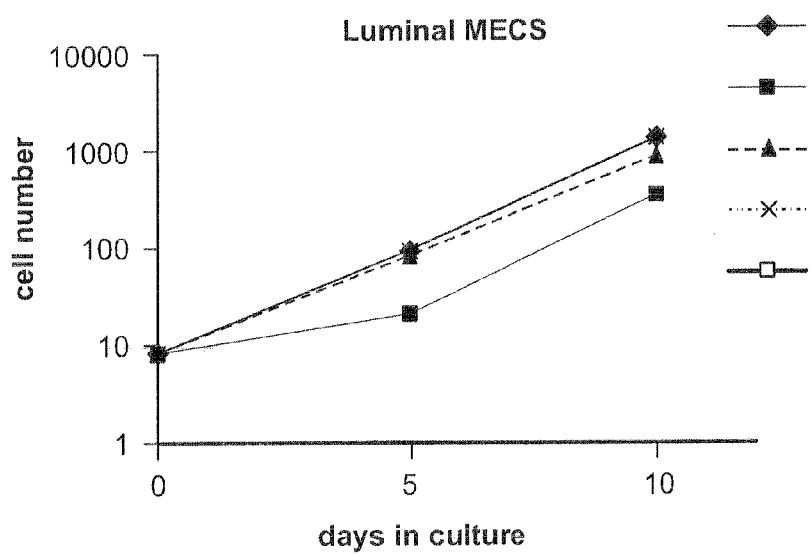
Figure 14C:
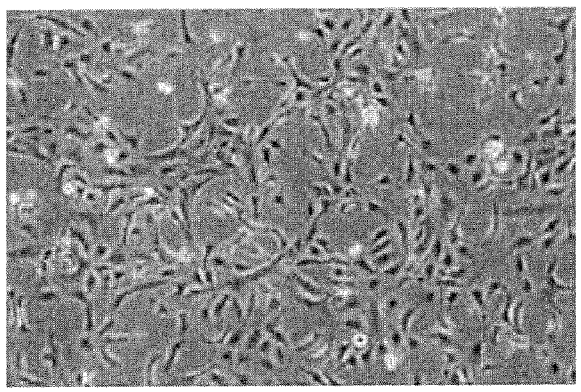
Figure 14C:
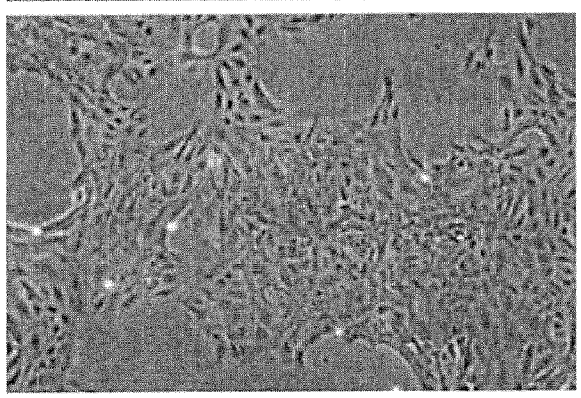
Figure 14C:
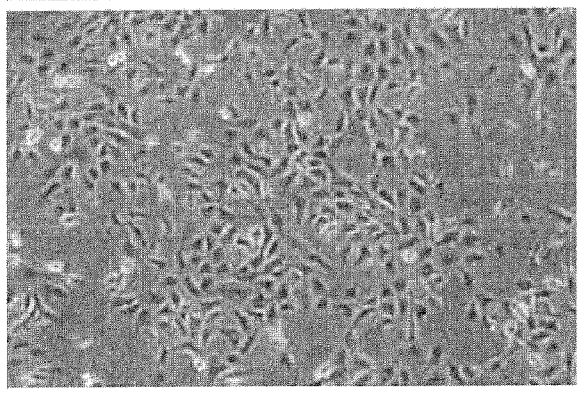
Figure 14C:
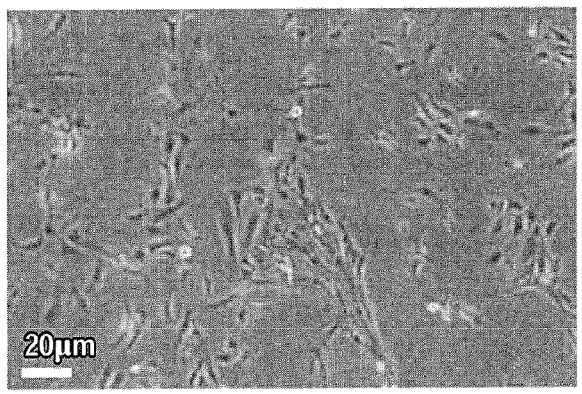

We also undertook to test whether the autocrine loops operating in HTwist and MSP cells enabled basal MECs to maintain their self-renewal and migratory abilities. Because recombinant BMP4 exerted a strong anti-proliferative effect on primary MECs (data not shown), we instead inhibited TGF-beta signaling directly by use of pharmacologic inhibitors specific for the TGF-beta Type I receptor (A83-01 and SB431542). In addition, we blocked autocrine Wnt signaling through application of recombinant SFRP1. After a 5-day, daily treatment with both TGF-beta inhibitors or SFRP1 in monolayer cultures, basal cells were submitted to migration and mammosphere assays in the absence of further treatment. Importantly, these treatments did not reduce proliferation of basal cells in monolayer cultures, excluding any general cytotoxic effects (FIG. 14A). Of note, basal cells treated with TGF-beta inhibitors displayed a more epithelial morphology (FIG. 14B).

Figure 7C:
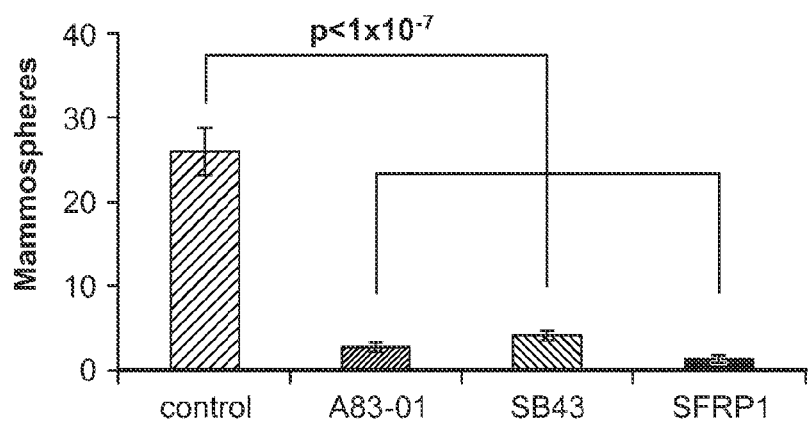
Figure 7D:
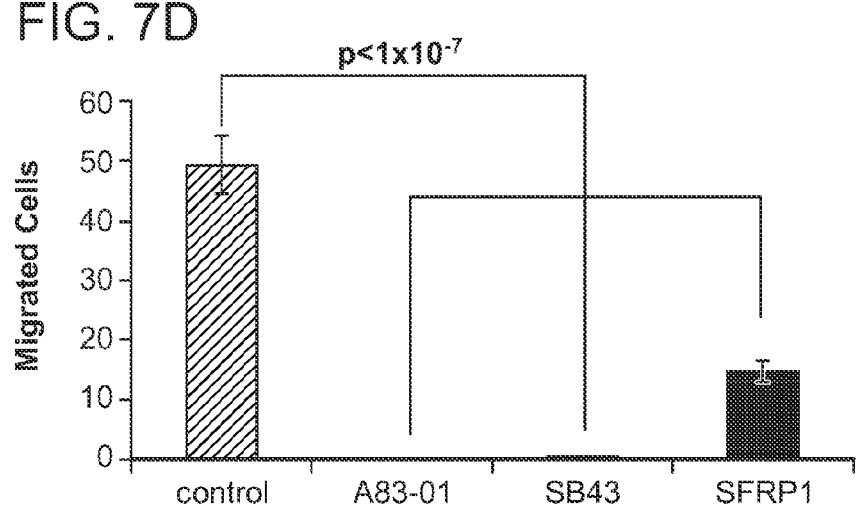

Remarkably, pre-treatment with the TGF-beta inhibitors or SFRP-1 reduced mammosphere formation by 80-90% (FIG. 7C). Furthermore, we observed a complete inhibition of motility by pre-treatment with the TGF-beta inhibitors, and a 3-fold reduction by pre-treatment with SFRP1 (FIG. 7D). Since no Wnt and TGF-beta ligands were added exogenously, these data suggest that basal cells, similar to HTwist and MSP cells, employ autocrine TGF-beta and Wnt signaling pathways to maintain both their self-renewal and migratory abilities.

Figure 7E:
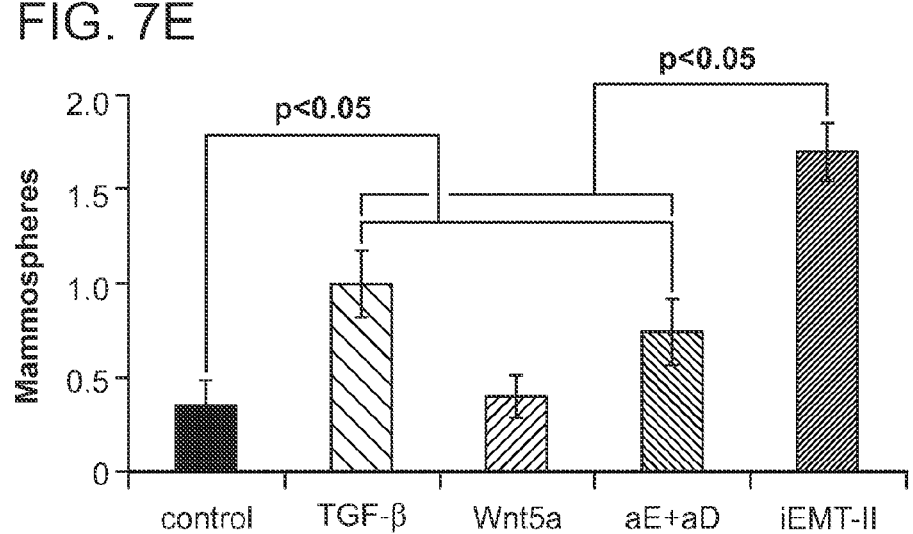
Figure 7F:
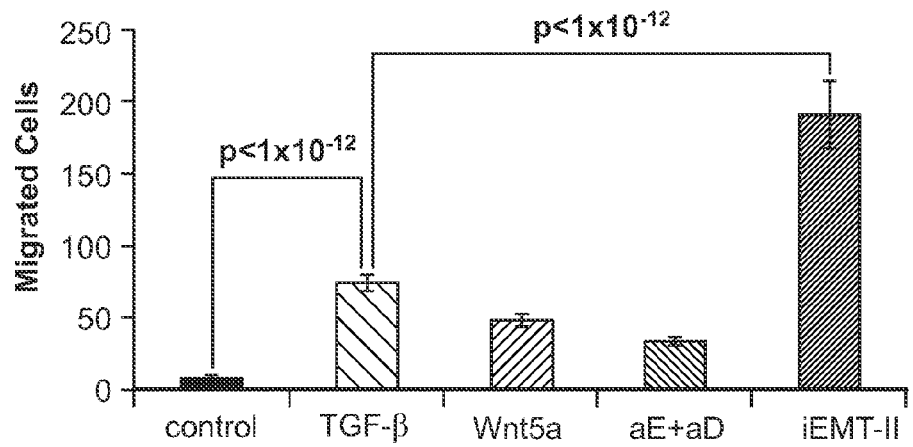
Figure 14D:
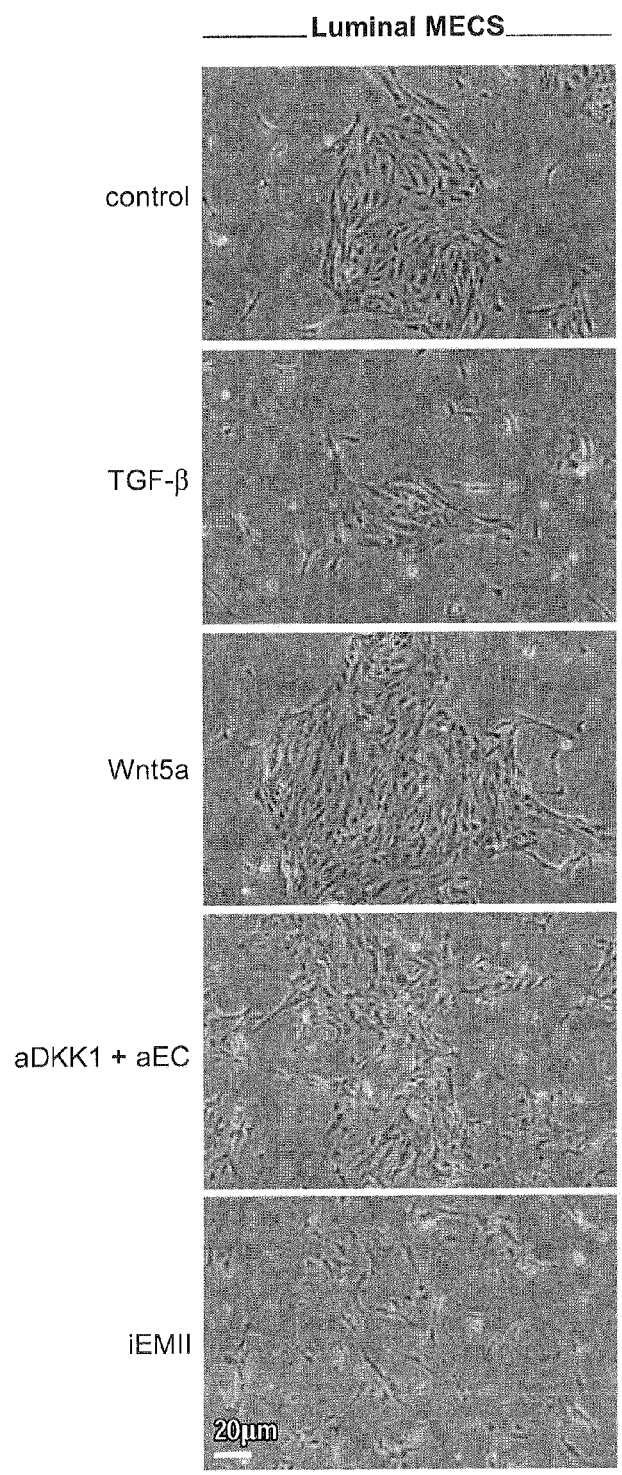

Analogous to our experiments using HMLE$^{24+}$ cells, we wished to determine whether migratory and self-renewal abilities could be induced in luminal cells via a similar EMT-induction cocktail, consisting of TGF-beta together with Wnt5a, anti-E-Cadherin and anti-DKK1 antibodies (iEMT-II, FIG. 7E). We observed pronounced cells scattering and dispersal of epithelial islands during iEMT treatment, but not in the other cultures (FIG. 14D). However, in contrast to HMLE$^{24+}$ cells, in these primary cultures of luminal cells, we observed a significant increase in both motile and mammosphere-forming cells following a 5-day treatment with TGF-beta as a single agent (8-fold and 3-fold, respectively, FIGS. 7E and 7F), suggesting that primary luminal cells are more responsive to TGF-beta than HMLE$^{24+}$ cells. However, adding the iEMT cocktail resulted in an additive effect, enhancing motility more than 20-fold and mammosphere-forming efficiency 5-fold (FIGS. 7E and 7F). Of note, the baseline levels of these properties in control lumina) cells assays were minimal with, on average, 0.0003% of cells migrating, and 0.03% giving rise to mammospheres. We also observed that, in contrast to the mammosphere assay, proliferation in monolayers was significantly reduced in TGF-beta- and iEMT-treated luminal cultures, suggesting that these cells respond to the growth-inhibitory effects of TGF-beta (de Winter et al., 1997).

Together, these results indicated that basal MECs isolated from human mammary gland tissue are enriched for migratory and self-renewal properties similar to immortalized HTwist, MSP and iEMT populations. The maintenance of these properties in freshly isolated basal cells appears to depend on similar, if not identical autocrine loops as those operating in both immortalized and transformed HMLE cells residing in the mesenchymal/SC-like state. Importantly, these autocrine factors can be applied to luminal cells to induce migratory and self-renewal properties, similar to induction of an EMT in HMLE cells as demonstrated in prior experiments. Taken together, these data indicate that passage through an EMT in HMLE cell lines reflects the adoption of properties that are naturally present in basal MECs.

Materials and Experimental Procedures for Examples 1-10

Cell lines. Human mammary epithelial cell lines (HMLE) were generated as described and propagated in MEGM medium (Lonza) according to standard protocol (Elenbaas et al., 2001). Detailed descriptions of cell lines are provided below.

Primary mammary epithelial cell culture. Single-cell suspensions of primary human mammary epithelial cells (MECs) were generated from reduction mammoplasties of pre-menopausal women as previously described (Stingl et al., 2001), Data from three donors are included in this study. Primary MECs were cultured on collagen I-coated plates (Millipore) in MEGM medium (Lonza) supplemented with 1% Fetal Bovine Serum in a humidified 4% $O_2$, 5% $CO_2$, atmosphere.

Migration and invasion assays. For migration assays, $2 \times 10^4$ cells were seeded into 24-well cell culture inserts with 8-μm pores (Boyden Chambers, BD Falcon). For invasion assays, matrigel-coated inserts (BD Falcon) were used. After 12-48 hr, the cells on the upper surface of the filters were removed with a cotton swab. For visualization, cells on lower filter surfaces were fixed and stained with a Diff-Quick staining kit (Dade Behring).

Mammosphere and tumorsphere assay. Assays were performed as previously described with modifications (Dontu et al., 2003): 1000 cells/well were seeded in 96-well ultra-low adhesion plates (Corning) in MEGM medium containing 1.3% methylcellulose (Stem Cell Technologies) supplemented with 20 ng/ml EGF, 10 ng/ml bFGF (both Sigma) and B27 (Gibco). Primary spheres were dissociated by trypsinization and replated for secondary sphere formation after a period of 5-7 days.

Animal studies. All research involving animals complied with protocols approved by the MIT Committee on Animal Care. For tumorigenicity studies, indicated numbers of cells in 100 μL of Matrigel (BD Biosciences) diluted 1:4 in PBS were injected subcutaneously in the left and right flanks of age-matched female nude (nu/nu) mice. Mice were sacrificed and necropsied after 10 weeks. For orthotopic injections, $1 \times 10^5$ cells suspended in PBS were injected into each of the two inguinal mammary glands of age-matched female NOD-SCID mouse. Mice were sacrificed after 10 weeks or when tumors reached a diameter >1 cm. Lung surface metastases were counted using a fluorescent microscope within 3 hr of specimen isolation.

Immunoblots. Protein was extracted with RIPA lysis buffer and concentration determined by the Lowry assay (Biorad). Protein lysates were resolved on a 4%-12% Bis-Tris Gel, transferred to PVDF membranes, probed with HRP-linked secondary antibodies (GE Healthcare) and visualized with ECL reagent (Thermo Scientific).

Immunofluorescence. Cells were grown on Labtek II-CC2 Chamber slides (Nunc), fixed with 4% paraformaldehyde and permeabilized with 0.2% Triton-X-100/PBS prior blocking with 10% goat serum (Caltag). Secondary antibodies were goat-anti-mouse or -rabbit coupled to Alexa-488 or -594 (Invitrogen). Cell nuclei were visualized with DAPI (Sigma). Slides were mounted with SlowFade Gold antifade reagent (Invitrogen).

Fluorescent activated cell sorting (FACS) and flow cytometry. Cells were prepared according to standard protocols and suspended in 0.1% FBS/PBS on ice prior FACS. 7-AAD (BD Biosciences) was used to exclude dead cells. Samples were sorted on a BD FACSAria SORP and analyzed on a BD LSRII using BD FACSDiva Software (BD Biosciences).

Antibody arrays. Culture medium of HMLE$^{24+}$ and HTwist cells was collected following an incubation period of 48 h and filtered through a 20 μm mesh (BD Falcon). Each sample was biotinylated and hybridized in three dilutions to L-series 500-antibody arrays (Raybiotech). For each array, protein intensity values were background subtracted, scaled by the internal control, and floored at 1 unit. For each dilution, t-test p-values for triplicate arrays were used to rank proteins, and antibodies showing changes in different directions were excluded. The top 10% assayed proteins were selected by mean rank across three dilutions.

ELISA. Culture medium was collected following an incubation period of 48 h and filtered through a 20 μm mesh (BD Falcon), All ELISAs were performed using commercially available kits according the manufacturer's instructions. For DKK1, Pentraxin 3, TGF-beta 1, VEGF-c and uPA, kits and ancillary products were purchased from R&D systems. All ELISA readouts were normalized by cell number.

Microarray hybridization, data collection, and analysis. Total RNA was extracted from three independent culture plates for HMLE, HTwist and HSnail cells, and from two independent plates of HMLE$^{24\ +}$ and three independently generated MSP cell lines with the RNeasy Mini kit (Qiagen). Synthesis of cRNA and hybridization/scanning of microarrays were done with Affymetrix GeneChip products as described in the GeneChip manual. Raw data (CEL) files were normalized and summarized into probeset values with RMA using Bioconductor (Irizarry et al., 2003). Microarray data were subjected to Gene Set Enrichment Analysis (GSEA) as described in (Subramanian et al., 2005). For this purpose, 990 curated gene sets from the Molecular Signature Database (MSigDB, broadinstitute.org/gsea/msigdb/) were queried.

Cell Lines. Human mammary epithelial cell lines (HMLE) were generated as described and immortalized using retroviral vectors to express the catalytic subunit of the human telomerase enzyme, hTERT and the SV-40 Large T antigen (Elenbaas et al., 2001). HMLE cells were propagated in MEGM medium (Lonza) according to standard protocols. CD24-positive HMLE (HMLE$^{24+}$) cells were purified by MACS, using the Cellection Kit for mouse IgG (Invitrogen) for positive selection with a CD24 antibody (BD Biosciences) according to the manufacturers instructions. Mesenchymal sub-population (MSP) cells were detected as a minority population of free-floating cells in confluent monolayer cultures of HMLE cells. When removed from HMLE cultures, these MSP populations re-adhered in new culture dishes and were subsequently propagated in monolayer cultures.

Plasmids, Virus production and infection of target cells. HMLE cells were cells were infected with pBABE-Twist or -Snail vector to generate HTwist and HSnail cells as previously described (Mani et al., 2008; Yang et al., 2004). To generate tumorigenic and green fluorescent protein (GFP)-expressing HMLE, HTwist and MSP cells, cells were infected with pBabe-V12H-RAS (Elenbaas et al., 2001) and pRRL-GFP vectors. For stable knockdown of SFRP1, pLKO1 small hairpin-expressing vectors were purchased from Open Biosystems (shSRP1_a, clone ID TRCN0000062168, shSFRP1_b, clone ID TRCN00000621672). Production and infection of target cells were previously described (Stewart et al., 2003). Infected cells were selected with 2 μg/mL puromycin, 200 μg/mL hygromycin, and 200 μg/mL neomycin.

Luciferase assays. Reporter Plasmids were previously described: Super 8× TOPFlash, corresponding FOPFlash control plasmid (Veeman et al., 2003) and SBE4-luc (Zawel et al., 1998). 5.0×10$^4$ cells were co-transfected with 500 ng of the indicated firefly luciferase reporter plasmid and 50 ng of pGL-SV 40-*Renilla* luciferase normalization control plasmid using Fugene 6 transfection reagent (Roche). Lysates were collected 24-48 hr after transfection, and firefly and *Renilla* luciferase activities were measured with a Dual-Luciferase Reporter System (Promega).

Recombinant proteins and inhibitors. Recombinant human DKK1, SFRP1 and mouse Wnt5a were purchased from R&D Systems. Recombinant BMP4 was obtained from Stemgent. Small molecule inhibitors were from Tocris (A83-01, Tojo et al., 2005) and Sigma (SB431542, Laping et al., 2002). Anti-DKK1 antibody was obtained from R&D Systems, anti-E-Cadherin antibody (HECD-1) from Invitrogen.

Antibodies

Immunoblotting: Beta-actin, Snail, Twist (Abcam); E-Cadherin, N-Cadherin (BD Transduction); ZEB1 (Bethyl Labs); phospho-SAPK/JNK (T183/Y185, clone G9), JNK, phospho-c-JUN (S63), JUN, phospho-PKC (pan, beta II/Ser660), Slug (C19G7), phospho-smad2, smad2/3 (Cell Signaling); Wnt5a (R&D Systems).

Immunofluorescence: E-Cadherin, smad2/3, Twist, ZEB1, see Immunoblotting; alpha-smooth muscle actin-Cy3 (Sigma), beta-catenin, total (BD Transduction), cytokeratin 8 (TROMA-1, Developmental Studies Hybridoma Bank), cytokeratin 14 (AF64, Covance), cytokeratin 18 (DC10, Neo-Markers), MUC-1 (HMPV, BD Pharmingen), pan-cytokeratin (Biogenex), p63 (4A4, Santa Cruz), Vimentin (V9, Sigma), ZO-1 (Invitrogen).

FACS: EpCAM-FITC (StemCell Technologies), CD24-FITC (BD Pharmingen), CD31-APC (WM59, BD Pharmingen), CD44-APC (BD-Pharmingen) CD45-V450 (BD Horizon), CD49f-PE (BD Pharmingen).

RNA preparation and RT-PCR analysis. Total RNA was isolated using the RNeasy Micro kit (Qiagen). Reverse transcription was performed with the Superscript III First Strand Synthesis kit (Invitrogen). SYBR Green Mix I (Roche Diagnostics) was used for amplification and samples were run on a Lightcycler-II Instrument (Roche Diagnostics). Analysis was described previously (Yang et al., 2004). A list of primers is provided below.

Primers Used for RT-PCR

| Target | Sequences: Forward, Reverse (5'->3' orientation) |
|---|---|
| Wnt1 | TTCTCCGGGTCCTCCTAAGT, ATGGCTCCACGACAGAGACT |
| Wnt2 | GTGGATGCAAAGGAAAGGAA, AGCCAGCATGTCCTGAGAGT |
| Wnt3a | CAAGATTGGCATCCAGGAGT, ATGAGCGTGTCACTGCAAAG |
| Wnt4 | ATGGAAGTCACACCCTCTGG, CCTGGAAGGACCCACAGATA |
| Wnt5A | GGGTGGGAACCAAGAAAAAT, TGGAACCTACCCATCCCATA |
| Wnt5B | GCGAGAAGACTGGAATCAGG, AACATCTCGGGTCTCTGCAC |
| Wnt6 | GTCACGCAGGCCTGTTCTAT, CGTCCATAAAGAGCCTCGAC |
| Wnt 8A | GAACTGCCCTGAAAATGCTC, ATCCTTTCCCCAAATTCCAC |
| Wnt 8B | TGGGCTTTGAGAATTCCATC, CTGCCACACTGCTGGAGTAA |
| Wnt 9A | GCAAGCATCTGAAGCACAAG, TGCTCTCGCAGTTCTTCTCA |
| Wnt 10A | GGTTGCTCCACACCCTAAAA, ATGATGAAGGGAATGGTGGA |
| Wnt 10B | TCTGACAAGGGGACAGAACC, TCATTGCTTAGAGCCCGACT |
| Wnt 11 | CAGGCAGTGCAACAAGACAT, TGAGGGTCCTTGAGCAGAGT |
| Wnt16 | AAATGCGCAGGAGAGAAAAA, ACCCTCTGATGTACGGTTGC |
| Gremlin | GCTCTGGCATTCAGAGAACC, AAATTCGCCTAGCGTGAGAA |
| BMP2 | GTCCGCAGTCTTACGAGGAG, TGGAGGACCTGGTAGAGGAA |
| BMP4 | CAGAGCCTTTCCAGCAACTC, TCGCTCGACTTCTTGCTGTA |
| BMP5 | CCCCACTTTTTGACGAAGAA, CAGTTTGATCCCAGCGTTTT |
| BMP6 | GGTTCTTCTGCGCTACTGCT, TAGGGCTGCTGGAAGGTAAA |

-continued

| Target | Sequences: Forward, Reverse (5'->3' orientation) |
|---|---|
| BMP7 | CCAGTTTGCATTTGGATGTG, GGTCAGAACGGCCAGTATGT |
| BMP9 | TTCATCCAGCAGTGTTGCTC, GGTGTGGGGTAGTGGAGAGA |
| BMP10 | TTTCTGTTGGCAAGTTGCTG, CGGGTCTCTTCTTCAAGTGC |
| DKK1 | TCCGAGGAGAAATTGAGGAA, CCTGAGGCACAGTCTGATGA |
| SFRP1 | CCAGTTTGCATTTGGATGTG, GGTCAGAACGGCCAGTATGT |
| SFRP2 | GCCTCGATGACCTAGACGAG, GATGCAAAGGTCGTTGTCCT |
| SFRP4 | GCCTGGGACAGCCTATGTAA, TCTGTACCAAAGGGCAAACC |
| SFRP5 | TGGAGCCCAGAAAAGAAGA, GCAGGGGTAGGAGAACATGA |
| hTwist | GTCCGCAGTCTTACGAGGAG, TGGAGGACCTGGTAGAGGAA |
| Snail1 | GGTTCTTCTGCGCTACTGCT, TAGGGCTGCTGGAAGGTAAA |
| FoxC2 | GCCTAAGGACCTGGTGAAGC, TTGACGAAGCACTCGTTGAG |
| ZEB1 | GCACAAGAAGAGCCACAAGTA, GCAAGACAAGTTCAAGGGTTC |
| ZEB2 | TTCCTGGGCTACGACCATAC, TGTGCTCCATCAAGCAATTC |
| E-Cadherin | TGCCCAGAAAATGAAAAAGG, GTGTATGTGGCAATGCGTTC |
| N-Cadherin | ACAGTGGCCACCTACAAAGG, CCGAGATGGGGTTGATAATG |
| L32 | CAGGGTTCGTAGAAGATTCAAGGG, CTGGAGGAAACATTGTGAGCGATC |

Proliferation Assays. To measure cell growth rates, 1000 cells were seeded onto 96-well plates in triplicate. Cell viability was measured using CellTiter-Glo (Promega) according to the manufacturer's instructions.

Statistical analysis. Data are presented as mean+/−SEM. Student's t test (two-tailed) was used to compare two groups ($p<0.05$ was considered significant) unless otherwise indicated.

REFERENCES

Abou-Khalil, R., Le Grand, F., Pallafacchina, G., Valable, S., Authier, F. J., Rudnicki, M. A., Gherardi, R. K., Germain, S., Chretien, F., Sotiropoulos, A., et al. (2009). Autocrine and paracrine angiopoietin 1/Tie-2 signaling promotes muscle satellite cell self-renewal. Cell stem cell 5, 298-309.

Acloque, H., Adams, M. S., Fishwick, K., Bronner-Fraser, M., and Nieto, M. A, (2009). Epithelial-mesenchymal transitions: the importance of changing cell state in development and disease. J Clin Invest 119, 1438-1449.

Al-Hajj, M., Wicha, M. S., Benito-Hernandez, A., Morrison, S. J., and Clarke, M. F. (2003). Prospective identification of tumorigenic breast cancer cells. Proc Natl Acad Sci USA 100, 3983-3988.

Bafico, A., Liu, G., Goldin, L., Harris, V., and Aaronson, S. A. (2004). An autocrine mechanism for constitutive Wnt pathway activation in human cancer cells. Cancer Cell 6, 497-506.

Brabletz, S., Schmalhofer, O., and Brabletz, T. (2009). Gastrointestinal stem cells in development and cancer. The Journal of pathology 217, 307-317.

Brabletz, T., Jung, A., Spaderna, S., Hlubek, F., and Kirchner, T, (2005). Opinion: migrating cancer stem cells—an integrated concept of malignant tumour progression. Nat Rev Cancer 5, 744-749.

Brown, K. A., Aakre, M. E., Gorska, A. E., Price, J. O., Eltom, S. E., Pietenpol, J. A., and Moses, H. L. (2004). Induction by transforming growth factor-beta1 of epithelial to mesenchymal transition is a rare event in vitro. Breast Cancer Res 6, R215-231.

de Winter, J. P., Roelen, B. A., ten Dijke, P., van der Burg, B., and van den Eijnden-van Raaij, A. J. (1997). DPC4 (SMAD4) mediates transforming growth factor-beta1 (TGF-beta1) induced growth inhibition and transcriptional response in breast tumour cells. Oncogene 14, 1891-1899.

Dissanayake, S. K., Wade, M., Johnson, C. E., O'Connell, M. P., Leotlela, P. D., French, A. D., Shah, K. V., Hewitt, K. J., Rosenthal, D. T., Indig, F. E., et al. (2007). The Wnt5A/protein kinase C pathway mediates motility in melanoma cells via the inhibition of metastasis suppressors and initiation of an epithelial to mesenchymal transition. J Biol Chem 282, 17259-17271.

Dontu, G., Abdallah, W. M., Foley, J. M., Jackson, K. W., Clarke, M. F., Kawamura, M. J., and Wicha, M. S. (2003). In vitro propagation and transcriptional profiling of human mammary stem/progenitor cells. Genes Dev 17, 1253-1270.

Eirew, P., Stingl, J., Raouf, A., Turashvili, G., Aparicio, S., Emerman, J. T., and Eaves, C. J. (2008). A method for quantifying normal human mammary epithelial stem cells with in vivo regenerative ability. Nature medicine 14, 1384-1389.

Elenbaas, B., Spirio, L., Koerner, F., Fleming, M. D., Zimonjic, D. B., Donaher, J. L., Popescu, N. C., Hahn, W. C., and Weinberg, R. A. (2001). Human breast cancer cells generated by oncogenic transformation of primary mammary epithelial cells. Genes Dev 15, 50-65.

Galli, L. M., Barnes, T., Cheng, T., Acosta, L., Anglade, A., Willert, K., Nusse, R., and Burrus, L. W. (2006). Differential inhibition of Wnt-3a by Sfrp-1, Sfrp-2, and Sfrp-3. Dev Dyn 235, 681-690.

Godar, S., Ince, T. A., Bell, G. W., Feldser, D., Donaher, J. L., Bergh, J., Liu, A., Miu, K., Watnick, R. S., Reinhardt, F., et al. (2008). Growth-inhibitory and tumor-suppressive functions of p53 depend on its repression of CD44 expression. Cell 134, 62-73.

Guo, X., and Wang, X. F. (2009). Signaling cross-talk between TGF-beta/BMP and other pathways. Cell research 19, 71-88.

Jauliac, S., Lopez-Rodriguez, C., Shaw, L. M., Brown, L. F., Rao, A., and Toker, A. (2002). The role of NFAT transcription factors in integrin-mediated carcinoma invasion. Nat Cell Biol 4, 540-544.

Laping, N. J., Grygielko, E., Mathur, A., Butter, S., Bomberger, J., Tweed, C., Martin, W., Fornwald, J., Lehr, R., Harling, J., et al. (2002). Inhibition of transforming growth factor (TGF)-beta1-induced extracellular matrix with a novel inhibitor of the TGF-beta type I receptor kinase activity: SB-431542. Molecular pharmacology 62, 58-64.

Lim, E., Vaillant, F., Wu, D., Forrest, N. C., Pal, B., Hart, A. H., Asselin-Labat, M. L., Gyorki, D. E., Ward, T., Partanen, A., et al. (2009). Aberrant luminal progenitors as the candidate target population for basal tumor development in BRCA1 mutation carriers. Nature medicine 15, 907-913.

Mani, S. A., Guo, W., Liao, M. J., Eaton, E. N., Ayyanan, A., Zhou, A. Y., Brooks, M., Reinhard, F., Zhang, C. C., Shipitsin, M., et al. (2008). The epithelial-mesenchymal transition generates cells with properties of stem cells. Cell 133, 704-715.

Morel, A. P., Lievre, M., Thomas, C., Hinkal, G., Ansieau, S., and Puisieux, A. (2008). Generation of breast cancer stem cells through epithelial-mesenchymal transition. PLoS ONE 3, e2888.

Oft, M., Heider, K. H., and Beug, H. (1998). TGF beta signaling is necessary for carcinoma cell invasiveness and metastasis. Curr Biol 8, 1243-1252.

Oft, M., Peli, J., Rudaz, C., Schwarz, H., Beug, H., and Reichmann, E. (1996). TGF-beta 1 and Ha-Ras collaborate in modulating the phenotypic plasticity and invasiveness of epithelial tumor cells. Gene Dev 10, 2462-2477.

Ogawa, K., Saito, A., Matsui, H., Suzuki, H., Ohtsuka, S., Shimosato, D., Morishita, Y., Watabe, T., Niwa, H., and Miyazono, K. (2007). Activin-Nodal signaling is involved in propagation of mouse embryonic stem cells. J Cell Sci 120, 55-65.

Onder, T. T., Gupta, P. B., Mani, S. A., Yang, J., Lander, E. S., and Weinberg, R. A. (2008). Loss of E-cadherin promotes metastasis via multiple downstream transcriptional pathways. Cancer Res 68, 3645-3654.

Pece, S., Tosoni, D., Confalonieri, S., Mazzarol, G., Vecchi, M., Ronzoni, S., Bernard, L., Viale, G., Pelicci, P. G., and Di Fiore, P. P. (2010), Biological and molecular heterogeneity of breast cancers correlates with their cancer stem cell content. Cell 140, 62-73.

Pukrop, T., Klemm, F., Hagemann, T., Gradl, D., Schulz, M., Siemes, S., Trumper, L., and Binder, C. (2006). Wnt 5a signaling is critical for macrophage-induced invasion of breast cancer cell lines. Proc Natl Acad Sci USA 103, 5454-5459.

Rider, D. A., Dombrowski, C., Sawyer, A. A., Ng, G. H., Leong, D., Hutmacher, D. W., Nurcombe, V., and Cool, S. M. (2008). Autocrine fibroblast growth factor 2 increases the multipotentiality of human adipose-derived mesenchymal stem cells. Stem cells (Dayton, Ohio) 26, 1598-1608, Savagner, P., Kusewitt, D. F., Carver, E. A., Magnino, F., Choi, C., Gridley, T., and Hudson, L. G. (2005). Developmental transcription factor slug is required for effective re-epithelialization by adult keratinocytes. J Cell Physiol 202, 858-866.

Senoo, M., Pinto, F., Crum, C. P., and McKeon, F. (2007). p63 Is essential for the proliferative potential of stem cells in stratified epithelia. Cell 129, 523-536.

Shimono, Y., Zabala, M., Cho, R. W., Lobo, N., Dalerba, P., Qian, D., Diehn, M., Liu, H., Panula, S. P., Chiao, E., et al. (2009). Downregulation of miRNA-200c links breast cancer stem cells with normal stem cells. Cell 138, 592-603.

Shirakihara, T., Saitoh, M., and Miyazono, K. (2007). Differential regulation of epithelial and mesenchymal markers by deltaEF1 proteins in epithelial mesenchymal transition induced by TGF-beta. Mol Biol Cell 18, 3533-3544.

Singh, A., and Settleman, J. EMT, cancer stem cells and drug resistance: an emerging axis of evil in the war on cancer. Oncogene.

Stingl, J. (2009). Detection and analysis of mammary gland stem cells. The Journal of pathology 217, 229-241.

Stingl, J., Eaves, C. J., Zandieh, I., and Emerman, J. T. (2001). Characterization of bipotent mammary epithelial progenitor cells in normal adult human breast tissue. Breast cancer research and treatment 67, 93-109.

Suzuki, H., Watkins, D. N., Jair, K. W., Schuebel, K. E., Markowitz, S. D., Chen, W. D., Pretlow, T. P., Yang, B., Akiyama, Y., Van Engeland, M., et al. (2004). Epigenetic inactivation of SFRP genes allows constitutive WNT signaling in colorectal cancer. Nature genetics 36, 417-422.

Thiery, J. P., Acloque, H., Huang, R. Y., and Nieto, M. A. (2009). Epithelial-mesenchymal transitions in development and disease. Cell 139, 871-890.

Thiery, J. P., and Chopin, D. (1999). Epithelial cell plasticity in development and tumor progression. Cancer Metastasis Rev 18, 31-42.

Toda, H., Tsuji, M., Nakano, I., Kobuke, K., Hayashi, T., Kasahara, H., Takahashi, J., Mizoguchi, A., Houtani, T., Sugimoto, T., et al. (2003). Stem cell-derived neural stem/progenitor cell supporting factor is an autocrine/paracrine survival factor for adult neural stem/progenitor cells. J Biol Chem 278, 35491-35500.

Van Obberghen-Schilling, E., Roche, N. S., Flanders, K. C., Sporn, M. B., and Roberts, A. B. (1988). Transforming growth factor beta 1 positively regulates its own expression in normal and transformed cells. J Biol Chem 263, 7741-7746, Veeman, M. T., Slusarski, D. C., Kaykas, A., Louie, S. H., and Moon, R. T. (2003). Zebrafish prickle, a modulator of noncanonical Wnt/Fz signaling, regulates gastrulation movements. Curr Biol 13, 680-685.

Visvader, J. E. (2009). Keeping abreast of the mammary epithelial hierarchy and breast tumorigenesis. Genes Dev 23, 2563-2577.

Wellner, U., Schubert, J., Burk, U. C., Schmalhofer, O., Zhu, F., Sonntag, A., Waldvogel, B., Vannier, C., Darling, D., zur Hansen, A., et al. (2009). The EMT-activator ZEB1 promotes tumorigenicity by repressing sternness-inhibiting microRNAs. Nat Cell Biol 11, 1487-1495.

Yang, J., Mani, S. A., Donaher, J. L., Ramaswamy, S., Itzykson, R. A., Come, C., Savagner, P., Gitelman, I., Richardson, A., and Weinberg, R. A. (2004). Twist, a master regulator of morphogenesis, plays an essential role in tumor metastasis, Cell 117, 927-939.

Yoeli-Lerner, M., Yiu, G. K., Rabinovitz, I., Erhardt, P., Jauliac, S., and Toker, A. (2005). Akt blocks breast cancer cell motility and invasion through the transcription factor NFAT. Molecular cell 20, 539-550.

Yu, F., Yao, H., Zhu, P., Zhang, X., Pan, Q., Gong, C., Huang, Y., Hu, X., Su, F., Lieberman, J., et al. (2007). let-7 regulates self renewal and tumorigenicity of breast cancer cells. Cell 131, 1109-1123.

Zavadil, J., Bitzer, M., Liang, D., Yang, Y. C., Massimi, A., Kneitz, S., Piek, E., and Bottinger, E. P. (2001). Genetic programs of epithelial cell plasticity directed by transforming growth factor-beta. Proc Natl Acad Sci USA 98, 6686-6691.

Zawel, L., Dai, J. L., Buckhaults, P., Zhou, S., Kinzler, K. W., Vogelstein, B., and Kern, S. E. (1998). Human Smad3 and Smad4 are sequence-specific transcription activators. Molecular cell 1, 611-617.

Zeisberg, M., Hanai, J., Sugimoto, H., Mammoto, T., Charytan, D., Strutz, F., and Kalluri, R. (2003). BMP-7 counteracts TGF-beta1-induced epithelial-to-mesenchymal transition and reverses chronic renal injury. Nature medicine 9, 964-968.

Irizarry, R. A., Hobbs, B., Collin, F., Beazer-Barclay, Y. D., Antonellis, K. J., Scherf, U., and Speed, T. P. (2003). Exploration, normalization, and summaries of high density oligonucleotide array probe level data. Biostatistics (Oxford, England) 4, 249-264.

Stewart, Dykxhoorn, D. M., Palliser, D., Mizuno, H., Yu, E. Y., An, D. S., Sabatini, D. M., Chen, I. S., Hahn, W. C., Sharp, P. A., et al. (2003). Lentivirus-delivered stable gene silencing by RNAi in primary cells. RNA (New York, N.Y. 9, 493-501.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.

Tojo, M., Hamashima, Y., Hanyu, A., Kajimoto, T., Saitoh, M., Miyazono, K., Node, M., and Imamura, T. (2005). The ALK-5 inhibitor A-83-01 inhibits Smad signaling and epithelial-to-mesenchymal transition by transforming growth factor-beta. Cancer science 96, 791-800.

* * *

Those skilled in the art will recognize, or be able to ascertain using no more than routine experimentation, many equivalents to the specific embodiments of the invention described herein. The scope of the present invention is not intended to be limited to the Description or the details set forth therein. Articles such as "a", "an" and "the" may mean one or more than one unless indicated to the contrary or otherwise evident from the context. It will be understood that many of the inventive methods are often practiced using populations of cells, e.g., in vitro or in vivo. Thus references to "a cell" should be understood as including embodiments in which the cell is a member of a population of cells, e.g., a population comprising or consisting of cells that are substantially genetically identical. However, the invention encompasses embodiments in which inventive methods is/are applied to an individual cell. Thus, references to "cells" should be understood as including embodiments applicable to individual cells within a population of cells and embodiments applicable to individual isolated cells.

Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. It is contemplated that all embodiments described herein are applicable to all different aspects of the invention. It is also contemplated that any of the embodiments can be freely combined with one or more other such embodiments whenever appropriate. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more elements or limitations found in any other claim that is dependent on the same base claim, and any claim that refers to an element present in a different claim can be modified to include one or more elements or limitations found in any other claim that is dependent on the same base claim as such claim. Furthermore, where the claims recite a composition, the invention provides methods of making the composition, e.g., according to methods disclosed herein, and methods of using the composition, e.g., for purposes disclosed herein. Where the claims recite a method, the invention provides compositions suitable for performing the method, and methods of making the composition. Also, where the claims recite a method of making a composition, the invention provides compositions made according to the inventive methods and methods of using the composition, unless otherwise indicated or unless one of ordinary skill in the art would recognize that a contradiction or inconsistency would arise.

Where elements are presented as lists, e.g., in Markush group format, each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

In addition, any particular embodiment(s), aspect(s), element(s), feature(s), etc., of the present invention, e.g., any compound, cell type, condition, disease, etc., may be explicitly excluded.

We claim:

1. A composition comprising one or more compounds selected from each of at least three of the following groups: (a) compounds that stimulate transforming growth factor (TGF)-beta pathway signaling; (b) compounds that stimulate canonical Wnt pathway signaling; (c) compounds that stimulate non-canonical Wnt pathway signaling; and (d) compounds that perturb cell adhesion, wherein the composition comprises at least one compound from group (b), and wherein the at least one compound of (b) disinhibits canonical Wnt pathway signaling by inhibiting a Dikkopf (DKK) or soluble Frizzled-related proteins (SFRP) family member.

2. The composition of claim 1, wherein the composition comprises one or more compounds selected from each of the following groups: (a) compounds that stimulate TGF-beta pathway signaling; and (c) compounds that stimulate non-canonical Wnt pathway signaling.

3. The composition of claim 1, comprising at least one compound from group (a), wherein the at least one compound of (a) comprises a TGF beta protein.

4. The composition of claim 1, comprising at least one compound from group (c), wherein the at least one compound of (c) stimulates the Wnt/Ca2+ pathway.

5. The composition of claim 1, comprising at least one compound from group (c), wherein the at least one compound of (c) comprises a Wnt5a or Wnt 16 protein.

6. The composition of claim 1, comprising at least one compound from group (d), wherein the at least one compound of (d) perturbs adherens junction or tight junction formation or maintenance.

7. The composition of claim 1, comprising at least one compound from group (d), wherein the at least one compound of (d) inhibits E-cadherin.

8. The composition of claim 1, wherein the compounds are present in concentrations effective to induce epithelial cells to undergo an epithelial-mesenchymal transition (EMT).

9. The composition of claim 1, further comprising epithelial cells.

10. The composition of claim 1, comprising TGF-beta 1, Wnt5a, a DKK1 inhibitor, an SFRP1 inhibitor, and an E-cadherin inhibitor.

11. The composition of claim 10, wherein the DKK1 inhibitor is an anti-DKK1 antibody.

12. The composition of claim 10, wherein the SFRP1 inhibitor is an anti-SFRP1 antibody.

13. The composition of claim 10, wherein the E-cadherin inhibitor is an anti-E-cadherin antibody.

14. The composition of claim 1, further comprising cell culture medium.

15. A composition comprising one or more compounds selected from each of at least three of the following groups: (a) compounds that stimulate TGF-beta pathway signaling; (b) compounds that stimulate canonical Wnt pathway signaling; (c) compounds that stimulate non-canonical Wnt pathway signaling; and (d) compounds that perturb cell adhesion, wherein the composition comprises at least one compound from group (d), wherein the at least one compound of (d) perturbs adherens junction or tight junction formation or maintenance.

16. A composition comprising one or more compounds selected from each of at least three of the following groups: (a) compounds that stimulate TGF-beta pathway signaling; (b) compounds that stimulate canonical Wnt pathway signaling; (c) compounds that stimulate non-canonical Wnt pathway signaling; and (d) compounds that perturb cell adhesion, wherein the compounds are present in concentrations effective to induce epithelial cells to undergo an EMT.

* * * * *